(12) United States Patent
Petryk

(10) Patent No.: US 12,268,733 B2
(45) Date of Patent: Apr. 8, 2025

(54) METHODS OF TREATING NEUROFIBROMATOSIS TYPE 1 AND RELATED CONDITIONS WITH ALKALINE PHOSPHATASE

(71) Applicant: Alexion Pharmaceuticals, Inc., Boston, MA (US)

(72) Inventor: Anna Petryk, New Haven, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 1101 days.

(21) Appl. No.: 17/265,894

(22) PCT Filed: Aug. 9, 2019

(86) PCT No.: PCT/US2019/045963
§ 371 (c)(1),
(2) Date: Feb. 4, 2021

(87) PCT Pub. No.: WO2020/033867
PCT Pub. Date: Feb. 13, 2020

(65) Prior Publication Data
US 2021/0162023 A1 Jun. 3, 2021

Related U.S. Application Data

(60) Provisional application No. 62/717,371, filed on Aug. 10, 2018.

(51) Int. Cl.
*A61P 35/00* (2006.01)
*A61B 6/03* (2006.01)
*A61K 38/18* (2006.01)
*A61K 38/46* (2006.01)

(52) U.S. Cl.
CPC ............ *A61K 38/465* (2013.01); *A61B 6/032* (2013.01); *A61K 38/1875* (2013.01); *A61P 35/00* (2018.01); *C12Y 301/03001* (2013.01)

(58) Field of Classification Search
None
See application file for complete search history.

(56) References Cited

U.S. PATENT DOCUMENTS

| | | | |
|---|---|---|---|
| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,112,341 B1 | 9/2006 | Nagarajan et al. |
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |
| 7,341,838 B2 | 3/2008 | Buechler et al. |
| 7,365,091 B2 | 4/2008 | Gravel et al. |
| 7,384,917 B2 | 6/2008 | Burnett, Jr. et al. |
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |

(Continued)

FOREIGN PATENT DOCUMENTS

CA 3161266 A1 6/2021
EP 0478797 B1 4/1995

(Continued)

OTHER PUBLICATIONS

Office Action for Chinese Patent Application No. 201780021666.7, issued on Jun. 20, 2022 (22 pages).

(Continued)

*Primary Examiner* — Alton N Pryor
(74) *Attorney, Agent, or Firm* — Clark & Elbing LLP

(57) ABSTRACT

The disclosure features methods for treating at least one symptom of neurofibromatosis type 1, treating at least one symptom of dystrophic scoliosis, or inducing bone healing by administering a soluble alkaline phosphatase (sALP) to the patient.

19 Claims, 6 Drawing Sheets
Specification includes a Sequence Listing.

(56) References Cited

U.S. PATENT DOCUMENTS

| | | |
|---|---|---|
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,650,412 B2 | 5/2017 | Konstantinov et al. |
| 9,650,413 B2 | 5/2017 | Konstantinov et al. |
| 9,908,932 B2 | 3/2018 | Malanson et al. |
| 9,988,620 B2 | 6/2018 | Crine et al. |
| 10,000,532 B2 | 6/2018 | Crine et al. |
| 10,052,366 B2 | 8/2018 | Crine et al. |
| 10,449,236 B2 | 10/2019 | Marozsan et al. |
| 10,603,361 B2 | 3/2020 | Odrijin |
| 11,229,686 B2 | 1/2022 | Pradhan et al. |
| 11,352,612 B2 | 6/2022 | Jaluria et al. |
| 11,913,039 B2 | 2/2024 | Godawat et al. |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Protter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0022728 A1 | 1/2009 | Lin |
| 2009/0023652 A1 | 1/2009 | Bell et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1 | 11/2010 | Crine et al. |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1 | 12/2013 | Crine et al. |
| 2014/0004096 A1 | 1/2014 | Nichols |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0015784 A1 | 1/2016 | Shaw et al. |
| 2016/0052968 A1 | 2/2016 | Crine et al. |
| 2016/0097100 A1 | 4/2016 | Trent et al. |
| 2017/0175094 A1 | 6/2017 | Hatch |
| 2017/0360899 A1 | 12/2017 | Marozsan et al. |
| 2018/0072986 A1 | 3/2018 | Park et al. |
| 2018/0230445 A1 | 8/2018 | Jaluria et al. |
| 2019/0043501 A1 | 2/2019 | Ramaci |
| 2019/0099473 A1 | 4/2019 | Fujita et al. |
| 2020/0101141 A1 | 4/2020 | Moseley et al. |
| 2020/0224182 A1 | 7/2020 | Rajendran et al. |
| 2020/0282012 A1 | 9/2020 | Francois |
| 2021/0169994 A1 | 6/2021 | Voegtli et al. |
| 2021/0317425 A1 | 10/2021 | Godawat et al. |
| 2022/0154155 A1 | 5/2022 | Godawat et al. |
| 2023/0372456 A1* | 11/2023 | Petryk .................... A61P 19/08 |

FOREIGN PATENT DOCUMENTS

| | | |
|---|---|---|
| EP | 0769554 A2 | 4/1997 |
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |

(56) References Cited

FOREIGN PATENT DOCUMENTS

| | | |
|---|---|---|
| EP | 0497368 B1 | 6/2002 |
| EP | 1492567 | 9/2003 |
| EP | 1502604 A1 | 2/2005 |
| EP | 1623994 A2 | 2/2006 |
| EP | 1759710 A1 | 3/2007 |
| EP | 0771875 B1 | 2/2008 |
| EP | 1985697 A1 | 10/2008 |
| EP | 1759001 B1 | 4/2011 |
| EP | 2158319 B1 | 12/2011 |
| EP | 3250227 A2 | 12/2017 |
| JP | 8-70875 A | 3/1996 |
| JP | 2000-327583 A | 11/2000 |
| JP | 2002-541776 A | 12/2002 |
| JP | 2007-511209 A | 5/2007 |
| JP | 2007-537725 A | 12/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| JP | 2014-181229 A | 9/2014 |
| JP | 2015-502336 A | 1/2015 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/087802 A2 | 9/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005/105156 A1 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079400 A2 | 7/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/133511 A2 | 11/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/006732 A9 | 1/2009 |
| WO | WO-2009/015011 A1 | 1/2009 |
| WO | WO-2009/023270 A2 | 2/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/130229 A1 | 10/2011 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2013/071262 A1 | 5/2013 |
| WO | WO-2013/169397 A1 | 11/2013 |
| WO | WO-2015/112015 A1 | 7/2015 |
| WO | WO-2015/112017 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2016/153191 A1 | 9/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |
| WO | WO-2018/164995 A1 | 9/2018 |
| WO | WO-2021/081026 A1 | 4/2021 |
| WO | WO-2021/119218 A1 | 6/2021 |

OTHER PUBLICATIONS

International Search Report and Written Opinion for International Patent Application No. PCT/US2022/025648, mailed Jul. 22, 2022 (12 pages).
Notice of Final Rejection for Korean Patent Application No. 10-2018-7028255, dated Aug. 18, 2022 (7 pages).

(56) References Cited

OTHER PUBLICATIONS

Office Action for Brazilian Patent Application No. BR112018070243-9, dated Sep. 7, 2022 (10 pages).
International Search Report and Written Opinion of the International Searching Authority for International Application No. PCT/US2020/064140, mailed Apr. 23, 2021 (12 pages).
GenBank NM_000478.2, "*Homo sapiens* alkaline phosphatase, liver/bone/kidney (ALPL), mRNA," <https://www.ncbi.nlm.nih.gov/nuccore/NM_000478.2>, dated Sep. 17, 2006, retrieved on Feb. 23, 2021 (7 pages).
International Search Report and Written Opinion for International Patent Application No. PCT/US2022/016031, mailed May 3, 2022 (9 pages).
Office Action for Canadian Patent Application No. 2,993,358, dated Sep. 20, 2022 (6 pages).
An et al., "IgG2m4, an engineered antibody isotype with reduced Fc function," mAbs. 1(6): 572-579 (2009).
Komaru et al., "Molecular and cellular basis of hypophosphatasia," J Oral Biosci. 61(3):141-148 (Sep. 2019).
Sharma et al., "Alkaline Phosphatase: An Overview," Indian J Clin Biochem. 29(3):269-278 (2014).
Luo et al., "Lower ultrafiltration temperature improves membrane performance and emulsifying properties of milk protein concentrates," Dairy Sci. & Technol. 95(1):15-31 (Sep. 2014).
Klidaras et al., "Fracture Healing in Two Adult Patients With Hypophosphatasia After Asfotase Alfa Therapy," JBMR Plus. 2(5):304-307 (May 2018).
Whyte et al., "Supplemental Data: Asfotase alfa therapy for children with hypophosphatasia," JCI Insight. 1(9):e85971 (Jun. 2016) (33 pages).
"Strensiq: Assessment Report," European Medicines Agency, dated Jun. 25, 2015 (92 pages).
Office Action for Japanese Patent Application No. 2021-506690, dated May 30, 2023 (10 pages).
Dutta et al., "Men and mice: Relating their ages," Life Sci. 152:244-8 (2016) (5 pages).
Zhang et al., "Engineering *E. coli* Alkaline Phosphatase Yields Changes of Catalytic Activity, Thermal Stability and Phosphate Inhibition," Biocatal Biotransfor. 20(6):381-389 (2002).
Nangia et al., "Disorders of Calcium Metabolism in Newborns," Journal of Neonatology. 17(2):43-49 (2003).
Kochanowski et al., "Medium and feed optimization for fed-batch production of a monoclonal antibody in CHO cells," BMC Proc. 5(Suppl 8):P75 (2011) (3 pages).
"Data file 29-0929-25 AA. Xcellerex™ XDR cell culture bioreactor systems," GE Healthcare Life Sciences, published Feb. 2014 (4 pages).
Yagasaki et al., "Animal Cell Technology: Basic & Applied Aspects," Proceedings of the Fifteenth Annual Meeting of the Japanese Association for Animal Cell Technology (JAACT), vol. 13, Fuchu, Nov. 11-15, 2002 (461 pages).
Kozlenkov et al., "Residues determining the binding specificity of uncompetitive inhibitors to tissue-nonspecific alkaline phosphatase," J Bone Miner Res. 19(11):1862-72 (2004).
NCBI Database Accession No. NM_000478.2, <https://www.ncbi.nlm.nih.gov/nuccore/NM_000478.2>, retrieved on Feb. 23, 2021 (7 pages).
Pradhan et al., "Exposure-Response Modeling and Simulation to Support Evaluation of Efficacious and Safe Exposure and Dose Range for Asfotase alfa in Patients with Hypophosphatasia," ASBMR 2015 Annual Meeting Abstracts. J Bone and Med Res. SU0380:S316 (2015) (1 page).
Abbruzzese, "The Tinetti Performance-Oriented Mobility Assessment Tool," Am J Nursing. 98(12):16J-16L (1998) (3 pages).
International Search Report and Written Opinion for International Patent Application No. PCT/US20/64140, mailed Apr. 23, 2021 (16 pages).
Kishnani et al., "Five-year efficacy and safety of asfotase alfa therapy for adults and adolescents with hypophosphatasia," Bone. 121:149-162 (2019).
Alexion Pharmaceuticals, "Safety Study of Human Recombinant Tissue Non-Specific Alkaline Phosphatase Fusion Protein Asfotase Alfa in Adults With Hypophosphatasia (HPP)," ClinicalTrials.gov. NCT00739505, <https://www.clinicaltrials.gov/ct2/show/NCT00739505>, last updated Mar. 29, 2019 (8 pages).
Alexion Pharmaceuticals, "Safety and Efficacy Study of Asfotase Alfa in Adolescents and Adults With Hypophosphatasia (HPP)," ClinicalTrials.gov. NCT01163149, <https://clinicaltrials.gov/ct2/show/NCT01163149>, last updated Mar. 13, 2019 (9 pages).
Alexion Pharmaceuticals, "Strensiq™ (asfotase alfa) for injection," retrieved from <globalgenes.org/2015/11/05/alexion-announces-fda-approval-for--strensiq/?gclid=CjwKCAjwwqaGBhBKEiwAMk-FtFQOKvuVN-WmNcDVyu9Q9X3f6QB-VOTwo0x216TR2H4_Qc6jSIhvxoCILMQAvD_BWE>, dated Nov. 5, 2015 (1 page).
European Medicines Agency, "Strensiq: Asfotase Alfa," <www.ema.europa.eu/en/medicines/human/EPAR/strensiq>, last updated Mar. 25, 2021 (8 pages).
Hofmann et al., "Efficacy and safety of asfotase alfa in infants and young children with hypophosphatasia: a phase 2 open-label study," J Clin Endocrinol Metab. 104(7):2735-2747 (2019) (14 pages).
Kim et al., "CHO cells in biotechnology for production of recombinant proteins: current state and further potential," Appl Microbiol Biotechnol. 93(3):917-30 (2012).
McCormack et al., "Is bigger better? An argument for very low starting doses," CMAJ. 183(1):65-9 (2011).
Rush, "Childhood hypophosphatasia: to treat or not to treat," Orphanet J Rare Dis. 13(1):116 (2018) (5 pages).
Phillips et al., "Clinical Outcome Assessments: Use of Normative Data in a Pediatric Rare Disease," Value Health. 21(5):508-514 (2018).
"Effects of feeding strategy on CHO cell performance in fed-batch cultures using HyClone ActiPro medium and Cell Boost 7a and 7b supplements," Cytiva, <http://www.processdevelopmentforum.com/posters/effects-of-feeding-strategy-on-cho-cell-performance-in-fed-batch-cultures/>. 2017 (5 pages).
Witkowski et al., "Conversion of a beta-ketoacyl synthase to a malonyl decarboxylase by replacement of the active-site cysteine with glutamine," Biochemistry. 38(36):11643-50 (1999).
Whisstock et al., "Prediction of protein function from protein sequence and structure," Q Rev Biophys. 36(3):307-40 (2003).
Pharmaceutical and Food Safety Bureau Examination and Management Division / Pharmaceuticals and Medical Devices Agency, Review Report. 1-63 (2015) (English Abstract).
"Sequence 4," Score Search Results for U.S. Appl. No. 12/599,679, retrieved Nov. 17, 2018 (2 pages).
"View of NCT02235493 on Nov. 19, 2015," ClinicalTrials.gov archive, updated Nov. 19, 2015, retrieved Jan. 27, 2017 (4 pages).
Achord et al., "Human beta-glucuronidase: in vivo clearance and in vitro uptake by a glycoprotein recognition system on reticuloendothelial cells," Cell. 15(1):269-278 (1978).
Addison et al., "Pyrophosphate inhibits mineralization of osteoblast cultures by binding to mineral, up-regulating osteopontin, and inhibiting alkaline phosphatase activity," J Biol Chem. 282(21):15872-83 (2007).
Advisory Action for U.S. Appl. No. 11/484,870, mailed Dec. 20, 2007 (4 pages).
Agochukwu et al., "Hearing loss in syndromic craniosynostoses: Introduction and consideration of mechanisms," available in PMC Aug. 13, 2014, published in final edited form as: Am J Audiol. 23(2):135-41 (2014) (13 pages).
Ahn et al., "Idiopathic calcium pyrophosphate dihydrate (CPPD) crystal deposition disease in a young male patient: a case report," J Korean Med Sci. 18(6):917-20 (2003).
Alexion Pharma International, "Product Monograph, Including Patient Medication Information. Strensiq™ (asfotase alfa), Solution for Injection 40 mg/mL & 100 mg/mL," <alexionpharma.ca/documents/Strensiq-PM-asfotase-alfa-14Aug2015.aspx>, prepared Aug. 14, 2015 (32 pages).
Alexion Third Quarter 2017 Earnings Call, "files.shareholder.com/downloads/ALXN/5636824573x0x961197/3B361D6E-80E2-463E-B0E5-3EAD7FC5B9D0/Alexion_Q3_2017_Earnings_Slides.pdf," 2017 (43 pages).

(56) References Cited

OTHER PUBLICATIONS

Alexion, "Highlights of Prescribing Information" for Strensiq®, 2018 (8 pages).
Ali et al., "Isolation and characterization of calcifying matrix vesicles from epiphyseal cartilage," Proc Natl Acad Sci USA. 67(3):1513-20 (1970).
Altarescu et al., "The efficacy of enzyme replacement therapy in patients with chronic neuronopathic Gaucher's disease," J Pediatr. 138(4):539-547 (2001).
Anderson et al., "Impaired calcification around matrix vesicles of growth plate and bone in alkaline phosphatase-deficient mice," Am J Pathol. 164(3):841-7 (2004).
Anderson et al., "Matrix vesicles in osteomalacic hypophosphatasia bone contain apatite-like mineral crystals," Am J Pathol. 151(6):1555-61 (1997).
Anderson et al., "Pyrophosphate stimulation of calcium uptake into cultured embryonic bones. Fine structure of matrix vesicles and their role in calcification," Dev Biol. 34:211-227 (1973).
Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).
Anderson et al., "The role of matrix vesicles in growth plate development and biomineralization," Front Biosci. 10:822-37 (2005).
Anderson, "Mechanism of Mineral Formation in Bone," *Pathology Reviews*. Emanuel Rubin and Ivan Damjanov (eds.), 13-23 (1990).
Appeal Brief as Filed in U.S. Appl. No. 12/638,527, dated Oct. 9, 2015 (101 pages).
Attwood, "The Babel of Bioinformatics," Science. 290(5491):471-3 (2000).
Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).
Barcia et al., "Infantile hypophosphatasia: treatment options to control hypercalcemia, hypercalciuria, and chronic bone demineralization," J Pediatr. 130(5):825-8 (1997).
Barranger et al., "Lessons learned from the development of enzyme therapy for Gaucher disease," J Inherit Metab Dis. 24(Suppl. 2):89-96 (2001).
Barton et al., "Replacement therapy for inherited enzyme deficiency—macrophage-targeted glucocerebrosidase for Gaucher's disease," N Engl J Med. 324(21):1464-70 (1991) (1 page) (Abstract only).
Barvencik et al., "Skeletal mineralization defects in adult hypophosphatasia—a clinical and histological analysis," Osteoporosis Int. 22(10):2667-75 (2011).
Baumgartner-Sigl et al., "Pyridoxine-responsive seizures as the first symptom of infantile hypophosphatasia caused by two novel missense mutations (c.677T>C, p.M226T; c. 1112C>T, p.T371I) of the tissue-nonspecific alkaline phosphatase gene," Bone. 40(6):1655-61 (2007).
Beck et al., "Whole-body MRI in the childhood form of hypophosphatasia," Rheumatol Int. 31(10):1315-20 (2011).
Beederman et al., "Molecular basis of cranial suture biology and disease: osteoblastic and osteoclastic perspectives," Genes Dis. 1(1):120-5 (2014).
Beertsen et al., "Root development in mice lacking functional tissue non-specific alkaline phosphatase gene: Inhibition of acellular cementum formation," J Dent Res. 78(6):1221-1229 (1999) (10 pages).
Belachew et al., "Infantile hypophosphatasia secondary to a novel compound heterozygous mutation presenting with pyridoxine-responsive seizures," JIMD Rep. 11:17-24 (2013).
Belkhouribchia et al., "Osteomalacia with low alkaline phosphatase: a not so rare condition with important consequences," BMJ Case Rep. doi: 10.1136/bcr-2015-212827 (2016) (4 pages).
Bennett et al., "Extracellular domain-IgG fusion proteins for three human natriuretic peptide receptors," J Biol Chem. 266(34):23060-23067 (1991).
Berkseth et al., "Clinical spectrum of hypophosphatasia diagnosed in adults," Bone. 54(1):21-7 (2013).
Bernard, "Ultrastructural localization of alkaline phosphatase in initial intramembranous osteogenesis," Clin Orthop Relat Res. (135):218-25 (1978).
Bernardi, "Chromatography of proteins on hydroxyapatite," Methods Enzymol. 27:471-9 (1973).
Bhattacharyya et al., "Hypophosphatasia and the risk of atypical femur fractures: a case-control study," BMC Muscoloskelet Disord. 17:332 (2016) (4 pages).
Bianchi, "Hypophosphatasia: an overview of the disease and its treatment," Osteoporos Int. 26(12):2743-57; DOI 10.1007/s00198-015-3272-1 (2015) (15 pages).
Bishop et al., "Transformative therapy in hypophosphatasia," Arch Dis Child. 101(6):514-5 (2016).
Bishop, "Asfotase alfa for hypophosphatasia," Horizon Scanning Centre. National Institute for Health Research. www.hsric.nihr.ac.uk/topics/asfotase-alfa-for-hypophosphatasia/download, retrieved Oct. 20, 2013 (9 pages).
Bishop, "Clinical management of hypophosphatasia," Clin Cases Miner Bone Metab. 12(2):170-3 (2015).
Bloch-Zupan, "Hypophosphatasia: diagnosis and clinical signs—a dental surgeon perspective," Int J Paediatr Dent. 26(6):426-438 (2016).
Bobryshev et al., "Role of bone-type tissue-nonspecific alkaline phosphatase and PHOSPO1 in vascular calcification," Curr Pharm Des. 20(37):5821-8 (2014).
Bobyr et al., "High-resolution analysis of Zn(2+) coordination in the alkaline phosphatase superfamily by EXAFS and x-ray crystallography," J Mol Biol. 415(1):102-17 (2012).
Bobé et al., "Fas-mediated liver damage in MRL hemopoietic chimeras undergoing lpr-mediated graft-versus-host disease," J Immunol. 159:4197-4204 (1997).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Bonilla, "Pharmacokinetics of immunoglobulin administered via intravenous or subcutaneous routes," Immunol Allergy Clin N Am. 28:803-819 (2008).
Boskey et al., "Matrix vesicles promote mineralization in a gelatin gel," Calcif Tissue Int. 60(3):309-15 (1997).
Boskey, "Amorphous calcium phosphate: The contention of bone," J Dent Res. 76(8):1433-1436 (1997).
Boulet et al., "A population-based study of craniosynostosis in metropolitan Atlanta, 1989-2003," Am J Med Genet A. 146A(8):984-91 (2008).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Braunstein, "Multiple fractures, pain, and severe disability in a patient with adult-onset hypophosphatasia," Bone Rep. 4:1-4 (2016).
Brenner et al., "Diverse biological actions of atrial natriuretic peptide," Physiol Rev. 70(3):665-699 (1990).
Briot et al., "Adult hypophosphatasia," Curr Opin Rheumatol. 28(4):448-51 (2016).
Buchet et al., "Chapter 3: Multisystemic functions of alkaline phosphatases," *Phosphatase Modulators, Methods in Molecular Biology*, vol. 1053. José Luis Millán (ed.), 27-51 (2013).
Byers et al., "Effect of enzyme replacement therapy on bone formation in a feline model of mucopolysaccharidosis type VI," Bone. 21(5):425-431 (1997).
Cahill et al., "Infantile hypophosphatasia: transplantation therapy trial using bone fragments and cultured osteoblasts," J. Clin Endocrinol Metab. 92(8):2923-30 (2007).
Cameron et al., "Minireview: Natriuretic peptides during development of the fetal heart and circulation," Endocrinology. 144(6):2191-2194 (2003).
Campbell et al., "Insulin-like growth factor (IGF)-binding protein-5-(201-218) region regulates hydroxyapatite and IGF-I binding," Am J Physiol Endocrinol Metab. 273:E1005-1013 (1997).

(56) References Cited

OTHER PUBLICATIONS

Carden et al., "Tracheomalacia and tracheobronchomalacia in children and adults: an in-depth review," Chest. 127(3):984-1005 (2005).
Center for Drug Evaluation and Research, "Application No. 125513Orig1s000," <www.accessdata.fda.gov/drugsatfda_docs/nda/2015/125513Orig1s000MedR.pdf>, review completed Oct. 20, 2015; retrieved on Jun. 1, 2016 (254 pages).
Chan et al., "Endoscope-assisted versus open repair of craniosynostosis: a comparison of perioperative cost and risk," J Craniofac Surg. 24(1):170-4 (2013).
Chen et al., "Gly369Cys mutation in mouse FGFR3 causes achondroplasia by affecting both chondrogenesis and osteogenesis," J Clin Invest. 104(11):1517-1525 (1999).
Choe et al., "Substrate profiling of cysteine proteases using a combinatorial peptide library identifies functionally unique specificities," J Biol Chem. 281(18):12824-12832 (2006).
Choi et al., "Craniosynostosis in growing children: pathophysiological changes and neurosurgical problems," J Korean Neurosurg Soc. 59(3):197-203 (2016).
Chong et al., "Minimally invasive suturectomy and postoperative helmet therapy: advantages and limitations," J Korean Neurosurg Soc. 59(3):227-32 (2016).
Chusho et al., "Dwarfism and early death in mice lacking C-type natriuretic peptide," Proc Natl Acad Sci USA. 98(7):4016-4021 (2001).
Ciancaglini et al., "Contribution of matrix vesicles and alkaline phosphatase to ectopic bone formation," Braz J Med Biol Res. 39(5):603-10 (2006).
Clarke, "Normal bone anatomy and physiology," Clin J Am Soc Nephrol. 3(Suppl 3):S131-9 (2008).
Cleland et al., "Emerging protein delivery methods," Curr Opin Biotechnol. 12:212-219 (2001).
Clemens et al., "Pharmacokinetics and biological actions of subcutaneously administered human brain natriuretic peptide," J Pharmacol Exp Ther. 287(1):67-71 (1998).
Colantonio et al., "Closing the gaps in pediatric laboratory reference intervals: a Caliper database of 40 biochemical markers in a healthy and multiethnic population of children," Clin Chem. 58(5):854-68 (2012).
Collmann et al., "Neurosurgical aspects of childhood hypophosphatasia," Childs Nerv Syst. 25(2):217-23 (2009).
Communication from Examining Division for European Application No. 05739065.0, dated Jun. 11, 2010 (5 pages).
Communication from Examining Division for European Application No. 05739065.0, dated Jun. 18, 2009 (6 pages).
Communication from Examining Division for European Application No. 08757088.3, dated Apr. 20, 2011 (4 pages).
Communication pursuant to Rule 164(2)(b) and Article 94(3) EPC for European Patent Application No. 16707571.2, dated Feb. 26, 2019 (12 pages).
Crawley et al., "Enzyme replacement therapy in a feline model of Maroteaux-Lamy syndrome," J Clin Invest. 97(8):1864-73 (1996).
Czerwinski et al., "Major morbidity and mortality rates in craniofacial surgery: an analysis of 8101 major procedures," Plast Reconstr Surg. 126(1):181-6 (2010).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
Data Sheet for pFUSE-SEAP-hFC "Plasmid designed for the expression of a SEAP-Fc Fusion protein," Invivogen, San Diego, CA (1 page) (1989).
de la Croix Ndong et al., "Asfotase-alpha improves bone growth, mineralization and strength in mouse models of neurofibromatosis type-1," Nat Med. 20(8):904-10 (2014) (10 pages).
de Plater et al., "The natriuretic peptide (OVCNP-39) from platypus (*Ornithorhynchus anatinus*) venom relaxes the isolated rat uterus and promotes oedema and mast cell histamine release," Toxicon. 36(6):847-857 (1998).
de Roo et al., "Infantile hypophosphatasia without bone deformities presenting with severe pyridoxine-resistant seizures," Mol Genet Metab. 111(3):404-7 (2014).
Declaration of Dr. Philippe Crine for European Patent Application No. 08757088.3, executed Jan. 14, 2011 (6 pages).
Deeb et al., "Could alerting physicians for low alkaline phosphatase levels be helpful in early diagnosis of hypophosphatasia?," J Clin Res Pediatr Endocrinol. 10(1):19-24 (2018).
del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).
Di Mauro et al., "Kinetic characterization of hypophosphatasia mutations with physiological substrates," J Bone Miner Res. 17(8):1383-91 (2002).
Di Rocco et al. "Craniosynostosis and hypophosphatasia," Arch Pediatr. 24(5S2):5S89-5S92 (2017).
Dortschy et al., "Bevölkerungsbezogene verteilungswerte ausgewählter laborparameter aus der studie zur gesundheit von kindern und jugendlichen in Deutschland (KiGGS)," Gesundheitsberichterstattung des Bundes, Robert Koch Institute (2009) (136 pages).
Dumont et al., "Monomeric Fc fusions: impact on pharmacokinetic and biological activity of protein therapeutics," BioDrugs. 20(3):151-60 (2006).
Durussel et al., "Bone mineralization-dependent craniosynostosis and craniofacial shape abnormalities in the mouse model of infantile hypophosphatasia," Dev Dyn. 245(2):175-82 (2016).
Eade et al., "Pyrophosphate arthropathy in hypophosphatasia," Ann Rheum Dis. 40(2):164-70 (1981).
EBI Blast for Accession No. ATD17216. Entered Oct. 16, 2008 (1 page).
Eng et al., "Safety and efficacy of recombinant human alpha-galactosidase A replacement therapy in Fabry's disease," N Engl J Med. 345(1):9-16 (2001).
Engel et al., "Characterization of the hormone binding site of natriuretic peptide receptor-C," FEBS Lett. 360(2):169-172 (1995).
Epps, "Application No. 125513Orig1s000 Medical Review(s)," Center for Drug Evaluation and Research, <www.accessdata.fda.gov/drugsatfda_docs/nda/2015/125513Orig1s000MedR.pdf>, Oct. 20, 2015 (254 pages).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugía. 19(6):509-29 (2008).
European Collection of Authenticated Cell Cultures (ECACC), General Cell Collection: NS0, Catalogue No. 85110503. Retrieved May 2, 2018 (3 pages).
Examiner's Answer to Appeal Brief for U.S. Appl. No. 12/638,527, mailed Feb. 23, 2016 (9 pages).
Extended European Search Report for European Application No. 08757088.3, dated Jun. 21, 2010 (6 pages).
Extended European Search Report for European Application No. 11000196.3, mailed Jun. 22, 2011 (6 pages).
Extended European Search Report for European Application No. 11004496.3, mailed Aug. 26, 2011 (7 pages).
Extended European Search Report for European Application No. 11774253.6, dated Oct. 14, 2013 (8 pages).
Extended European Search Report for European Application No. 15907550.6, dated Jun. 4, 2019 (7 pages).
Extended European Search Report for European Application No. 18173111.8, dated Aug. 21, 2018 (9 pages).
Extended European Search Report for European Patent Application No. 12842640.0, dated Mar. 13, 2015 (7 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Farnum et al., "In vivo delivery of fluoresceinated dextrans to the murine growth plate: imaging of three vascular routes by multiphoton

(56) References Cited

OTHER PUBLICATIONS microscopy," available in PMC Oct. 28, 2008, published in final edited form as: Anat Rec a Discov Mol Cell Evol Biol. 288(1):91-103 (2006) (22 pages).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Fodor et al., "Differencial diagnosis of the low alkaline phosphatase activities," Orv Hetil. 158(26):1003-1007 (2017) (Article in Hungarian) (English Abstract included).
Fong et al., "Hypocalcemia: Updates in diagnosis and management for primary care," Can Fam Physician. 58(2):158-62 (2012).
Fraser, "Hypophosphatasia," Am J Med. 22(5):730-46 (1957).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).
Fujisawa et al., "Acidic amino acid-rich sequences as binding sites of osteonectin to hydroxyapatite crystals," Biochim Biophys Acta. 1292:53-60 (1996).
Furbish et al., "Uptake and distribution of placental glucocerebrosidase in rat hepatic cells and effects of sequential deglycosylation," Biochim Biophys Acta. 673:425-434 (1981).
Furuya et al., "Structural requirements of C-type natriuretic peptide for elevation of cyclic GMP in cultured vascular smooth muscle cells," Biochem Biophys Res Commun. 183(3):964-969 (1992).
Garber et al., "Comparing outcomes and cost of 3 surgical treatments for sagittal synostosis: a retrospective study including procedure-related cost analysis," Neurosurgery. 81(4):680-7 (2017).
Garg, "Investigation of the role of FcRn in the absorption, distribution, and elimination of monoclonal antibodies," Dissertation: State University of New York at Buffalo, 2007 (Abstract only) (2 pages).
Gasque et al., "Improvement of the skeletal and dental hypophosphatasia phenotype in Alpl−/− mice by administration of soluble (non-targeted) chimeric alkaline phosphatase," Available in PMC Mar. 1, 2016, published in final edited form as: Bone. 72:137-147 (2015) (25 pages).
Gates et al., "Effects of age, sex, and comorbidities on the pediatric outcomes data collection instrument (PODCI) in the general population," J Pediatr Orthop. 35(2):203-9 (2015).
Gilbert et al., "Chimeric peptides of statherin and osteopontin that bind hydroxyapatite and mediate cell adhesion," J Biol Chem. 275(21):16213-8 (2000).
Ginelliová et al., "Sudden death associated with syndromic craniosynostosis," Forensic Sci Med Pathol. 12(4):506-9 (2016).
Glass et al., "The infant skull: a vault of information," Radiographics. 24(2):507-22 (2004).
Graham et al., "Characteristics of a human cell line transformed by DNA from human adenovirus type 5," J Gen Virol. 36(1):59-72 (1977).
Greenberg et al., "A homoallelic Gly$^{317}$ to Asp mutation in *ALPL* causes the perinatal (lethal) form of hypophosphatasia in Canadian Mennonites," Genomics. 17:215-217 (1993).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Guo et al. "Protein tolerance to random amino acid change," Proc Natl Acad Sci USA. 101(25):9205-9210 (2004).
Güzel Nur et al., "Pyridoxine-responsive seizures in infantile hypophosphatasia and a novel homozygous mutation in ALPL gene," J Clin Res Pediatr Endocrinol. 8(3):360-4 (2016).
Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol Cell Physiol. 270:C1311-18 (1996) (9 pages).
Halling Linder et al., "Glycosylation differences contribute to distinct catalytic properties among bone alkaline phosphatase isoforms," available in PMC Nov. 1, 2010, published in final edited form as: Bone. 45(5):987-993 (2009) (17 pages).
Hancarova et al. "Hypophosphatasia due to uniparental disomy," Bone. 81:765-766 (2015).
Hardy et al., "Dissection of a carboxy-terminal region of the yeast regulatory protein RAP1 with effects on both transcriptional activation and silencing," Mol Cell Biol. 12(3):1209-1217 (1992).
Harmey et al., "Concerted regulation of inorganic pyrophosphate and osteopontin by *Akp2, Enpp1, and Ank*," Am J Pathol. 164(4):1199-1209 (2004).
Harmey et al., "Elevated skeletal osteopontin levels contribute to the hypophosphatasia phenotype in $Akp2^{-/-}$ mice," J Bone Miner Res. 21(9):1377-1386 (2006).
Harris, "The human alkaline phosphatases: what we know and what we don't know," Clin Chim Acta. 186(2):133-50 (1989).
Hawrylak et al., "The solubilization of tetrameric alkaline phosphatase from human liver and its conversion into various forms by phosphatidylinositol phospholipase C or proteolysis," J Biol Chem. 263(28):14368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Henthorn et al., "Missense mutations of the tissue-nonspecific alkaline phosphatase gene in hypophosphatasia," Clin Chem. 38(12):2501-5 (1992).
Herasse et al., "Molecular study of three cases of odontohypophosphatasia resulting from heterozygosity for mutations in the tissue non-specific alkaline phosphatase gene," J Med Genet. 40(8):605-9 (2003).
Herring, "Mechanical influences on suture development and patency," Front Oral Biol. 12:41-56 (2008).
Hessle et al., "Tissue-nonspecific alkaline phosphatase and plasma cell membrane glycoprotein-1 are central antagonistic regulators of bone mineralization," Proc Natl Acad Sci USA. 99(14): 9445-9449 (2002).
Highlights of Prescribing Information for Strensiq™ (asfotase alfa) Injection, Alexion Pharmaceuticals, Inc., <www.alexion.com/Documents/strensiq_pi-10-2015.aspx> (2015) (19 pages).
Hofmann et al., "Asfotase alfa: enzyme replacement for the treatment of bone disease in hypophosphatasia," Drugs Today (Barc). 52(5):271-85 (2016).
Hofmann et al., "Clinical aspects of hypophosphatasia: an update," Clinic Rev Bone Miner Metab. 11(2):60-70 (2013).
Hofmann et al., "Compound heterozygosity of two functional null mutations in the ALPL gene associated with deleterious neurological outcome in an infant with hypophosphatasia," Bone. 55:150-7 (2013).
Hofmann et al., "Improvement in bone manifestations and respiratory status in infants and young children with HPP treated with asfotase alfa: an update on the ENB-010-10 trial," 7th International Conference on Children's Bone Health, Jun. 27-30, Salzburg, Austria. Bone Abstracts. 4:OC18 (2015) (3 pages).
Hofmann et al., "Chapter 15: Recombinant enzyme replacement therapy in hypophosphatasia," *Neuronal Tissue-Nonspecific Alkaline Phosphatase (TNAP): Subcellular Biochemistry*. Caroline Fonta and Laszlo Negyessy, 76:323-41 (2015).
Hollis et al., "Current concepts in hypophosphatasia: case report and literature review," Int J Paediatr Dent. 23(3):153-9 (2013).
Horton et al., "Achondroplasia," Lancet. 370:162-72 (2007).
Hosain et al., "Targeted delivery of antineoplastic agent to bone: biodistribution studies of technetium-99m-labeled gem-bisphosphonate conjugate of methotrexate," J Nucl Med. 37(1):105-7 (1996).
Hult et al., "Engineered enzymes for improved organic synthesis," Curr Opin Biotechnol. 14:395-400 (2003).

(56) References Cited

OTHER PUBLICATIONS

Hunter et al., "Modulation of crystal formation by bone phosphoproteins: structural specificity of the osteopontin-mediated inhibition of hydroxyapatite formation," Biochem J. 300:723-728 (1994).
Husain et al., "Fc site-specific labeling of immunoglobulins with calf intestinal alkaline phosphatase," Bioconjug Chem. 5(5):482-90 (1994).
Hwang et al., "Update of diagnostic evaluation of craniosynostosis with a focus on pediatric systematic evaluation and genetic studies," J Korean Neurosurg Soc. 59(3):214-8 (2016).
Ikezawa, "Glycosylphosphatidylinositol (GPI)-anchored proteins," Biol Pharm Bull. 25(4):409-17 (2002).
Inoue et al., "Four functionally distinct C-type natriuretic peptides found in fish reveal evolutionary history of the natriuretic peptide system," Proc Natl Acad Sci USA. 100(17):10079-10084 (2003).
International Preliminary Report on Patentability for International Patent Application No. PCT/CA2011/050258, mailed Nov. 15, 2012 (9 pages).
International Preliminary Report on Patentability for International Patent Application No. PCT/US2012/039004, issued Apr. 22, 2014 (8 pages).
International Preliminary Report on Patentability for International Patent Application No. PCT/US2012/060869, issued Apr. 22, 2014 (7 pages).
International Preliminary Report on Patentability for International Patent Application No. PCT/US2016/015366, mailed Aug. 10, 2017 (10 pages).
International Preliminary Report on Patentability for International Patent Application No. PCT/US2016/049983, issued Sep. 11, 2018 (9 pages).
International Search Report and Written Opinion for International Application No. PCT/US18/26868, mailed Sep. 7, 2018 (30 pages).
International Search Report and Written Opinion for International Patent Application No. PCT/CA2005/000615, mailed Aug. 18, 2005 (14 pages).
International Search Report and Written Opinion for International Patent Application No. PCT/CA2008/000923, mailed Sep. 12, 2008 (11 pages).
International Search Report and Written Opinion for International Patent Application No. PCT/CA2011/050258, mailed Jul. 29, 2011 (14 pages).
International Search Report and Written Opinion for International Patent Application No. PCT/CA2011/050807, mailed Apr. 13, 2012 (18 pages).
International Search Report and Written Opinion for International Patent Application No. PCT/US2012/039004, mailed Nov. 2, 2012 (22 pages).
International Search Report and Written Opinion for International Patent Application No. PCT/US2015/039973, mailed Oct. 5, 2015 (12 pages).
International Search Report and Written Opinion for International Patent Application No. PCT/US2015/058498, mailed Jan. 22, 2016 (12 pages).
International Search Report and Written Opinion for International Patent Application No. PCT/US2015/064003, mailed Mar. 31, 2016 (13 pages).
International Search Report and Written Opinion for International Patent Application No. PCT/US2016/015366, mailed Aug. 9, 2016 (14 pages).
International Search Report and Written Opinion for International Patent Application No. PCT/US2016/025721, mailed Aug. 17, 2016 (18 pages).
International Search Report and Written Opinion for International Patent Application No. PCT/US2016/039595, mailed Feb. 21, 2017 (16 pages).
International Search Report and Written Opinion for International Patent Application No. PCT/US2016/047166, mailed Nov. 7, 2016 (15 pages).
International Search Report and Written Opinion for International Patent Application No. PCT/US2016/049983, mailed Nov. 29, 2016 (12 pages).
International Search Report and Written Opinion for International Patent Application No. PCT/US2016/054013, mailed Dec. 13, 2016 (19 pages).
International Search Report and Written Opinion for International Patent Application No. PCT/US2017/025590, mailed Jun. 29, 2017 (18 pages).
International Search Report and Written Opinion for International Patent Application No. PCT/US2017/025618, mailed Jul. 11, 2017 (22 pages).
International Search Report and Written Opinion for International Patent Application No. PCT/US2017/036133, mailed Aug. 24, 2017 (10 pages).
International Search Report and Written Opinion for International Patent Application No. PCT/US2017/047527, mailed Nov. 6, 2017 (10 pages).
International Search Report and Written Opinion for International Patent Application No. PCT/US2018/020859, mailed Jun. 19, 2018 (14 pages).
International Search Report and Written Opinion for International Patent Application No. PCT/US2018/025206, mailed Jul. 3, 2018 (25 pages).
International Search Report for International Patent Application No. PCT/US2012/060869, mailed Mar. 25, 2013 (5 pages).
Invitation to Pay Additional Fees for International Patent Application No. PCT/CA2011/050807, mailed Feb. 13, 2012 (2 pages).
Invitation to Pay Additional Fees for International Patent Application No. PCT/US2012/039004, mailed Aug. 29, 2012 (2 pages).
Invitation to Pay Additional Fees for International Patent Application No. PCT/US2016/015366, mailed Jun. 1, 2016 (7 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Ishida et al., "Tissue-nonspecific alkaline phosphatase with an Asp(289)—>Val mutation fails to reach the cell surface and undergoes proteasome-mediated degradation," J Biochem. 134(1):63-70 (2003).
Jansonius, "Structure, evolution and action of vitamin $B_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Craniosynostosis," Eur J Hum Genet. 19(4):369-76 (2011).
Johnson et al., "Matrix vesicle plasma cell membrane glycoprotein-1 regulates mineralization by murine osteoblastic MC3T3 cells," J Bone Miner Res. 14(6):883-892 (1999).
Johnson et al., "Motor proficiency in children with neurofibromatosis type 1," Pediatr Phys Ther. 22(4):344-8 (2010).
Kabbani et al., "Craniosynostosis," Am Fam Physician. 69(12):2863-70 (2004).
Kajdic et al., "Craniosynostosis—Recognition, clinical characteristics, and treatment," Bosn J Basic Med Sci. 18(2):110-6 (2018).
Kakkis et al., "Enzyme-replacement therapy in mucopolysaccharidosis I," N Engl J Med. 344(3):182-8 (2001).
Kalra et al., "The role of C-type natriuretic peptide in cardiovascular medicine," Eur Heart J. 22:997-1007 (2001).
Kasugai et al., "Selective drug delivery system to bone: small peptide $(Asp)_6$ conjugation," J Bone Miner Res. 15(5):936-943 (2000).
Katsianou et al., "Signaling mechanisms implicated in cranial sutures pathophysiology: Craniosynostosis," BBA Clin. 6:165-76 (2016).
Kaufmann et al., "Influence of low temperature on productivity, proteome and protein phosphorylation of CHO cells," Biotechnol Bioeng. 63(5):573-82 (1999).
Khanna et al., "Pictorial essay: the many faces of craniosynostosis," Indian J Radiol Imaging. 21(1):49-56 (2011).
Kim et al., "Craniosynostosis: Updates in radiologic diagnosis," J Korean Neurosurg Soc. 59(3):219-26 (2016).

(56) References Cited

OTHER PUBLICATIONS

Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).

Kishnani et al., "Monitoring guidance for patients with hypophosphatasia treated with asfotase alfa," Mol Genet Metab. 122(1-2):4-17 (2017).

Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).

Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).

Kochendoerfer, "Protein & Peptide Drug Delivery—Third International Conference: Minimally invasive delivery methods, Sep. 22-23, Philadelphia, PA, USA," IDrugs. 6(11):1043-5 (2003).

Kosnik-Infinger et al., "Enzyme replacement therapy for congenital hypophosphatasia allows for surgical treatment of related complex craniosynostosis: a case series," Neurosurg Focus. 38(5):E10 (2015) (6 pages).

Kostenuik et al., "Infrequent delivery of a long-acting PTH-Fc fusion protein has potent anabolic effects on cortical and cancellous bone," J Bone Miner Res. 22(10):1534-1547 (2007).

Kozlowski et al., "Hypophosphatasia. Review of 24 Cases," Pediatr Radiol. 5(2):103-17 (1976) (15 pages).

Krakow et al., "Clinical and radiographic delineation of bent bone dysplasia-FGFR2 type or bent bone dysplasia with distinctive clavicles and angel-shaped phalanges," Am J Med Genet A. 170(10):2652-61 (2016).

Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).

Lazdunski et al., "Structure-function relationships for some metalloalkaline phosphatases of E. coli," Eur J Biochem. 8(4):510-7 (1969).

Le Du et al., "Crystal structure of alkaline phosphatase from human placenta at 1.8 Å resolution. Implication for a substrate specificity," J Biol Chem. 276(12):9158-65 (2001) (9 pages).

Lee et al., "Disturbed osteoblastic differentiation of fibrous hamartoma cell from congenital pseudarthrosis of the tibia associated with neurofibromatosis type I," Clin Orthop Surg. 3(3):230-7 (2011).

Leone et al., "Allosteric modulation of pyrophosphatase activity of rat osseous plate alkaline phosphatase by magnesium ions," Int J Biochem Cell Biol. 30:89-97 (1998).

Leung et al. "Outcome of perinatal hypophosphatasia in Manitoba Mennonites: a retrospective cohort analysis," JIMD Rep. 11:73-78 (2013).

Li et al., "Standard reference for the six-minute-walk test in healthy children aged 7 to 16 years," Am J Respir Crit Care Med. 176(2):174-80 (2007).

Linglart et al., "Hypophosphatasia," Curr Osteoporos Rep. 14(3):95-105; DOI 10.1007/s11914-016-0309-0 (2016) (11 pages).

Liu et al., "Tissue-nonspecific alkaline phosphatase deficiency causes abnormal craniofacial bone development in the Alpl(−/−) mouse model of infantile hypophosphatasia," available in PMC Oct. 1, 2015, published in final edited form as: Bone. 67:81-94 (2014) (30 pages).

Lo et al., "High level expression and secretion of Fc-X fusion proteins in mammalian cells," Protein Eng. 11(6):495-500 (1998).

López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).

Madson et al., "Asfotase alfa: sustained efficacy and tolerability in children with hypophosphatasia treated for 5 years," ESPE Abstracts. 84:FC2.4 (2015) (2 pages).

Mahmood et al., "Selection of the first-time dose in humans: comparison of different approaches based on interspecies scaling of clearance," J Clin Pharmacol. 43:692-697 (2003).

Makras et al., "Medical treatment of Hypercalcaemia," Hormones. 8(2):83-95 (2009).

Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).

Mather, "Establishment and characterization of two distinct mouse testicular epithelial cell lines," Biol Reprod. 23(1):243-52 (1980).

Mathijssen, "Guideline for care of patients with the diagnoses of craniosynostosis: working group on craniosynostosis," J Craniofac Surg. 26(6):1735-807 (2015).

Matsumoto et al., "Rescue of severe infantile hypophosphatasia mice by AAV-mediated sustained expression of soluble alkaline phosphatase," Hum Gene Ther. 22(11):1355-64 (2011).

Mayer, "Chapter 4: Immunoglobulins: Structure and Function," *Microbiology and Immunology On-line*, University of South Carolina School of Medicine, <pathmicro.med.sc.edu/mayer/IgStruct2000.htm> (2009) (12 pages).

McKiernan et al., "Clinical and radiographic findings in adults with persistent hypophosphatasemia," J Bone Miner Res. 29(7):1651-60 (2014).

Mericq et al., "Regulation of fetal rat bone growth by C-type natriuretic peptide and cGMP," Pediatr Res. 47(2):189-193 (2000) (9 pages).

Merrill et al., "Bent bone dysplasia-FGFR2 type, a distinct skeletal disorder, has deficient canonical FGF signaling," Am J Hum Genet. 90(3):550-7 (2012).

Meyer, "Can biological calcification occur in the presence of pyrophosphate?" Arch Biochem Biophys. 231(1):1-8 (1984).

Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).

Miller et al., "Ultrasound diagnosis of craniosynostosis," Cleft Palate Craniofac J. 39(1):73-80 (2002).

Millichap, "Cognitive Development of Children with Craniosynostosis," Pediatr Neurol Briefs. 29(6):47 (2015).

Millán et al., "Alkaline phosphatase and hypophosphatasia," Calcif Tissue Int. 98(4):398-416 (2016).

Millán et al., "Enzyme replacement therapy for murine hypophosphatasia," J Bone Miner Res. 23(6):777-87 (2008).

Millán et al., "Hypophosphatasia—pathophysiology and treatment," available in PMC Sep. 22, 2014, published in final edited form as: Actual Osteol. 8(3):164-182 (2012) (21 pages).

Millán, "The role of phosphatases in the initiation of skeletal mineralization," Calcif Tissue Int. 93(4):299-306 (2013).

Millán, Chapter 7: The in vivo role of TNAP. Mammalian alkaline phosphatases: From Biology to Applications in Medicine and Biotechnology. Wiley-VCH Verlag Gmbh & Co., 107-185 (2006).

Millán, *Mammalian Alkaline Phosphatases: From Biology to Applications in Medicine and Biotechnology*, Wiley-VCH Verlag Gmbh & Co., Weinheim, Germany (2006) (324 pages).

Miyazawa et al., "Cyclic GMP-dependent protein kinase II plays a critical role in C-type natriuretic peptide-mediated endochondral ossification," Endocrinology. 143(9):3604-3610 (2002).

Mohn et al., "Hypophosphatasia in a child with widened anterior fontanelle: lessons learned from late diagnosis and incorrect treatment," Acta Paediatr. 100(7):e43-6 (2011).

Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).

Mornet et al., "A molecular-based estimation of the prevalence of hypophosphatasia in the European population," Ann Hum Genet. 75(3):439-45 (2011).

Mornet et al., "Hypophosphatasia," GeneReviews. www.ncbi.nlm.gov/books/NBK1150/, retrieved Dec. 6, 2017, initially published Nov. 20, 2007, last updated Feb. 4, 2016 (25 pages).

(56) References Cited

OTHER PUBLICATIONS

Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Mornet et al., "Structural evidence for a functional role of human tissue nonspecific alkaline phosphatase in bone mineralization," J Biol Chem. 276(33):31171-8 (2001).
Mornet, "Hypophosphatasia," Best Pract Res Clin Rheumatol. 22(1):113-27 (2008).
Mornet, "Hypophosphatasia," Metabolism. 82:142-155; DOI: 10.1016/j.metabol.2017.08.013 (2018) (30 pages).
Mornet, "Hypophosphatasia," Orphanet J Rare Dis. 2:(40) (2007) (8 pages).
Mornet, "Chapter 2: Molecular genetics of hypophosphatasia and phenotype-genotype correlations," Subcell Biochem. 76:25-43 (2015).
Mornet, "The tissue nonspecific alkaline phosphatase gene mutations database," <www.sesep.uvsq.fr/03_hypo_mutations.php>, last updated Nov. 28, 2019 (14 pages).
Morris et al., "Immunolocalization of alkaline phosphatase in osteoblasts and matrix vesicles of human fetal bone," Bone Miner. 19:287-298 (1992).
Morrison et al. "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).
Morrow, "Expensive new biologic helps children fight hypophosphatasia," Manag Care. 24(12) (2015) (7 pages).
Moss et al., "Association of inorganic-pyrophosphatase activity with human alkaline-phosphatase preparations," Biochem J. 102:53-57 (1967).
Murgu et al. "Tracheobronchomalacia and excessive dynamic airway collapse," Respirology. 11(4):388-406 (2006).
Murray, "Lectin-specific targeting of lysosomal enzymes to reticuloendothelial cells," Methods Enzymol. 149:25-42 (1987).
Murshed et al., "Unique coexpression in osteoblasts of broadly expressed genes accounts for the spatial restriction of ECM mineralization to bone," Genes Dev. 19:1093-1104 (2005).
Nahabet et al., "Postnatal pancraniosynostosis in a patient with infantile hypophosphatasia," Cleft Palate Craniofac J. 53(6):741-4, doi: 10.1597/15-027 (2016).
Nakamura-Utsunomiya et al., "Clinical characteristics of perinatal lethal hypophosphatasia: a report of 6 cases," Clin Pediatr Endocrinol. 19(1):7-13 (2010).
Nakao et al., "The pharmacokinetics of alpha-human atrial natriuretic polypeptide in healthy subjects," Eur J Clin Pharmacol. 31(1):101-103 (1986).
Narisawa et al., "Abnormal vitamin B6 metabolism in alkaline phosphatase knock-out mice causes multiple abnormalities, but not the impaired bone mineralization," J Pathol. 193:125-133 (2001).
Narisawa et al., "Inactivation of two mouse alkaline phosphatase genes and establishment of a model of infantile hypophosphatasia," Dev Dyn. 208:432-446 (1997).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
National Institute for Health and Care Excellence, "Highly Specialised Technology Evaluation: Asfotase alfa for treating paediatric-onset hypophosphatasia [ID 758]," Oct. 21, 2015, <www.nice.org.uk/guidance/hst6/documents/committee-papers-8> (99 pages).
NCBI Protein Database Accession No. AAC33858, <www.ncbi.nlm.nih.gov/protei1653AC33858>, retrieved Apr. 16, 2013 (1 page).
NCBI Protein Database Accession No. AAF64516, <www.ncbi.nlm.nih.gov/protei1653AF64516>, retrieved Apr. 16, 2013 (2 pages).
NCBI Protein Database Accession No. AAH21289, <www.ncbi.nlm.nih.gov/protei1653AH21289>, retrieved Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI18209. Retrieved on Apr. 17, 2013 (2 pages).
NCBI Protein Database Accession No. AAI26166. Retrieved on Apr. 16, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798, Retrieved on Apr. 17, 2013 (2 pages).
NCBI Protein Database Accession No. NP_001622. Retrieved on Apr. 16, 2013 (3 pages).
NCBI Protein Database Accession No. NP_001623. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_112603. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09242. Retrieved on Apr. 16, 2013 (6 pages).
NCBI Protein Database Accession No. P09487. Retrieved on Apr. 16, 2013 (4 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q6PYX1. Retrieved on Oct. 15, 2013 (2 pages).
NCBI Protein Database Accession No. Q9N0V0. Retrieved on Apr. 16, 2013 (1 page).
NCBI Protein Database Accession No. XP_001109717. Retrieved on Apr. 17, 2013 (1 page).
Ngo et al., Chapter 14: Computational Complexity, Protein Structure Prediction, and the Levinthal Paradox. *The Protein Folding Problem and Tertiary Structure Prediction.* Merz et al. (eds.), 433, 492-495 (1994).
Nishioka et al., "Enhancement of drug delivery to bone: characterization of human tissue—nonspecific alkaline phosphatase tagged with an acidic oligopeptide," Mol Genet Metab. 88:244-255 (2006).
Nosjean et al., "Human tissue non-specific alkaline phosphatases: sugar-moiety-induced enzymic and antigenic modulations and genetic aspects," Biochem J. 321(Pt 2)(Pt 2):297-303 (1997).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Office Action for U.S. Appl. No. 11/111,664, mailed Dec. 4, 2008 (7 pages).
Office Action for U.S. Appl. No. 11/111,664, mailed May 14, 2008 (8 pages).

(56) References Cited

OTHER PUBLICATIONS

Office Action for U.S. Appl. No. 11/111,664, mailed Oct. 4, 2007 (11 pages).
Office Action for U.S. Appl. No. 11/484,870, mailed Aug. 11, 2009 (15 pages).
Office Action for U.S. Appl. No. 11/484,870, mailed Feb. 2, 2009 (16 pages).
Office Action for U.S. Appl. No. 11/484,870, mailed Jan. 25, 2007 (15 pages).
Office Action for U.S. Appl. No. 11/484,870, mailed Jul. 5, 2007 (13 pages).
Office Action for U.S. Appl. No. 11/484,870, mailed Jun. 25, 2008 (16 pages).
Office Action for U.S. Appl. No. 11/484,870, mailed Oct. 1, 2007 (12 pages).
Office Action for U.S. Appl. No. 12/405,920, mailed Aug. 9, 2010 (7 pages).
Office Action for U.S. Appl. No. 12/405,920, mailed Dec. 17, 2009 (14 pages).
Office Action for U.S. Appl. No. 12/793,517, mailed Aug. 16, 2010 (9 pages).
Office Action for U.S. Appl. No. 13/071,445, mailed Feb. 6, 2012 (12 pages).
Office Action for U.S. Appl. No. 13/071,445, mailed May 25, 2012 (14 pages).
Official Action and Translation for Japanese Application No. 2013-544989, mailed Oct. 27, 2015 (6 pages).
Official Action and Translation for Japanese Application No. 2017-539393, mailed Sep. 17, 2019 (14 pages).
Official Action for Russian Patent Application No. 2017123540, dated Jul. 8, 2019 (15 pages).
Official Notification and Search Report for Eurasian Patent Application No. 201291138, dated Jul. 16, 2013 (3 pages).
Oginni et al., "Radiological and biochemical resolution of nutritional rickets with calcium," Arch Dis Child. 88(9):812-17 (2003).
Oikawa et al., "Enzyme replacement therapy on hypophosphatasia mouse model," J Inherit Metab Dis. 37(2):309-17 (2013).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Opperman, "Cranial sutures as intramembranous bone growth sites," Dev Dyn. 219(4):472-85 (2000).
Orimo, "Pathophysiology of hypophosphatasia and the potential role of asfotase alfa," Ther Clin Risk Manag. 12:777-86 (2016).
Orimo, "The mechanism of mineralization and the role of alkaline phosphatase in health and disease," J Nippon Med Sch. 77(1):4-12 (2010).
Padidela et al., "Enzyme-replacement therapy in life-threatening perinatal hypophosphatasia in a premature infant," Endocrine Abstracts. 33:P9 (2013) (1 page).
Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).
Panesar, "Hypophosphatasia: a rare disorder," US Pharm. 42(5) (2017) (8 pages).
Park et al., "Ex vivo assessment of contractility, fatigability and alternans in isolated skeletal muscles," J Vis Exp. 69:e4198 (2012) (8 pages).
Park et al., "First Korean case of infantile hypophosphatasia with novel mutation in *ALPL* and literature review," Ann Clin Lab Sci. 46(3):302-7 (2016).
Patti et al., "Critical residues in the ligand-binding site of the *Staphylococcus aureus* collagen-binding adhesin (MSCRAMM)," J Biol Chem. 270(20):12005-11 (1995).
Pedersen et al., "Removal of N-terminal polyhistidine tags from recombinant proteins using engineered aminopeptidases," Protein Expr Purif. 15(3):389-400 (1999).
Pfeifer et al., "Intestinal secretory defects and dwarfism in mice lacking cGMP-dependent protein kinase II," Science. 274(5295):2082-2086 (1996).
Phillips et al., "A modified performance-oriented mobility assessment tool for assessing clinically relevant gait impairments and change in children with hypophosphatasia: development and validation," 7th International Conference on Children's Bone Health, Jun. 27-30, Salzburg, Austria. Bone Abstracts. 4:P136 (2015) (2 pages).
Phillips et al., "Gait assessment in children with childhood hypophosphatasia: impairments in muscle strength and physical function," The Endocrine Society's 97th Annual Meeting & Expo, Mar. 5-8, San Diego, California. Poster LBS-039 (2015) (2 pages).
Phillips et al., "Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, Mar. 5-8, San Diego, California. Poster Abstract FRI-224 (2015) (1 page).
Phillips et al., "Physical therapy management of infants and children with hypophosphatasia," Mol Genet Metab. 119(1-2):14-9 (2016).
Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).
Potter et al., "Natriuretic peptides, their receptors, and cyclic guanosine monophosphate-dependent signaling functions," Endocr Rev. 27(1):47-72 (2006).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Ratner, "Alexion pays big for Synageva's rare disease drug candidate," Nat Biotechnol. 33(7):679 (2015).
Reginato et al., "Musculoskeletal manifestations of osteomalacia and rickets," Best Pract Res Clin Rheumatol. 17(6):1063-80 (2003).
Remde et al., "Successful asfotase alfa treatment in an adult dialysis patient with childhood-onset hypophosphatasia," J Endoc Soc. 1(9):1188-93 (2017).
Reply Brief as Filed in U.S. Appl. No. 12/638,527, dated Apr. 22, 2016 (4 pages).
Reply to Final Office Action for U.S. Appl. No. 11/111,664, dated Sep. 10, 2008 (32 pages).
Reply to Final Office Action for U.S. Appl. No. 13/071,445, dated Oct. 25, 2012 (14 pages).
Restriction Requirement for U.S. Appl. No. 12/599,679, mailed Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Rockman-Greenberg, "Hypophosphatasia," Pediatr Endocrinol Rev. 10 Suppl 2:380-8 (2013) (Abstract only).
Rodgers et al., "Spring-assisted cranioplasty for the correction of non-syndromic scaphocephaly: a quantitative analysis of 100 consecutive cases," Plast Reconstr Surg. 140(1):125-34 (2017).
Rodriguez et al., "Respiratory mechanics in an infant with perinatal lethal hypophosphatasia treated with human recombinant enzyme replacement therapy," Pediatr Pulmonol. 47(9):917-22 (2012).
Rottgers et al., "Outcomes of endoscopic suturectomy with postoperative helmet therapy in bilateral coronal craniosynostosis," J Neurosurg Pediatr. 18(3):281-6 (2016).
Rowe et al., "MEPE, a new gene expressed in bone marrow and tumors causing osteomalacia," Genomics. 67:54-68 (2000).
Rozovsky et al., "Cranial ultrasound as a first-line imaging examination for craniosynostosis," Pediatrics. 137(2):e20152230 (2016) (9 pages).

(56) References Cited

OTHER PUBLICATIONS

Russell et al., "Inorganic pyrophosphate in plasma in normal persons and in patients with hypophosphatasia, osteogenesis imperfecta, and other disorders of bone," J Clin Invest. 50:961-969 (1971).
Sabbagh et al., "Hypophosphatemia leads to rickets by impairing caspase-mediated apoptosis of hypertrophic chondrocytes," Proc Natl Acad Sci U S A. 102(27):9637-42 (2005).
Saglam et al., "Clinical and genetic findings of Turkish hypophosphatasia cases," J Clin Res Pediatr Endocrinol. 9(3):229-236 (2017).
Sakamoto et al., "Physiological changes and clinical implications of syndromic craniosynostosis," J Korean Neurosurg Soc. 59(3):204-13 (2016).
Salih et al., "Identification of the phosphorylated sites of metabolically $^{32}$P-labeled osteopontin from cultured chicken osteoblasts," J Biol Chem. 272(21):13966-73 (1997).
Salva et al., "Signaling networks in joint development," Dev Dyn. 246(4):262-74 (2017).
Sands et al., "Enzyme replacement therapy for murine mucopolysaccharidosis type VII," J Clin Invest. 93(6):2324-31 (1994).
Saraff et al., "A diagnostic algorithm for children with low alkaline phosphatase activities: lessons learned from laboratory screening for hypophosphatasia," J Pediatr. 172:181-6 (2016) (7 pages).
Sather, "Case Study: 3 year old female with hypophosphatasia, treated with asfotase alfa replacement," J Pediatr Nurs. 34:104 (Abstract 008) (2017) (1 page).
Sawai et al., "Severe perinatal hypophosphatasia due to homozygous deletion of T at nucleotide 1559 in the tissue nonspecific alkaline phosphatase gene," Prenat Diagn. 23(9):743-6 (2003).
Schindeler et al., "Modeling bone morphogenetic protein and bisphosphonate combination therapy in wild-type and Nf1 haploinsufficient mice," J Orthop Res. 26(1):65-74 (2008).
Schmidt et al., "Clinical, radiographic and biochemical characteristics of adult hypophosphatasia," Osteoporos Int. 28(9):2653-2662 (2017).
Schmidt et al., "Hypophosphatasia: What is currently available for treatment?" Internist (Berl). 57(12):1145-1154 (2016) (Article in German) (English abstract).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL (1 page).
Sekido et al., "Novel drug delivery system to bone using acidic oligopeptide: pharmacokinetic characteristics and pharmacological potential," J Drug Target. 9(2):111-21 (2001).
Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140A(24):2794-6 (2006).
Shapiro et al., "Hypophosphatasia in adults: clinical assessment and treatment considerations," J Bone Miner Res. 32(10):1977-1980 (2017).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Sharom et al., "Glycosylphosphatidylinositol-anchored proteins: structure, function, and cleavage by phosphatidylinositol-specific phospholipase C," Biochem Cell Biol. 80:535-549 (2002).
Sheikh et al., "A newborn with no bones: neonatal hypophosphatasia with respiratory distress," J Pediatr. 188:306 (2017).
Shukla et al., "RNA interference and inhibition of MEK-ERK signaling prevent abnormal skeletal phenotypes in a mouse model of craniosynostosis," Nat Genet. 39(9):1145-1150 (2007).
Shull et al., "Enzyme replacement in a canine model of Hurler syndrome," Proc Natl Acad Sci USA. 91:12937-12941 (1994).
Siller et al., "Alkaline phosphatase: discovery and naming of our favorite enzyme," J Bone Miner Res. 33(2):362-4 (2018).
Silver et al., "Pulmonary hypoplasia in neonatal hypophosphatasia," Pediatr Pathol. 8(5):483-93 (1988) (12 pages).
Simm et al., "Successful use of enzyme replacement therapy in infantile hypophosphatasia," J Paediatr Child Health. 53(9):925-926 (2017).
Simmons, "Best Practices In: Recognizing and Diagnosing Hypophosphatasia," Clinical Endocrinology News. <www.mdedge.com/sites/default/files/issues/articles/Alexion_10_11_Final_Web.pdf>, published Sep. 30, 2013, retrieved on Mar. 27, 2019 (8 pages).
Siris et al., "Paget's disease of bone," Trends Endocrinol Metab. 2(6):207-12 (1991).
Skolnick et al., "From genes to protein structure and function: novel applications of computational approaches in the genomic era," Trends Biotechnol. 18(1):34-9 (2000).
Sotillo et al., "Signs and symptoms of hypophosphatasia," Dimensions of Dental Hygiene. 15(4):44-47 (2017) (6 pages).
Spears et al., "Deoxyuridylate effects on thymidylate synthase-5-fluorodeoxyuridylate-folate ternary complex formation," Biochem Pharmacol. 38(18):2985-2993 (1989).
Spentchian et al., "Severe hypophosphatasia: characterization of fifteen novel mutations in the ALPL gene," Hum Mutat. 22(1) (2003) (5 pages).
Srinivas et al., "Assessment of dose proportionality, absolute bioavailability, and immunogenicity response of CTLA4Ig (BMS-188667), a novel immunosuppressive agent, following subcutaneous and intravenous administration to rats," Pharm Res. 14(7): 911-6 (1997).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Stec et al., "A revised mechanism for the alkaline phosphatase reaction involving three metal ions," J Mol Biol. 299(5):1303-11 (2000).
Stoll et al., "Severe hypophosphatasia due to mutations in the tissue-nonspecific alkaline phosphatase (TNSALP) gene," Genet Couns. 13(3):289-95 (2002).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Suda et al., "C-type natriuretic peptide as an autocrine/paracrine regulator of osteoblast: evidence for possible presence of bone natriuretic peptide system," Biochem Biophys Res Commun. 223(1):1-6 (1996).
Sugano et al., "Successful gene therapy in utero for lethal murine hypophosphatasia," Hum Gene Ther. 23(4):399-406 (2012).
Supplementary European Search Report for European Application No. 05739065, mailed Dec. 2, 2008 (3 pages).
Supplementary European Search Report for European Application No. 08757088, dated Jun. 7, 2010 (5 pages).
Supplementary European Search Report for European Patent Application No. 11853820.6, mailed Mar. 25, 2014 (3 pages).
Symersky et al., "Structure of the collagen-binding domain from a *Staphylococcus aureus* adhesin," Nat Struct Biol. 4(10):833-838 (1997).
Takahashi et al., "Parental serum alkaline phosphatase activity as an auxiliary tool for prenatal diagnosis of hypophosphatasia," Prenat Diagn. 37(5):491-6 (2017).
Takano et al., "Molecular evolution of shark C-type natriuretic peptides," Zoolog Sci. 11(3):451-454 (1994).
Taketani et al., "Clinical and genetic aspects of hypophosphatasia in Japanese patients," Arch Dis Child. 99(3):211-5 (2014) (6 pages).
Taketani et al., "Ex vivo expanded allogeneic mesenchymal stem cells with bone marrow transplantation improved osteogenesis in infants with severe hypophosphatasia," Cell Transplant. 24(10):1931-43 (2015).
Taketani et al. Chapter 9: Hypophosphatasia. *Human Pathobiochemistry*. T. Oohashi et al. (eds.), 91-100 (2019).

(56) References Cited

OTHER PUBLICATIONS

Takinami et al., "The mutant (F310L and V365I) tissue-nonspecific alkaline phosphatase gene from hypophosphatasia," J Med Dent Sci. 51(1):67-74 (2004).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319(2):171-178 (2008).
Tenorio et al., "Molecular and clinical analysis of *ALPL* in a cohort of patients with suspicion of hypophosphatasia," Am J Med Genet A. 173(3):601-10 (2017).
Thacher et al., "Radiographic scoring method for the assessment of the severity of nutritional rickets," J Trop Pediatr. 46(3):132-9 (2000).
The Japanese Journal of Dermatology. 115(6): 843-7 (2005) (11 pages).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Tomatsu, Declaration Under 37 C.F.R. § 1.132 for U.S. Appl. No. 11/484,870, dated Jun. 1, 2009 (3 pages).
Tomatsu, Declaration Under 37 C.F.R. § 1.132 for U.S. Appl. No. 11/484,870, dated Nov. 27, 2007 (2 pages).
Tomazos et al., "Determination of the Minimal Clinically Important Difference in the Six-Minute Walk Test for Patients with Hypophosphatasia," 55th Annual European Society for Paediatric Endocrinology Meeting, Sep. 10-12, Paris, France. 86, Abstract FC2.5, <abstracts.eurospe.org/hrp/0086/hrp0086FC2.5.htm> (2016) (4 pages).
Tsiantouli et al., "Hypophosphatasia," Rev Med Suisse. 13(559):855-8 (2017) (Article in French) (English Abstract Included).
Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).
Tye et al., "Delineation of the hydroxyapatite-nucleating domains of bone sialoprotein," J Biol Chem. 278(10):7949-7955 (2003).
Uludag et al., "Bone affinity of a bisphosphonate-conjugated protein in vivo," Biotechnol Prog. 16(6):1115-8 (2000).
UniProtKB Accession No. P01857. Retrieved May 2, 2018 (13 pages).
UniProtKB Accession No. P05186. Retrieved May 2, 2018 (19 pages).
Urlaub et al., "Deletion of the diploid dihydrofolate reductase locus from cultured mammalian cells," Cell. 33(2):405-412 (1983).
Urlaub et al., "Isolation of Chinese hamster cell mutants deficient in dihydrofolate reductase activity," Proc Natl Acad Sci U S A. 77(7):4216-20 (1980).
Wang et al., "A mouse model for achondroplasia produced by targeting fibroblast growth factor receptor 3," Proc Natl Acad Sci USA. 96(8):4455-4460 (1999).
Wang et al., "Current concepts in odontohypophosphatasia form of hypophosphatasia and report of two cases," BMC Oral Health. 16(1):70 (2016) (8 pages).
Wang et al., "Mice lacking Nf1 in osteochondroprogenitor cells display skeletal dysplasia similar to patients with neurofibromatosis type 1," Hum Mol Genet. 20(20):3910-3924 (2011).
Wang et al., "Structure-based chemical modification strategy for enzyme replacement treatment of phenylketonuria," Mol Genet Metab. 86(1-2):134-140 (2005).
Watanabe et al., "Prevalence of c. 1559delT in *ALPL*, a common mutation resulting in the perinatal (lethal) form of hypophosphatasia in Japanese and effects of the mutation on heterozygous carriers," J Hum Genet. 56(2):166-8 (2011).
Waymire et al., "Mice lacking tissue non-specific alkaline phosphatase die from seizures due to defective metabolism of vitamin B-6," Nat Genet. 11(1):45-51 (1995).

Weber et al., "Burden of disease in adult patients with hypophosphatasia: Results from two patient-reported surveys," Metabolism. 65(10):1522-30 (2016).
Weber et al., "Burden of disease in children with hypophosphatasia: results from patient-reported surveys," 7th International Conference on Children's Bone Health, Jun. 27-30, Salzburg, Austria. *Bone Abstracts*. 4: P119 (2015) (3 pages).
Weinberg, "An overview of infliximab, etanercept, efalizumab, and alefacept as biologic therapy for psoriasis," Clin Ther. 25(10):2487-505 (2003).
Weiss et al., "A missense mutation in the human liver/bone/kidney alkaline phosphatase gene causing a lethal form of hypophosphatasia," Proc Natl Acad Sci USA. 85(20):7666-7669 (1988).
Weiss et al., "Isolation and characterization of a cDNA encoding a human liver/bone/kidney-type alkaline phosphatase," Proc Natl Acad Sci USA. 83(19):7182-6 (1986) (6 pages).
Weiss et al., "Structure of the human liver/bone/kidney alkaline phosphatase gene," J Biol Chem. 263(24):12002-10 (1988).
Weninger et al., "Biochemical and morphological effects of human hepatic alkaline phosphatase in a neonate with hypophosphatasia," Acta Paediatr Scand. Suppl. 360:154-160 (1989).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Whyte et al., "Adult hypophosphatasia treated with teriparatide," J Clin Endocrinol Metab. 92(4):1203-8 (2007).
Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).
Whyte et al. "Asfotase alfa for infants and young children with hypophosphatasia: 7 year outcomes of a single-arm, open-label, phase 2 extension trial," Lancet Diabetes Endocrinol. 7(2):93-105 (2019) (52 pages).
Whyte et al., "Asfotase alfa therapy for children with hypophosphatasia," JCI Insight. 1(9):e85971 (2016) (11 pages).
Whyte et al., "Asfotase alfa treatment improves survival for perinatal and infantile hypophosphatasia," J Clin Endocrinol Metab. 101(1):334-42 (2016) (17 pages).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).
Whyte et al., "Enzyme-replacement therapy in life-threatening hypophosphatasia," N Engl J Med. 366(10):904-13 (2012).
Whyte et al., "Hypophosphatasia (HPP) in children: enzyme replacement therapy (EzRT) using bone-targeted, tissue-nonspecific alkaline phosphatase (TNSALP)," Ann Neurol. 68(Suppl 14):S70 Abstract WIP-28 (2010) (1 page).
Whyte et al., "Hypophosphatasia: A Retrospective Natural History Study of the Severe Perinatal and Infantile Forms," 2014 European Calcified Tissue Society Congress, May 17-20, Prague, Czech Republic. Poster P364 (2014) (1 page).
Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012) (1 page).
Whyte et al., "Hypophosphatasia: natural history study of 101 affected children investigated at one research center," Bone. 93:125-138 (2016).
Whyte et al., "Hypophosphatasia: validation and expansion of the clinical nosology for children from 25 years experience with 173 pediatric patients," Bone. 75:229-39 (2015).

(56) References Cited

OTHER PUBLICATIONS

Whyte et al., "Infantile hypophosphatasia: enzyme replacement therapy by intravenous infusion of alkaline phosphatase-rich plasma from patients with Paget bone disease," J Pediatr. 101(3):379-86 (1982).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Whyte et al., "Markedly increased circulating pyridoxal-5'-phosphate levels in hypophosphatasia," J Clin Invest. 76(2):752-756 (1985).
Whyte et al., "Marrow cell transplantation for infantile hypophosphatasia," J Bone Miner Res. 18(4):624-36 (2003).
Whyte et al. "Natural history of perinatal and infantile hypophosphatasia: a retrospective study," J Pediatr. 209:116-124.e4 (2019) (13 pages).
Whyte et al., "Rickets and osteomalacia," Medicine. 37(9):483-8 (2009).
Whyte, "Chapter 70: Hypophosphatasia: Nature's window on alkaline phosphatase function in man," *Principles of Bone Biology, 2nd ed.*, Bilezikian, Raisz, and Rodan. 2:1229-1248 (2002).
Whyte, "Hypophosphatasia—aetiology, nosology, pathogenesis, diagnosis and treatment," Nat Rev Endocrinol. 12(4):233-46 (2016).
Whyte, "Hypophosphatasia and the role of alkaline phosphatase in skeletal mineralization," Endocr Rev. 15(4):439-461 (1994).
Whyte, "Hypophosphatasia," in The Metabolic and Molecular Bases of Inherited Disease (8th ed.), pp. 5313-5329, 2001 (McGraw-Hill Book Company) (epub pp. 1-41).
Whyte, "Hypophosphatasia: an overview for 2017," Bone. 102:15-25 (2017).
Whyte, "Hypophosphatasia: enzyme replacement therapy brings new opportunities and new challenges," J Bone Miner Res. 32(4):667-675 (2017).
Whyte, "Physiological role of alkaline phosphatase explored in hypophosphatasia," Ann N Y Acad Sci. 1192:190-200 (2010).
Whyte, Chapter 18: Heritable Forms of Rickets and Osteomalacia. *Connective Tissue and Its Heritable Disorders*. Wiley-Liss, Inc., eds. R.M. Royce and B. Steinmann, 765-87 (2002).
Whyte, Chapter 207: Hypophosphatasia. *The Online Metabolic and Molecular Bases for Inherited Disease*. McGraw-Hill Book Company, Valle et al. (eds.) (2001) (41 pages).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Whyte, Chapter 73: Hypophosphatasia: Nature's Window on Alkaline Phosphatase Function in Humans, *Principles of Bone Biology, vol. 1, Third Edition*. John P. Bilezikian, Lawrence G. Raisz and T. John Martin (eds.), 1573-98 (2008).
Wickramasinghe et al., "A case of hypophosphatasia," Ceylon Med J. 48(3):94-5 (2003) (2 pages).
Williams et al., "Solute transport in growth plate cartilage: In vitro and in vivo," Biophys J. 93(3):1039-1050 (2007).
Wroblewski et al., "Pharmacokinetics, metabolic stability, and subcutaneous bioavailability of a genetically engineered analog of DcR3, Flint [DcR3(R218Q)], in cynomolgus monkeys and mice," Drug Metab Dispos. 31(4):502-507 (2003).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yamamoto et al., "A successful treatment with pyridoxal phosphate for West syndrome in hypophosphatasia," Pediatr Neurol. 30(3):216-8 (2004).
Yamamoto et al., "Long term phenotypic correction of severe infantile hypophosphatasia in a mouse model by neonatal injection of lentiviral vector," Mol Ther. 17:S67-S68, Abstract 171 (2009) (2 pages).
Yamamoto et al., "Prolonged survival and phenotypic correction of Akp2$^{-/-}$hypophosphatasia mice by lentiviral gene therapy," J Bone Miner Res. 26(1):135-42 (2011).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Overexpression of CNP in chondrocytes rescues achondroplasia through a MAPK-dependent pathway," Nat Med. 10(1):80-86 (2004).
Yasoda et al., "Systemic administration of C-type natriuretic peptide as a novel therapeutic strategy for skeletal dysplasias," Endocrinology. 150(7):3138-3144 (2009).
Yoder et al., "Reduced ability of C-type natriuretic peptide (CNP) to activate natriuretic peptide receptor B (NPR-B) causes dwarfism in lbab$^{-/-}$mice," Peptides. 29(9):1575-1581 (2008).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
Zaleckas et al., "Diagnosis and treatment of craniosynostosis: Vilnius team experience," Acta Med Litu. 22(2):111-21 (2015).
Zierhut et al., "Population PK-PD model for Fc-osteoprotegerin in healthy postmenopausal women," J Pharmacokinet Pharmacodyn. 35(4):379-399 (2008).
Zurutuza et al., "Correlations of genotype and phenotype in hypophosphatasia," Hum Mol Genet. 8(6):1039-1046 (1999).
Park et al. "The effect of alendronate loaded biphasic calcium phosphate scaffolds on bone regeneration in a rat tibial defect model," Int J Mol Sci. 16(11):26738-53 (2015) (17 pages).
Li et al. "Timing of the initiation of bisphosphonates after surgery for fracture healing: a systematic review and meta-analysis of randomized controlled trials," Osteoporos Int. 26(2):431-41 (2015) (11 pages).
International Search Report and Written Opinion for International Application No. PCT/US2019/045963, mailed Jan. 30, 2020 (26 pages).
Search Report and Translation for Russian Application No. 2018109368, dated Feb. 5, 2020 (4 pages).
Wang et al. "The effects of tissue-non-specific alkaline phosphatase gene therapy on craniosynostosis and craniofacial morphology in the FGFR2$^{C342Y/+}$mouse model of Crouzon craniosynostosis," Orthod Craniofac Res. 18 Suppl. 1(01):196-206 (2015).
Abrams et al., "Calcium and Vitamin D Requirements of Enterally Fed Preterm Infants," Pediatrics. 131(5):e1676-e1683 (2013) (9 pages).
Kishnani et al., "Hypophosphatasia: enzyme replacement therapy (ENB-0040) decreases TNSALP substrate accumulation and improves functional outcome in affected adolescents and adults," Endocrine Society's 15th International & 14th European Congress of Endocrinology, May 5-9, Florence, Italy. Abstract OC8.1 (2012) (4 pages).
Office Action for Japanese Application No. 2018-508754, mailed Jun. 30, 2020 (11 pages).
Phillips et al., "Gait Assessment in Children with Childhood Hypophosphatasia: Impairments in Muscle Strength and Physical Function," The Endocrine Society's 97th Annual Meeting & Expo, Mar. 5-8, San Diego, CA. (2017) (2 pages).
Office Action for European Patent Application No. 16739617.5, dated May 11, 2020 (10 pages).
Rodionova et al., "Hypophosphatasia in Adults: Clinical Cases and Literature Review," Osteoporosis and Bone Diseases. 18(2):25-28 (2015) 10.14341/osteo2015225-28 (English language abstract).
Office Action for Russian Patent Application No. 2018137822, mailed Jul. 24, 2020 (20 pages).
Office Action for Russian Application No. 2018137822, mailed Jul. 24, 2020 (9 pages). Rodionova, S & Zakharova, E & Buklemishev, Yu & Khakimov, U & Lapkina, S. (2015). Hypophosphatasia in Adults: Clinical Cases and Literature Review. Osteoporosis and Bone Diseases. 18. 25-28. 10.14341/osteo2015225-28.
Bishop et al., "Life-threatening hypophosphatasia (HPP): Results of up to two years bone-targeted Enzyme Replacement Therapy (ERT) in infants and young children," Bone. 48:S82 (2011).

(56) References Cited

OTHER PUBLICATIONS

Little et al., "Lineage tracking of myogenic progenitors in surgical models of tibial bone repair," Bone. 48(2):S82 (2011).
Whyte et al., "Treatment of children with hypophosphatasia (HPP) with ENB-0040: radiographic and DXA outcomes after 6 months of therapy," Horm Res Paediatr. 76(Suppl 2):26 (2011).
Kim et al., "Comparison of phenylketonuria (PKU) patients' height, weight and body mass index (BMI) to the general population," Molecular Genetics and Metabolism. 105:328-329 (2012).
Office Action for Japanese Patent Application No. 2018-515934, mailed Jul. 28, 2020 (7 pages).
Sequencia—"Bone targeted alkaline phosphatase, kits and methods of use thereof," UniParc, (20101102), Database No. HI520929 (1 page), Nov. 2, 2010.
Seefried et al., "Real-world Clinical Profiles of Adults with Hypophosphatasia (HPP) from the Global HPP Registry," The American Society for Bone and Mineral Research 2020 Annual Meeting, Sep. 11-15, virtually (2020).
Seefried et al., "Bone Turnover and Mineral Metabolism in Adult Patients with Pediatric-Onset Hypophosphatasia Treated With Asfotase Alfa," The American Society for Bone and Mineral Research 2020 Annual Meeting, Sep. 11-15, virtually (2020).
Seefried et al., "Long-term Effectiveness of Asfotase Alfa Treatment in Adults with Pediatric-onset Hypophosphatasia in Routine Clinical Practice" 22nd European Congress of Endocrinology, Sep. 5-9, virtual (2020).
Anonymous: "Scale-up of CHO fed-batch cultures in HyClone (TM) ActiPro (TM) medium supplemented with Cell Boost (TM) 7a and 7b," Oct. 11, 2016, pp. 1-4, XP055461185.
Fu-Hang et al., "Preliminary study on the effect of Zn2+ on the activities of peptidase and alkaline phosphatase," Marine Sciences. 27(3):64-65 (2003).
Office Action for Chinese Patent Application No. 201680048588.5, mailed Jan. 18, 2021 (13 pages).
Miller et al., "Genetic diversity and population structure of the endangered marsupial *Sarcophilus harrisii* (Tasmanian devil)," Proc Natl Acad Sci U S A. 108(30):12348-53 (Jul. 2011).
Partial Supplementary European Search Report for European Application No. 20898477.3, dated Dec. 6, 2023 (25 pages).
Alonso et al., "Loss-of-Function Mutations in the ALPL Gene Presenting with Adult Onset Osteoporosis and Low Serum Concentrations of Total Alkaline Phosphatase," J Bone Miner Res. 35(4):657-661 (Apr. 2021).
Rodriguez et al., "A Novel Mutation in ALPL Gene Causing Adult Autosomal Dominant Hypophosphatasia in a Family of Southern Spain: Phenotype Characterization," Ann Rheum Dis. 82:428-9 (May 2023).
UniProtKB Accession No. G3WYY8. Retrieved Nov. 16, 2011 (4 pages).
Official Action for Japanese Application No. 2021-506690, dated Nov. 7, 2023 (10 pages).
International Search Report and Written Opinion for International Patent Application No. PCT/US2021/055991, mailed Jan. 25, 2022 (8 pages).
Official Action for Eurasian Application No. 202391228, dated Dec. 13, 2023 (5 pages).
Oguchi et al., "Control of Temperature and pH Enhances Human Monoclonal Antibody Production in CHO Cell Culture," Animal Cell Technology: Basic and Applied Aspects. Springer/Dordrecht. 13:169-172 (Jan. 2003).
Koumpouras et al., "Dynamic Optimization of Bioprocesses," Applied Mathematics. 3(10A):1487-1495 (Oct. 2012).
"Common Drug Review: Pharmacoeconomic Review Report for asfotase alfa (Strensiq)," Canadian Agency for Drugs and Technologies in Health (Apr. 2017) (25 pages).
Office Action for Eurasian Application No. 202390771/28, dated Jan. 16, 2024 (3 pages).
Examination Report for Australian Application No. 2021337652, dated Feb. 28, 2024 (5 pages).
Sutton et al., "'Atypical femoral fractures' during bisphosphonate exposure in adult hypophosphatasia" J Bone Miner Res. 27(5):987-94 (May 2012).
Office Action for Canadian Patent Application No. 3,173,631, dated Jan. 26, 2024 (5 pages).
"STIC search of SEQ ID No. 1," U.S. Appl. No. 13/899,359, filed May 21, 2013, dated Feb. 22, 2024 (2 pages).
"Alkaline phosphatase, tissue-nonspecific isozyme [Galeopterus variegatus]," GenBank, accession No. XP_008584004, accessed Jul. 22, 2014, (2 pages).
"Alkaline phosphatase, tissue-nonspecific isozyme isoform X3 [Erinaceus europaeus]," GenBank, accession No. XP_016048561, accessed Apr. 11, 2016, (2 pages).
Office Action for Canadian Patent Application No. 3,161,266, dated Feb. 14, 2024 (4 pages).
International Search Report and Written Opinion for International Patent Application No. PCT/US2021/048792, mailed Dec. 23, 2021 (11 pages).

\* cited by examiner

SEQUENCE LISTING

```
<160> NUMBER OF SEQ ID NOS: 20

<210> SEQ ID NO 1
<211> LENGTH: 726
<212> TYPE: PRT
<213> ORGANISM: Artificial Sequence
```

<220> FEATURE:
<223> OTHER INFORMATION: Synthetic Construct

<400> SEQUENCE: 1

```
Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
    130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Asn Lys Thr Asp Val Glu Tyr Glu Ser Asp Glu Lys
    210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
        275                 280                 285

Asp Pro Ser Leu Ser Glu Met Val Val Val Ala Ile Gln Ile Leu Arg
    290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
        355                 360                 365

Gly Gly Tyr Thr Pro Arg Gly Asn Ser Ile Phe Gly Leu Ala Pro Met
    370                 375                 380

Leu Ser Asp Thr Asp Lys Lys Pro Phe Thr Ala Ile Leu Tyr Gly Asn
385                 390                 395                 400
```

```
Gly Pro Gly Tyr Lys Val Val Gly Glu Arg Glu Asn Val Ser Met
            405                 410                 415

Val Asp Tyr Ala His Asn Asn Tyr Gln Ala Gln Ser Ala Val Pro Leu
            420                 425                 430

Arg His Glu Thr His Gly Gly Glu Asp Val Ala Val Phe Ser Lys Gly
            435                 440                 445

Pro Met Ala His Leu Leu His Gly Val His Glu Gln Asn Tyr Val Pro
        450                 455                 460

His Val Met Ala Tyr Ala Ala Cys Ile Gly Ala Asn Leu Gly His Cys
465                 470                 475                 480

Ala Pro Ala Ser Ser Leu Lys Asp Lys Thr His Thr Cys Pro Pro Cys
                485                 490                 495

Pro Ala Pro Glu Leu Leu Gly Gly Pro Ser Val Phe Leu Phe Pro Pro
                500                 505                 510

Lys Pro Lys Asp Thr Leu Met Ile Ser Arg Thr Pro Glu Val Thr Cys
            515                 520                 525

Val Val Val Asp Val Ser His Glu Asp Pro Glu Val Lys Phe Asn Trp
        530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
        595                 600                 605

Gln Pro Arg Glu Pro Gln Val Tyr Thr Leu Pro Pro Ser Arg Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
        675                 680                 685

Val Phe Ser Cys Ser Val Met His Glu Ala Leu His Asn His Tyr Thr
    690                 695                 700

Gln Lys Ser Leu Ser Leu Ser Pro Gly Lys Asp Ile Asp Asp Asp Asp
705                 710                 715                 720

Asp Asp Asp Asp Asp
                725

<210> SEQ ID NO 2
<211> LENGTH: 524
<212> TYPE: PRT
<213> ORGANISM: Homo sapiens

<400> SEQUENCE: 2

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
```

```
            35                  40                  45
Asn Val Ala Lys Asn Val Ile Met Phe Leu Gly Asp Gly Met Gly Val
 50                  55                  60

Ser Thr Val Thr Ala Ala Arg Ile Leu Lys Gly Gln Leu His His Asn
 65                  70                  75                  80

Pro Gly Glu Glu Thr Arg Leu Glu Met Asp Lys Phe Pro Phe Val Ala
                     85                  90                  95

Leu Ser Lys Thr Tyr Asn Thr Asn Ala Gln Val Pro Asp Ser Ala Gly
                    100                 105                 110

Thr Ala Thr Ala Tyr Leu Cys Gly Val Lys Ala Asn Glu Gly Thr Val
                115                 120                 125

Gly Val Ser Ala Ala Thr Glu Arg Ser Arg Cys Asn Thr Thr Gln Gly
            130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                    165                 170                 175

Ala Tyr Ala His Ser Ala Asp Arg Asp Trp Tyr Ser Asp Asn Glu Met
                180                 185                 190

Pro Pro Glu Ala Leu Ser Gln Gly Cys Lys Asp Ile Ala Tyr Gln Leu
                195                 200                 205

Met His Asn Ile Arg Asp Ile Asp Val Ile Met Gly Gly Gly Arg Lys
                210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                    245                 250                 255

Lys Ser Phe Lys Pro Arg Tyr Lys His Ser His Phe Ile Trp Asn Arg
                260                 265                 270

Thr Glu Leu Leu Thr Leu Asp Pro His Asn Val Asp Tyr Leu Leu Gly
                275                 280                 285

Leu Phe Glu Pro Gly Asp Met Gln Tyr Glu Leu Asn Arg Asn Asn Val
            290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                    325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
                355                 360                 365

Glu Asp Thr Leu Thr Val Val Thr Ala Asp His Ser His Val Phe Thr
                370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                    405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
                435                 440                 445

Leu Arg His Glu Thr His Gly Gly Glu Asp Val Ala Val Phe Ser Lys
                450                 455                 460
```

```
Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 3
<211> LENGTH: 524
<212> TYPE: PRT
<213> ORGANISM: Homo sapiens

<400> SEQUENCE: 3

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg His Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Val Ala Ile Gln Ile Leu
```

```
            305                 310                 315                 320
    Arg Lys Asn Pro Lys Gly Phe Leu Leu Val Glu Gly Arg Ile
                    325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
                355                 360                 365

Glu Asp Thr Leu Thr Val Val Thr Ala Asp His Ser His Val Phe Thr
        370                 375                 380

Phe Gly Gly Tyr Thr Pro Arg Gly Asn Ser Ile Phe Gly Leu Ala Pro
    385                 390                 395                 400

Met Leu Ser Asp Thr Asp Lys Lys Pro Phe Thr Ala Ile Leu Tyr Gly
                    405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
    465                 470                 475                 480

Pro His Val Met Ala Tyr Ala Ala Cys Ile Gly Ala Asn Leu Gly His
                    485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 4
<211> LENGTH: 524
<212> TYPE: PRT
<213> ORGANISM: Homo sapiens

<400> SEQUENCE: 4

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
                20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160
```

-continued

Val Gly Ile Val Thr Thr Thr Arg Val Asn His Ala Thr Pro Ser Ala
            165                 170                 175

Ala Tyr Ala His Ser Ala Asp Arg Asp Trp Tyr Ser Asp Asn Glu Met
        180                 185                 190

Pro Pro Glu Ala Leu Ser Gln Gly Cys Lys Asp Ile Ala Tyr Gln Leu
            195                 200                 205

Met His Asn Ile Arg Asp Ile Asp Val Ile Met Gly Gly Arg Lys
        210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
        290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
        515                 520

<210> SEQ ID NO 5
<211> LENGTH: 524
<212> TYPE: PRT
<213> ORGANISM: Homo sapiens

<400> SEQUENCE: 5

Met Ile Ser Pro Phe Leu Val Leu Ala Ile Gly Thr Cys Leu Thr Asn
1               5                   10                  15

```
Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
 50                  55                  60

Ser Thr Val Thr Ala Ala Arg Ile Leu Lys Gly Gln Leu His His Asn
 65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430
```

```
Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 6
<211> LENGTH: 524
<212> TYPE: PRT
<213> ORGANISM: Homo sapiens

<400> SEQUENCE: 6

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg His Lys His Ser His Phe Ile Trp Asn Arg
            260                 265                 270

Thr Glu Leu Leu Thr Leu Asp Pro His Asn Val Asp Tyr Leu Leu Gly
        275                 280                 285
```

Leu Phe Glu Pro Gly Asp Met Gln Tyr Glu Leu Asn Arg Asn Asn Val
            290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
            370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
            450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 7
<211> LENGTH: 652
<212> TYPE: PRT
<213> ORGANISM: Macaca mulatta

<400> SEQUENCE: 7

Met Pro Thr Val Lys Thr Lys Gln Glu Ser His Ala Gly Ser Gly Ser
1               5                   10                  15

Gly Pro Arg Leu Ala Glu Arg Lys Gly Arg Val Gly Ala Ala Arg Arg
            20                  25                  30

Gln Ser Pro Arg Ala Pro Gly Gly Leu Pro Gly Pro Arg Ser Gly
            35                  40                  45

Pro Ala Ala Ala Phe Ile Arg Arg Arg Gly Arg Trp Pro Gly Pro Arg
50                  55                  60

Cys Ala Pro Ala Thr Pro Arg Pro Arg Ser Arg Leu Cys Ala Pro Thr
65                  70                  75                  80

Arg Leu Cys Leu Asp Glu Pro Ser Ser Val Leu Cys Ala Gly Leu Glu
                85                  90                  95

His Gln Leu Thr Ser Asp His Cys Gln Pro Thr Pro Ser His Pro Arg
                100                 105                 110

Arg Ser His Leu Trp Ala Ser Gly Ile Lys Gln Val Leu Gly Cys Thr
            115                 120                 125

Met Ile Ser Pro Phe Leu Val Leu Ala Ile Gly Thr Cys Leu Thr Asn

-continued

```
            130                 135                 140
Ser Leu Val Pro Glu Lys Glu Lys Asp Pro Lys Tyr Trp Arg Asp Gln
145                 150                 155                 160

Ala Gln Glu Thr Leu Lys Tyr Ala Leu Glu Leu Gln Lys Leu Asn Thr
                165                 170                 175

Asn Val Ala Lys Asn Val Ile Met Phe Leu Gly Asp Gly Met Gly Val
                180                 185                 190

Ser Thr Val Thr Ala Thr Arg Ile Leu Lys Gly Gln Leu His His Asn
                195                 200                 205

Pro Gly Glu Glu Thr Arg Leu Glu Met Asp Lys Phe Pro Phe Val Ala
210                 215                 220

Leu Ser Lys Thr Tyr Asn Thr Asn Ala Gln Val Pro Asp Ser Ala Gly
225                 230                 235                 240

Thr Ala Thr Ala Tyr Leu Cys Gly Val Lys Ala Asn Glu Gly Thr Val
                245                 250                 255

Gly Val Ser Ala Ala Thr Glu Arg Ser Arg Cys Asn Thr Thr Gln Gly
                260                 265                 270

Asn Glu Val Thr Ser Ile Leu Arg Trp Ala Lys Asp Ala Gly Lys Ser
                275                 280                 285

Val Gly Ile Val Thr Thr Thr Arg Val Asn His Ala Thr Pro Ser Ala
290                 295                 300

Ala Tyr Ala His Ser Ala Asp Arg Asp Trp Tyr Ser Asp Asn Glu Met
305                 310                 315                 320

Pro Pro Glu Ala Leu Ser Gln Gly Cys Lys Asp Ile Ala Tyr Gln Leu
                325                 330                 335

Val His Asn Ile Arg Asp Ile Asp Val Ile Met Gly Gly Gly Arg Lys
                340                 345                 350

Tyr Met Tyr Pro Lys Asn Lys Thr Asp Val Glu Tyr Glu Ile Asp Glu
                355                 360                 365

Lys Ala Arg Gly Thr Arg Leu Asp Gly Leu Asp Leu Val Asn Ile Trp
370                 375                 380

Lys Ser Phe Lys Pro Arg His Lys His Ser His Phe Ile Trp Asn Arg
385                 390                 395                 400

Thr Glu Leu Leu Thr Leu Asp Pro His Asn Val Asp Tyr Leu Leu Gly
                405                 410                 415

Leu Phe Glu Pro Gly Asp Met Glu Tyr Glu Leu Asn Arg Asn Asn Val
                420                 425                 430

Thr Asp Pro Ser Leu Ser Glu Met Val Val Ala Ile Gln Ile Leu
                435                 440                 445

Arg Lys Asn Pro Lys Gly Phe Phe Leu Leu Val Glu Gly Gly Arg Ile
450                 455                 460

Asp His Gly His His Glu Gly Lys Ala Lys Gln Ala Leu His Glu Ala
465                 470                 475                 480

Val Glu Met Asp Arg Ala Ile Gly Gln Ala Gly Ser Met Thr Ser Leu
                485                 490                 495

Glu Asp Thr Leu Thr Val Val Thr Ala Asp His Ser His Val Phe Thr
                500                 505                 510

Phe Gly Gly Tyr Thr Pro Arg Gly Asn Ser Ile Phe Gly Leu Ala Pro
                515                 520                 525

Met Leu Ser Asp Thr Asp Lys Lys Pro Phe Thr Ala Ile Leu Tyr Gly
                530                 535                 540

Asn Gly Pro Gly Tyr Lys Val Val Gly Gly Glu Arg Glu Asn Val Ser
545                 550                 555                 560
```

```
Met Val Asp Tyr Ala His Asn Asn Tyr Gln Ala Gln Ser Ala Val Pro
            565                 570                 575

Leu Arg His Glu Thr His Gly Gly Glu Asp Val Ala Val Phe Ser Lys
            580                 585                 590

Gly Pro Met Ala His Leu Leu His Gly Val His Glu Gln Asn Tyr Ile
            595                 600                 605

Pro His Val Met Ala Tyr Ala Ala Cys Ile Gly Ala Asn Leu Asp His
            610                 615                 620

Cys Ala Pro Ala Ser Ser Ala Gly Ser Leu Ala Ala Gly Pro Leu Leu
625                 630                 635                 640

Leu Pro Leu Ala Leu Phe Pro Leu Ser Ile Leu Phe
            645                 650

<210> SEQ ID NO 8
<211> LENGTH: 524
<212> TYPE: PRT
<213> ORGANISM: Rattus norvegicus

<400> SEQUENCE: 8

Met Ile Leu Pro Phe Leu Val Leu Ala Ile Gly Pro Cys Leu Thr Asn
1               5                   10                  15

Ser Phe Val Pro Glu Lys Glu Lys Asp Pro Ser Tyr Trp Arg Gln Gln
            20                  25                  30

Ala Gln Glu Thr Leu Lys Asn Ala Leu Lys Leu Gln Lys Leu Asn Thr
            35                  40                  45

Asn Val Ala Lys Asn Ile Ile Met Phe Leu Gly Asp Gly Met Gly Val
        50                  55                  60

Ser Thr Val Thr Ala Ala Arg Ile Leu Lys Gly Gln Leu His His Asn
65                  70                  75                  80

Thr Gly Glu Glu Thr Arg Leu Glu Met Asp Lys Phe Pro Phe Val Ala
            85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
            115                 120                 125

Gly Val Ser Ala Ala Thr Glu Arg Thr Arg Cys Asn Thr Thr Gln Gly
            130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
            165                 170                 175

Ala Tyr Ala His Ser Ala Asp Arg Asp Trp Tyr Ser Asp Asn Glu Met
            180                 185                 190

Arg Pro Glu Ala Leu Ser Gln Gly Cys Lys Asp Ile Ala Tyr Gln Leu
            195                 200                 205

Met His Asn Ile Lys Asp Ile Asp Val Ile Met Gly Gly Gly Arg Lys
            210                 215                 220

Tyr Met Tyr Pro Lys Asn Arg Thr Asp Val Glu Tyr Glu Leu Asp Glu
225                 230                 235                 240

Lys Ala Arg Gly Thr Arg Leu Asp Gly Leu Asp Leu Ile Ser Ile Trp
            245                 250                 255

Lys Ser Phe Lys Pro Arg His Lys His Ser His Tyr Val Trp Asn Arg
            260                 265                 270

Thr Glu Leu Leu Ala Leu Asp Pro Ser Arg Val Asp Tyr Leu Leu Gly
```

```
                    275                 280                 285
Leu Phe Glu Pro Gly Asp Met Gln Tyr Glu Leu Asn Arg Asn Asn Leu
290                 295                 300

Thr Asp Pro Ser Leu Ser Glu Met Val Glu Val Ala Leu Arg Ile Leu
305                 310                 315                 320

Thr Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Glu Ala Ile Gly Lys Ala Gly Thr Met Thr Ser Gln
            355                 360                 365

Lys Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Asp Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
450                 455                 460

Gly Pro Met Ala His Leu Leu His Gly Val His Glu Gln Asn Tyr Ile
465                 470                 475                 480

Pro His Val Met Ala Tyr Ala Ser Cys Ile Gly Ala Asn Leu Asp His
                485                 490                 495

Cys Ala Trp Ala Ser Ser Ala Ser Ser Pro Ser Pro Gly Ala Leu Leu
            500                 505                 510

Leu Pro Leu Ala Leu Phe Pro Leu Arg Thr Leu Phe
            515                 520

<210> SEQ ID NO 9
<211> LENGTH: 502
<212> TYPE: PRT
<213> ORGANISM: Canis lupus familiaris

<400> SEQUENCE: 9

Glu Lys Asp Pro Lys Tyr Trp Arg Asp Gln Ala Gln Gln Thr Leu Lys
1               5                   10                  15

Tyr Ala Leu Arg Leu Gln Asn Leu Asn Thr Asn Val Ala Lys Asn Val
            20                  25                  30

Ile Met Phe Leu Gly Asp Gly Met Gly Val Ser Thr Val Thr Ala Thr
        35                  40                  45

Arg Ile Leu Lys Gly Gln Leu His His Asn Pro Gly Glu Glu Thr Arg
    50                  55                  60

Leu Glu Met Asp Lys Phe Pro Tyr Val Ala Leu Ser Lys Thr Tyr Asn
65                  70                  75                  80

Thr Asn Ala Gln Val Pro Asp Ser Ala Gly Thr Ala Thr Ala Tyr Leu
                85                  90                  95

Cys Gly Val Lys Ala Asn Glu Gly Thr Val Gly Val Ser Ala Ala Thr
            100                 105                 110

Gln Arg Thr His Cys Asn Thr Thr Gln Gly Asn Glu Val Thr Ser Ile
        115                 120                 125
```

Leu Arg Trp Ala Lys Asp Ala Gly Lys Ser Val Gly Ile Val Thr Thr
130                 135                 140

Thr Arg Val Asn His Ala Thr Pro Ser Ala Ala Tyr Ala His Ser Ala
145                 150                 155                 160

Asp Arg Asp Trp Tyr Ser Asp Asn Glu Met Pro Pro Glu Ala Leu Ser
                165                 170                 175

Gln Gly Cys Lys Asp Ile Ala Tyr Gln Leu Met His Asn Val Lys Asp
            180                 185                 190

Ile Glu Val Ile Met Gly Gly Arg Lys Tyr Met Phe Pro Lys Asn
        195                 200                 205

Arg Thr Asp Val Glu Tyr Glu Met Asp Glu Lys Ser Thr Gly Ala Arg
210                 215                 220

Leu Asp Gly Leu Asn Leu Ile Asp Ile Trp Lys Asn Phe Lys Pro Arg
225                 230                 235                 240

His Lys His Ser His Tyr Val Trp Asn Arg Thr Glu Leu Leu Ala Leu
                245                 250                 255

Asp Pro Tyr Thr Val Asp Tyr Leu Leu Gly Leu Phe Asp Pro Gly Asp
            260                 265                 270

Met Gln Tyr Glu Leu Asn Arg Asn Asn Val Thr Asp Pro Ser Leu Ser
        275                 280                 285

Glu Met Val Glu Ile Ala Ile Lys Ile Leu Ser Lys Lys Pro Arg Gly
290                 295                 300

Phe Phe Leu Leu Val Glu Gly Gly Arg Ile Asp His Gly His His Glu
305                 310                 315                 320

Gly Lys Ala Lys Gln Ala Leu His Glu Ala Val Glu Met Asp Arg Ala
                325                 330                 335

Ile Gly Lys Ala Gly Val Met Thr Ser Leu Glu Asp Thr Leu Thr Val
            340                 345                 350

Val Thr Ala Asp His Ser His Val Phe Thr Phe Gly Gly Tyr Thr Pro
        355                 360                 365

Arg Gly Asn Ser Ile Phe Gly Leu Ala Pro Met Val Ser Asp Thr Asp
370                 375                 380

Lys Lys Pro Phe Thr Ala Ile Leu Tyr Gly Asn Gly Pro Gly Tyr Lys
385                 390                 395                 400

Val Val Gly Gly Glu Arg Glu Asn Val Ser Met Val Asp Tyr Ala His
                405                 410                 415

Asn Asn Tyr Gln Ala Gln Ser Ala Val Pro Leu Arg His Glu Thr His
            420                 425                 430

Gly Gly Glu Asp Val Ala Val Phe Ala Lys Gly Pro Met Ala His Leu
        435                 440                 445

Leu His Gly Val His Glu Gln Asn Tyr Ile Pro His Val Met Ala Tyr
450                 455                 460

Ala Ala Cys Ile Gly Ala Asn Gln Asp His Cys Ala Ser Ala Ser Ser
465                 470                 475                 480

Ala Gly Gly Pro Ser Pro Gly Pro Leu Leu Leu Leu Ala Leu Leu
                485                 490                 495

Pro Val Gly Ile Leu Phe
            500

<210> SEQ ID NO 10
<211> LENGTH: 252
<212> TYPE: PRT
<213> ORGANISM: Sus scrofa

<400> SEQUENCE: 10

```
Ala Glu Leu Leu Ala Leu Asp Pro His Thr Val Asp Tyr Leu Leu Gly
1               5                   10                  15

Leu Phe Glu Pro Gly Asp Met Gln Tyr Glu Leu Asn Arg Asn Asn Val
            20                  25                  30

Thr Asp Pro Ser Leu Ser Glu Met Val Glu Met Ala Ile Arg Ile Leu
        35                  40                  45

Ile Lys Asn Pro Lys Gly Phe Phe Leu Leu Val Glu Gly Gly Arg Ile
    50                  55                  60

Asp His Gly His His Glu Gly Lys Ala Lys Gln Ala Leu His Glu Ala
65                  70                  75                  80

Val Glu Met Asp Arg Ala Ile Glu Gln Ala Gly Ser Met Thr Ser Val
                85                  90                  95

Glu Asp Thr Leu Thr Val Val Thr Ala Asp His Ser His Val Phe Thr
            100                 105                 110

Phe Gly Gly Tyr Thr Pro Arg Gly Asn Ser Ile Phe Gly Leu Ala Pro
        115                 120                 125

Met Val Ser Asp Thr Asp Lys Lys Pro Phe Thr Ala Ile Leu Tyr Gly
    130                 135                 140

Asn Gly Pro Gly Tyr Lys Val Val Gly Gly Glu Arg Glu Asn Val Ser
145                 150                 155                 160

Met Val Asp Tyr Ala His Asp Asn Tyr Gln Ala Gln Ser Ala Val Pro
                165                 170                 175

Leu Arg His Glu Thr His Gly Gly Glu Asp Val Ala Ile Phe Ala Arg
            180                 185                 190

Gly Pro Met Ala His Leu Leu His Gly Val His Glu Gln Asn Tyr Ile
        195                 200                 205

Pro His Val Met Ala Tyr Ala Ala Cys Val Gly Ala Asn Arg Asp His
    210                 215                 220

Cys Ala Ser Ala Ser Ser Gly Ser Pro Ser Pro Gly Pro Leu Leu
225                 230                 235                 240

Leu Leu Leu Ala Leu Leu Pro Leu Gly Ile Leu Phe
            245                 250

<210> SEQ ID NO 11
<211> LENGTH: 524
<212> TYPE: PRT
<213> ORGANISM: Mus musculus

<400> SEQUENCE: 11

Met Ile Ser Pro Phe Leu Val Leu Ala Ile Gly Thr Cys Leu Thr Asn
1               5                   10                  15

Ser Phe Val Pro Glu Lys Glu Arg Asp Pro Ser Tyr Trp Arg Gln Gln
            20                  25                  30

Ala Gln Glu Thr Leu Lys Asn Ala Leu Lys Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Thr Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
```

```
            115                 120                 125
Gly Val Ser Ala Ala Thr Glu Arg Thr Arg Cys Asn Thr Thr Gln Gly
            130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                    165                 170                 175

Ala Tyr Ala His Ser Ala Asp Arg Asp Trp Tyr Ser Asp Asn Glu Met
                180                 185                 190

Pro Pro Glu Ala Leu Ser Gln Gly Cys Lys Asp Ile Ala Tyr Gln Leu
            195                 200                 205

Met His Asn Ile Lys Asp Ile Asp Val Ile Met Gly Gly Gly Arg Lys
            210                 215                 220

Tyr Met Tyr Pro Lys Asn Arg Thr Asp Val Glu Tyr Glu Leu Asp Glu
225                 230                 235                 240

Lys Ala Arg Gly Thr Arg Leu Asp Gly Leu Asp Leu Ile Ser Ile Trp
                    245                 250                 255

Lys Ser Phe Lys Pro Arg His Lys His Ser His Tyr Val Trp Asn Arg
                260                 265                 270

Thr Glu Leu Leu Ala Leu Asp Pro Ser Arg Val Asp Tyr Leu Leu Gly
            275                 280                 285

Leu Phe Glu Pro Gly Asp Met Gln Tyr Glu Leu Asn Arg Asn Asn Leu
            290                 295                 300

Thr Asp Pro Ser Leu Ser Glu Met Val Glu Val Ala Leu Arg Ile Leu
305                 310                 315                 320

Thr Lys Asn Leu Lys Gly Phe Phe Leu Leu Val Glu Gly Gly Arg Ile
                    325                 330                 335

Asp His Gly His His Glu Gly Lys Ala Lys Gln Ala Leu His Glu Ala
                340                 345                 350

Val Glu Met Asp Gln Ala Ile Gly Lys Ala Gly Ala Met Thr Ser Gln
            355                 360                 365

Lys Asp Thr Leu Thr Val Val Thr Ala Asp His Ser His Val Phe Thr
            370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                    405                 410                 415

Asn Gly Pro Gly Tyr Lys Val Val Asp Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ala Lys
            450                 455                 460

Gly Pro Met Ala His Leu Leu His Gly Val His Glu Gln Asn Tyr Ile
465                 470                 475                 480

Pro His Val Met Ala Tyr Ala Ser Cys Ile Gly Ala Asn Leu Asp His
                    485                 490                 495

Cys Ala Trp Ala Gly Ser Gly Ser Ala Pro Ser Pro Gly Ala Leu Leu
                500                 505                 510

Leu Pro Leu Ala Val Leu Ser Leu Arg Thr Leu Phe
            515                 520

<210> SEQ ID NO 12
```

<211> LENGTH: 524
<212> TYPE: PRT
<213> ORGANISM: Bos taurus

<400> SEQUENCE: 12

```
Met Ile Ser Pro Phe Leu Leu Leu Ala Ile Gly Thr Cys Phe Ala Ser
1               5                   10                  15

Ser Leu Val Pro Glu Lys Glu Lys Asp Pro Lys Tyr Trp Arg Asp Gln
            20                  25                  30

Ala Gln Gln Thr Leu Lys Asn Ala Leu Arg Leu Gln Thr Leu Asn Thr
        35                  40                  45

Asn Val Ala Lys Asn Val Ile Met Phe Leu Gly Asp Gly Met Gly Val
50                  55                  60

Ser Thr Val Thr Ala Ala Arg Ile Leu Lys Gly Gln Leu His His Ser
65                  70                  75                  80

Pro Gly Glu Glu Thr Lys Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Ser Gln Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ser Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Glu Val Ile Met Gly Gly Gly Arg Lys
210                 215                 220

Tyr Met Phe Pro Lys Asn Arg Thr Asp Val Glu Tyr Glu Leu Asp Glu
225                 230                 235                 240

Lys Ala Arg Gly Thr Arg Leu Asp Gly Leu Asn Leu Ile Asp Ile Trp
                245                 250                 255

Lys Ser Phe Lys Pro Lys His Lys His Ser His Tyr Val Trp Asn Arg
            260                 265                 270

Thr Asp Leu Leu Ala Leu Asp Pro His Ser Val Asp Tyr Leu Leu Gly
        275                 280                 285

Leu Phe Glu Pro Gly Asp Met Gln Tyr Glu Leu Asn Arg Asn Asn Ala
290                 295                 300

Thr Asp Pro Ser Leu Ser Glu Met Val Glu Met Ala Ile Arg Ile Leu
305                 310                 315                 320

Asn Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Gln Ala Gly Ala Met Thr Ser Val
        355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
```

```
385                 390                 395                 400
Met Val Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ala Lys
        450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Arg Asp His
                485                 490                 495

Cys Ala Ser Ala Ser Ser Ser Gly Ser Pro Ser Pro Gly Pro Leu Leu
                500                 505                 510

Leu Leu Leu Ala Leu Leu Pro Leu Gly Ser Leu Phe
            515                 520

<210> SEQ ID NO 13
<211> LENGTH: 524
<212> TYPE: PRT
<213> ORGANISM: Bos taurus

<400> SEQUENCE: 13

Met Ile Ser Pro Phe Leu Leu Leu Ala Ile Gly Thr Cys Phe Ala Ser
1                5                  10                  15

Ser Leu Val Pro Glu Lys Glu Lys Asp Pro Lys Tyr Trp Arg Asp Gln
            20                  25                  30

Ala Gln Gln Thr Leu Lys Asn Ala Leu Arg Leu Gln Thr Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Ser
65                  70                  75                  80

Pro Gly Glu Glu Thr Lys Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Ser Gln Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ser Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Glu Val Ile Met Gly Gly Gly Arg Lys
    210                 215                 220

Tyr Met Phe Pro Lys Asn Arg Thr Asp Val Glu Tyr Glu Leu Asp Glu
225                 230                 235                 240
```

```
Lys Ala Arg Gly Thr Arg Leu Asp Gly Leu Asn Leu Ile Asp Ile Trp
            245                 250                 255

Lys Ser Phe Lys Pro Lys His Lys His Ser His Tyr Val Trp Asn Arg
        260                 265                 270

Thr Asp Leu Leu Ala Leu Asp Pro His Ser Val Asp Tyr Leu Leu Gly
        275                 280                 285

Leu Phe Glu Pro Gly Asp Met Gln Tyr Glu Leu Asn Arg Asn Asn Ala
        290                 295                 300

Thr Asp Pro Ser Leu Ser Glu Met Val Glu Met Ala Ile Arg Ile Leu
305                 310                 315                 320

Asn Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Gln Ala Gly Ala Met Thr Ser Val
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Gly Glu Arg Glu Asn Val Ser
            420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Arg Asp His
                485                 490                 495

Cys Ala Ser Ala Ser Ser Ser Gly Ser Pro Ser Pro Gly Pro Leu Leu
            500                 505                 510

Leu Leu Leu Ala Leu Leu Pro Leu Gly Ser Leu Phe
            515                 520

<210> SEQ ID NO 14
<211> LENGTH: 124
<212> TYPE: PRT
<213> ORGANISM: Bos taurus

<400> SEQUENCE: 14

Asp Pro Lys Tyr Trp Arg Asp Gln Ala Gln Gln Thr Leu Lys Asn Ala
1               5                   10                  15

Leu Gly Leu Gln Lys Leu Asn Thr Lys Val Ala Lys Asn Val Ile Leu
            20                  25                  30

Phe Leu Gly Asp Gly Met Gly Val Ser Thr Val Thr Ala Ala Arg Ile
        35                  40                  45

Leu Lys Gly Gln Leu His His Asn Pro Gly Glu Glu Thr Arg Leu Glu
    50                  55                  60

Met Asp Lys Phe Pro Phe Val Ala Leu Ser Lys Thr Tyr Asn Thr Asn
65                  70                  75                  80

Ala Gln Val Pro Asp Ser Ala Gly Thr Ala Pro His Pro Val Arg Val
                85                  90                  95
```

```
Lys Ala Met Arg Ala Pro Trp Gly Glu Pro His Gln Arg Gln Cys Asn
            100                 105                 110

Thr Arg Arg Ala Thr Ser Thr His Leu Leu Ala Gly
        115                 120
```

<210> SEQ ID NO 15
<211> LENGTH: 524
<212> TYPE: PRT
<213> ORGANISM: Felis catus

<400> SEQUENCE: 15

```
Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Gln Thr Leu Lys Asn Ala Leu Arg Leu Gln Lys Leu Asn Thr
        35                  40                  45

Asn Val Val Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Thr Gln Cys Asn Thr Thr Gln Gly
    130                 135                 140

Asn Glu Val Thr Ser Ile Leu Arg Trp Ala Lys Asp Ser Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Val Arg Asp Ile Glu Val Ile Met Gly Gly Gly Arg Lys
    210                 215                 220

Tyr Met Phe Pro Lys Asn Arg Thr Asp Val Glu Tyr Glu Met Asp Glu
225                 230                 235                 240

Lys Ala Arg Gly Thr Arg Leu Asp Gly Leu Asn Leu Val Asp Ile Trp
                245                 250                 255

Lys Ser Phe Lys Pro Arg His Lys His Ser His Tyr Val Trp Asn Arg
            260                 265                 270

Thr Glu Leu Leu Thr Leu Asp Pro Tyr Gly Val Asp Tyr Leu Leu Gly
        275                 280                 285

Leu Phe Glu Pro Gly Asp Met Gln Tyr Glu Leu Asn Arg Asn Ser Thr
    290                 295                 300

Thr Asp Pro Ser Leu Ser Glu Met Val Glu Ile Ala Ile Lys Ile Leu
305                 310                 315                 320

Ser Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
```

-continued

```
                340                 345                 350
Val Glu Met Asp Gln Ala Ile Gly Arg Ala Gly Ala Met Thr Ser Val
            355                 360                 365

Glu Asp Thr Leu Thr Ile Val Thr Ala Asp His Ser His Val Phe Thr
        370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ser Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Leu Asp His
                485                 490                 495

Cys Ala Ser Ala Ser Ser Ala Gly Gly Pro Ser Pro Gly Pro Leu Phe
            500                 505                 510

Leu Leu Leu Ala Leu Pro Ser Leu Gly Ile Leu Phe
        515                 520
```

<210> SEQ ID NO 16
<211> LENGTH: 532
<212> TYPE: PRT
<213> ORGANISM: Homo sapiens

<400> SEQUENCE: 16

```
Met Gln Gly Pro Trp Val Leu Leu Leu Gly Leu Arg Leu Gln Leu
1               5                   10                  15

Ser Leu Gly Ile Ile Pro Val Glu Glu Asn Pro Asp Phe Trp Asn
                20                  25                  30

Arg Gln Ala Ala Glu Ala Leu Gly Ala Ala Lys Lys Leu Gln Pro Ala
            35                  40                  45

Gln Thr Ala Ala Lys Asn Leu Ile Ile Phe Leu Gly Asp Gly Met Gly
        50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
                100                 105                 110

Ala Thr Ala Thr Ala Tyr Leu Cys Gly Val Lys Gly Asn Phe Gln Thr
            115                 120                 125

Ile Gly Leu Ser Ala Ala Ala Arg Phe Asn Gln Cys Asn Thr Thr Arg
        130                 135                 140

Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190
```

Val Pro Ala Ser Ala Arg Gln Glu Gly Cys Gln Asp Ile Ala Thr Gln
            195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
                245                 250                 255

Leu Ala Lys His Gln Gly Ala Arg Tyr Val Trp Asn Arg Thr Glu Leu
            260                 265                 270

Leu Gln Ala Ser Leu Asp Pro Ser Val Thr His Leu Met Gly Leu Phe
        275                 280                 285

Glu Pro Gly Asp Met Lys Tyr Glu Ile His Arg Asp Ser Thr Leu Asp
    290                 295                 300

Pro Ser Leu Met Glu Met Thr Glu Ala Ala Leu Leu Leu Ser Arg
305                 310                 315                 320

Asn Pro Arg Gly Phe Phe Leu Phe Val Glu Gly Gly Arg Ile Asp His
                325                 330                 335

Gly His His Glu Ser Arg Ala Tyr Arg Ala Leu Thr Glu Thr Ile Met
            340                 345                 350

Phe Asp Asp Ala Ile Glu Arg Ala Gly Gln Leu Thr Ser Glu Glu Asp
        355                 360                 365

Thr Leu Ser Leu Val Thr Ala Asp His Ser His Val Phe Ser Phe Gly
    370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                405                 410                 415

Gly Tyr Val Leu Lys Asp Gly Ala Arg Pro Asp Val Thr Glu Ser Glu
            420                 425                 430

Ser Gly Ser Pro Glu Tyr Arg Gln Gln Ser Ala Val Pro Leu Asp Gly
        435                 440                 445

Glu Thr His Ala Gly Glu Asp Val Ala Val Phe Ala Arg Gly Pro Gln
    450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
            500                 505                 510

Pro Ala Leu Leu Pro Leu Leu Ala Gly Thr Leu Leu Leu Gly Thr
        515                 520                 525

Ala Thr Ala Pro
530

<210> SEQ ID NO 17
<211> LENGTH: 535
<212> TYPE: PRT
<213> ORGANISM: Homo sapiens

<400> SEQUENCE: 17

Met Leu Gly Pro Cys Met Leu Leu Leu Leu Leu Leu Gly Leu Arg
1               5                   10                  15

Leu Gln Leu Ser Leu Gly Ile Ile Pro Val Glu Glu Glu Asn Pro Asp
            20                  25                  30

-continued

```
Phe Trp Asn Arg Glu Ala Ala Glu Ala Leu Gly Ala Ala Lys Lys Leu
        35                  40                  45

Gln Pro Ala Gln Thr Ala Ala Lys Asn Leu Ile Ile Phe Leu Gly Asp
        50                  55                  60

Gly Met Gly Val Ser Thr Val Thr Ala Ala Arg Ile Leu Lys Gly Gln
65                  70                  75                  80

Lys Lys Asp Lys Leu Gly Pro Glu Ile Pro Leu Ala Met Asp Arg Phe
                85                  90                  95

Pro Tyr Val Ala Leu Ser Lys Thr Tyr Asn Val Asp Lys His Val Pro
               100                 105                 110

Asp Ser Gly Ala Thr Ala Thr Ala Tyr Leu Cys Gly Val Lys Gly Asn
               115                 120                 125

Phe Gln Thr Ile Gly Leu Ser Ala Ala Arg Phe Asn Gln Cys Asn
               130                 135                 140

Thr Thr Arg Gly Asn Glu Val Ile Ser Val Met Asn Arg Ala Lys Lys
145                 150                 155                 160

Ala Gly Lys Ser Val Gly Val Val Thr Thr Thr Arg Val Gln His Ala
                165                 170                 175

Ser Pro Ala Gly Thr Tyr Ala His Thr Val Asn Arg Asn Trp Tyr Ser
                180                 185                 190

Asp Ala Asp Val Pro Ala Ser Ala Arg Gln Glu Gly Cys Gln Asp Ile
                195                 200                 205

Ala Thr Gln Leu Ile Ser Asn Met Asp Ile Asp Val Ile Leu Gly Gly
               210                 215                 220

Gly Arg Lys Tyr Met Phe Arg Met Gly Thr Pro Asp Pro Glu Tyr Pro
225                 230                 235                 240

Asp Asp Tyr Ser Gln Gly Gly Thr Arg Leu Asp Gly Lys Asn Leu Val
                245                 250                 255

Gln Glu Trp Leu Ala Lys Arg Gln Gly Ala Arg Tyr Val Trp Asn Arg
                260                 265                 270

Thr Glu Leu Met Gln Ala Ser Leu Asp Pro Ser Val Thr His Leu Met
                275                 280                 285

Gly Leu Phe Glu Pro Gly Asp Met Lys Tyr Glu Ile His Arg Asp Ser
                290                 295                 300

Thr Leu Asp Pro Ser Leu Met Glu Met Thr Glu Ala Ala Leu Arg Leu
305                 310                 315                 320

Leu Ser Arg Asn Pro Arg Gly Phe Phe Leu Phe Val Glu Gly Gly Arg
                325                 330                 335

Ile Asp His Gly His His Glu Ser Arg Ala Tyr Arg Ala Leu Thr Glu
                340                 345                 350

Thr Ile Met Phe Asp Asp Ala Ile Glu Arg Ala Gly Gln Leu Thr Ser
                355                 360                 365

Glu Glu Asp Thr Leu Ser Leu Val Thr Ala Asp His Ser His Val Phe
370                 375                 380

Ser Phe Gly Gly Tyr Pro Leu Arg Gly Ser Ser Ile Phe Gly Leu Ala
385                 390                 395                 400

Pro Gly Lys Ala Arg Asp Arg Lys Ala Tyr Thr Val Leu Leu Tyr Gly
                405                 410                 415

Asn Gly Pro Gly Tyr Val Leu Lys Asp Gly Ala Arg Pro Asp Val Thr
                420                 425                 430

Glu Ser Glu Ser Gly Ser Pro Glu Tyr Arg Gln Gln Ser Ala Val Pro
                435                 440                 445
```

```
Leu Asp Glu Thr His Ala Gly Glu Asp Val Ala Val Phe Ala Arg
    450                 455                 460

Gly Pro Gln Ala His Leu Val His Gly Val Gln Glu Gln Thr Phe Ile
465                 470                 475                 480

Ala His Val Met Ala Phe Ala Ala Cys Leu Glu Pro Tyr Thr Ala Cys
                485                 490                 495

Asp Leu Ala Pro Pro Ala Gly Thr Thr Asp Ala Ala His Pro Gly Arg
                500                 505                 510

Ser Val Val Pro Ala Leu Leu Pro Leu Leu Ala Gly Thr Leu Leu Leu
                515                 520                 525

Leu Glu Thr Ala Thr Ala Pro
    530                 535

<210> SEQ ID NO 18
<211> LENGTH: 532
<212> TYPE: PRT
<213> ORGANISM: Homo sapiens

<400> SEQUENCE: 18

Met Gln Gly Pro Trp Val Leu Leu Leu Gly Leu Arg Leu Gln Leu
1               5                   10                  15

Ser Leu Gly Ile Ile Pro Val Glu Glu Glu Asn Pro Asp Phe Trp Asn
                20                  25                  30

Arg Gln Ala Ala Glu Ala Leu Gly Ala Ala Lys Lys Leu Gln Pro Ala
            35                  40                  45

Gln Thr Ala Ala Lys Asn Leu Ile Ile Phe Leu Gly Asp Gly Met Gly
        50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
                100                 105                 110

Ala Thr Ala Thr Ala Tyr Leu Cys Gly Val Lys Gly Asn Phe Gln Thr
            115                 120                 125

Ile Gly Leu Ser Ala Ala Ala Arg Phe Asn Gln Cys Asn Thr Thr Arg
        130                 135                 140

Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
                180                 185                 190

Val Pro Ala Ser Ala Arg Gln Glu Gly Cys Gln Asp Ile Ala Thr Gln
            195                 200                 205

Leu Ile Ser Asn Met Asp Ile Asp Val Ile Leu Gly Gly Gly Arg Lys
        210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
                245                 250                 255

Leu Ala Lys His Gln Gly Ala Arg Tyr Val Trp Asn Arg Thr Glu Leu
                260                 265                 270

Leu Gln Ala Ser Leu Asp Pro Ser Val Thr His Leu Met Gly Leu Phe
            275                 280                 285
```

Glu Pro Gly Asp Met Lys Tyr Glu Ile His Arg Asp Ser Thr Leu Asp
            290                 295                 300

Pro Ser Leu Met Glu Met Thr Glu Ala Ala Leu Leu Leu Ser Arg
305                 310                 315                 320

Asn Pro Arg Gly Phe Phe Leu Phe Val Glu Gly Gly Arg Ile Asp His
                325                 330                 335

Gly His His Glu Ser Arg Ala Tyr Arg Ala Leu Thr Glu Thr Ile Met
            340                 345                 350

Phe Asp Asp Ala Ile Glu Arg Ala Gly Gln Leu Thr Ser Glu Glu Asp
                355                 360                 365

Thr Leu Ser Leu Val Thr Ala Asp His Ser His Val Phe Ser Phe Gly
370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                405                 410                 415

Gly Tyr Val Leu Lys Asp Gly Ala Arg Pro Asp Val Thr Glu Ser Glu
                420                 425                 430

Ser Gly Ser Pro Glu Tyr Arg Gln Gln Ser Ala Val Pro Leu Asp Gly
            435                 440                 445

Glu Thr His Ala Gly Glu Asp Val Ala Val Phe Ala Arg Gly Pro Gln
450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
                500                 505                 510

Pro Ala Leu Leu Pro Leu Leu Ala Gly Thr Leu Leu Leu Leu Gly Thr
            515                 520                 525

Ala Thr Ala Pro
            530

<210> SEQ ID NO 19
<211> LENGTH: 528
<212> TYPE: PRT
<213> ORGANISM: Homo sapiens

<400> SEQUENCE: 19

Met Gln Gly Pro Trp Val Leu Leu Leu Leu Gly Leu Arg Leu Gln Leu
1               5                   10                  15

Ser Leu Gly Val Ile Pro Ala Glu Glu Glu Asn Pro Ala Phe Trp Asn
            20                  25                  30

Arg Gln Ala Ala Glu Ala Leu Asp Ala Ala Lys Lys Leu Gln Pro Ile
        35                  40                  45

Gln Lys Val Ala Lys Asn Leu Ile Leu Phe Leu Gly Asp Gly Leu Gly
    50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
            100                 105                 110

Ala Thr Ala Thr Ala Tyr Leu Cys Gly Val Lys Ala Asn Phe Gln Thr

```
            115                 120                 125
Ile Gly Leu Ser Ala Ala Ala Arg Phe Asn Gln Cys Asn Thr Thr Arg
        130                 135                 140
Gly Asn Glu Val Ile Ser Val Met Asn Arg Ala Lys Gln Ala Gly Lys
145                 150                 155                 160
Ser Val Gly Val Val Thr Thr Thr Arg Val Gln His Ala Ser Pro Ala
                165                 170                 175
Gly Thr Tyr Ala His Thr Val Asn Arg Asn Trp Tyr Ser Asp Ala Asp
            180                 185                 190
Met Pro Ala Ser Ala Arg Gln Glu Gly Cys Gln Asp Ile Ala Thr Gln
        195                 200                 205
Leu Ile Ser Asn Met Asp Ile Asp Val Ile Leu Gly Gly Arg Lys
210                 215                 220
Tyr Met Phe Pro Met Gly Thr Pro Asp Pro Tyr Pro Ala Asp Ala
225                 230                 235                 240
Ser Gln Asn Gly Ile Arg Leu Asp Gly Lys Asn Leu Val Gln Glu Trp
                245                 250                 255
Leu Ala Lys His Gln Gly Ala Trp Tyr Val Trp Asn Arg Thr Glu Leu
            260                 265                 270
Met Gln Ala Ser Leu Asp Gln Ser Val Thr His Leu Met Gly Leu Phe
        275                 280                 285
Glu Pro Gly Asp Thr Lys Tyr Glu Ile His Arg Asp Pro Thr Leu Asp
290                 295                 300
Pro Ser Leu Met Glu Met Thr Glu Ala Ala Leu Arg Leu Leu Ser Arg
305                 310                 315                 320
Asn Pro Arg Gly Phe Tyr Leu Phe Val Glu Gly Arg Ile Asp His
                325                 330                 335
Gly His His Glu Gly Val Ala Tyr Gln Ala Leu Thr Glu Ala Val Met
            340                 345                 350
Phe Asp Asp Ala Ile Glu Arg Ala Gly Gln Leu Thr Ser Glu Glu Asp
        355                 360                 365
Thr Leu Thr Leu Val Thr Ala Asp His Ser His Val Phe Ser Phe Gly
370                 375                 380
Gly Tyr Thr Leu Arg Gly Ser Ser Ile Phe Gly Leu Ala Pro Ser Lys
385                 390                 395                 400
Ala Gln Asp Ser Lys Ala Tyr Thr Ser Ile Leu Tyr Gly Asn Gly Pro
                405                 410                 415
Gly Tyr Val Phe Asn Ser Gly Val Arg Pro Asp Val Asn Glu Ser Glu
            420                 425                 430
Ser Gly Ser Pro Asp Tyr Gln Gln Ala Ala Val Pro Leu Ser Ser
        435                 440                 445
Glu Thr His Gly Gly Glu Asp Val Ala Val Phe Ala Arg Gly Pro Gln
450                 455                 460
Ala His Leu Val His Gly Val Gln Glu Gln Ser Phe Val Ala His Val
465                 470                 475                 480
Met Ala Phe Ala Ala Cys Leu Glu Pro Tyr Thr Ala Cys Asp Leu Ala
                485                 490                 495
Pro Pro Ala Cys Thr Thr Asp Ala Ala His Pro Val Ala Ala Ser Leu
            500                 505                 510
Pro Leu Leu Ala Gly Thr Leu Leu Leu Gly Ala Ser Ala Ala Pro
        515                 520                 525

<210> SEQ ID NO 20
```

```
<211> LENGTH: 227
<212> TYPE: PRT
<213> ORGANISM: Artificial Sequence
<220> FEATURE:
<223> OTHER INFORMATION: Synthetic Construct

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

METHODS OF TREATING NEUROFIBROMATOSIS TYPE 1 AND RELATED CONDITIONS WITH ALKALINE PHOSPHATASE

BACKGROUND

Numerous diseases and conditions involve abnormal skeletal function, structure, or growth of bone or cartilage. An example of such a disease is neurofibromatosis type 1 (NF1 or Von Recklinghausen disease). NF1 is an autosomal dominant genetic disorder having an incidence of approximately 1 in 3,500 live births. The gene NF1 encodes neurofibromin, a member of the GTPase Activating Protein (GAP) family known to suppress the Ras kinase. Neurofibromin is a specific suppressor of p21-RAS, and mutations in the NF1 gene cause unsuppressed activation of RAS that lead to abnormal cell growth and differentiation. Common clinical features of NF1 include various oncogenic transformations, such as neurocutaneous neurofibromas and optic pathway tumors, and other non-cancer manifestations, such as cognitive defects and skeletal abnormalities.

Neurofibromatosis type 1 can interfere with the development of the spine. The disease may affect the protective covering of the spine, called the dura. Increased pressure in the spinal fluid due to neurofibromas of the spinal nerves can result in dural ectasia, which is a ballooning out of a sac that contains the cerebrospinal fluid. This condition may result in pain in the back and limbs, bladder control problems, and numbness in severe cases. Neurofibromatosis may also cause tumors on and around the spinal cord. Even benign tumors in this area can cause pain and weakness in the most severe cases. Osteoporosis is common among neurofibromatosis type 1 sufferers, who generally have lower bone density by age than healthy individuals.

Children with neurofibromatosis type 1 may develop dystrophic scoliosis, non-dystrophic scoliosis, and/or kyphosis. Scoliosis, an irregular side curvature of the spine from left to right, and kyphosis, a rounded or forward angulated back, occur together or separately in about one in five people with neurofibromatosis type 1. Non-dystrophic scoliosis, even in children with neurofibromatosis, is quite similar to "typical" scoliosis known as adolescent idiopathic scoliosis. Dystrophic scoliosis, however, is a more severe form of scoliosis that occurs due to bony changes related to neurofibromas affecting the spine. It may be accompanied by abnormally thin ribs, weakened vertebral bones, and severe spinal curvature.

Dystrophic scoliosis is a rare, but serious, skeletal manifestation in patients with NF1 that may be associated with debilitating neurological impairment (paraparesis, paraplegia). It is characterized by a sharp angulation involving several vertebrae, vertebral rotation, vertebral scalloping, vertebral wedging, and other radiographic features (Durrani et al., 2000). An anteroposterior spine radiograph, even in a patient only 14 years old, diagnosed with NF1, shows a thoracolumbar dystrophic scoliosis with a 49 degree curve over only 3 vertebrae (Petryk et al., 2016).

Dystrophic curves portend rapid progression and require early fusion, which is associated with significant morbidity. The postsurgical course is complicated by inherently poor bone healing in NF1 patients, resulting in pseudoarthrosis (lack of fusion) in as many as 60-100% of patients with NF-1 receiving posterior spinal fusion (Delucia et al., 2011). For example, 3 out of 3 NF1 patients with scoliosis who were treated had pseudoarthrosis after posterior spinal fusion, compared to $1/100$ patients with adolescent idiopathic scoliosis.

Treatment for scoliosis is always challenging, but particularly so when dystrophic scoliosis is present. While physical therapy may be able to relieve minor structural problems with the spine, definitive treatment often requires orthopedic surgery. For example, arthrodesis, a method for inducing the ossification of bones by surgery, can be employed to effect a spinal fusion in affected patients. Arthrodesis can involve the use of a natural bone graft (e.g., an autograft or an allograft), or the introduction of a synthetic bone substitute into the affected area. Examples of synthetic bone substitutes include hydroxyapatite- or tricalcium phosphate-based granules, as well as bone morphogenetic proteins (BMP). Another option is the attachment of metal implants to the bones to hold them together in a position which favors bone growth. Arthrodesis is commonly used to promote healing of bone fractures in or near a joint in the spine, hand, ankle, foot, hip, or knee, for example, wherein the fractures are caused by accident, injury, or progressive deterioration. Arthrodesis can also be employed to treat NF1-associated scoliosis and kyphosis. The end result is typically the fusion of two adjoining bones such that movement of the bones relative to each other is restricted.

Based on animal and in vitro studies, poor bone healing in NF1 is thought to be due to a combination of reduced bone formation, increased bone resorption, and poor bone mineralization, the key processes involved in normal bone homeostasis and bone repair. Preclinical studies show that bone pathology in NF1 is, to a large degree, due to hyperactivation of Ras pathway and pyrophosphate (PPi) accumulation (de la Croix Ndong et al., 2014). Neurofibromin accelerates the conversion of the active Ras, bound to GTP into its inactive form, bound to GDP. It also leads to upregulation of expression of genes that promote PPi synthesis and extracellular transport, leading to PPi accumulation and inhibition of mineralization. Loss of NF1 also leads to impaired osteoblast differentiation from mesenchymal progenitor cells and alkaline phosphatase expression (Wu et al., 2006; Yu et al., 2005) as well as markedly increased osteoclastogenesis and bone resorption (Yang et al., 2006).

Given the difficulties with achieving solid arthrodesis after surgery for dystrophic scoliosis in NF1, single agent therapy was apparently not an appropriate or effective treatment strategy. The use of recombinant bone morphogenetic proteins (BMPs) to induce bone formation has been established in spinal fusion surgery, although the response of osteoprogenitor cells to BMP treatment alone in NF1 appears to be limited (de la Croix Ndong et al., 2014; Heerva et al., 2012), making the clinical outcome in this patient population unsatisfactory.

Subsequent studies have shown that a combined use of BMPs and bisphosphonates appears superior to BMP therapy alone in NF1-deficient mice (Schindeler et al., 2008) and NF1 patients (Birke et al., 2010) with pseudoarthrosis of the tibia. In a preclinical model of posterior spinal fusion, NF1-deficient mice treated with rhBMP2 and zoledronic acid also showed a significant improvement in fusion, although NF1-deficient mice still generated less bone than wild type controls (Bobyn et al., 2014). Other studies have combined these agents (Petryk et al., 2016).

However, the treatments that have been attempted so far, bone morphogenetic proteins (BMPs) to enhance bone formation and bisphosphonates (pamidronate and zoledronic acid) to inhibit bone resorption, failed to address the third key component of the pathogenic pathway in patients with NF1, which is impaired mineralization. Seitz et al. (2010) and surgical experience provide evidence for osteomalacia (reduced mineralization) in NF1 patients, presumably due to localized accumulation of PPi, and difficulty with surgical hardware remaining in its original location in the bone, with displacement of the rods into the surrounding soft tissue and even dura, resulting in serious neurological complications (Seitz et al., 2010).

Many skeletal diseases, including NF1, arise from loss of function of one or more proteins. As noted above, NF1 is characterized by the loss of neurofibromin. Another skeletal disease example is hypophosphatasia (HPP), a rare, heritable disease caused by one or more loss-of-function mutations in the gene ALPL, which encodes tissue-nonspecific alkaline phosphatase (TNALP or liver/bone/kidney type ALP). Alkaline phosphatase deficiency in osteoblasts and chondrocytes impairs skeletal mineralization, leading to symptoms of varying severity, from rickets or osteomalacia to almost complete absence of bone mineralization in utero. However, enzyme replacement therapy with unmodified alkaline phosphatase (e.g., infusion of native alkaline phosphatase) has been largely unsuccessful. Yet another example is achondroplasia, which causes dwarfism and may be accompanied by spinal complications such as kyphosis.

Improved treatments for neurofibromatosis, including NF1-related bone conditions, as well as for other forms of scoliosis, dystrophic scoliosis, kyphosis, fractures, demineralization, and the like, are needed.

SUMMARY

In general, this disclosure relates to the treatment of various diseases and conditions, including neurofibromatosis type 1, particularly dystrophic scoliosis and bone fractures, by administration of a soluble alkaline phosphatase (sALP, e.g., a sALP having at least 80, 85%, 90%, 95%, 97%, 99%, or 100% sequence identity to SEQ ID NO: 1, e.g., asfotase alfa), optionally in combination with a physical intervention, such as surgical intervention. In one embodiment, a disclosed method can result in stability following treatment, e.g., solid arthrodesis, stability of hardware inserted during the treatment method, increased stability of hardware present in the patient before the treatment method, and stable scoliosis (e.g., no increased curvature).

Provided herein is a method of treating at least one symptom of neurofibromatosis type 1 (NF1) in a patient. In one embodiment, the method includes at least one surgical intervention in a patient with NF1, and administering a sALP (e.g., a sALP having at least 80, 85%, 90%, 95%, 97%, 99%, or 100% sequence identity to SEQ ID NO: 1, e.g., asfotase alfa) to the patient before, during, and/or after the surgical intervention, at a dosage providing from about 0.2 mg/kg/week to about 12 mg/kg/week (e.g., from about 6 mg/kg/week to about 9 mg/kg/week, such as about 6 mg/kg/week, about 7 mg/kg/week, about 8 mg/kg/week, or about 9 mg/kg/week) of the sALP. In one embodiment, the sALP includes an amino acid sequence having at least 80, 85%, 90%, 95%, 97%, 99%, or 100% sequence identity to the sequence of SEQ ID NO: 1; preferably the sALP has the sequence of SEQ ID NO: 1. In one embodiment, the administration of the sALP results in one or more of (i) an increase in bone healing to result in new bone at a reference point in the patient compared to the reference point in the patient before the treatment, and/or (ii) an average change in bone mineral density of a reference point that is undetectable or no greater than 0.01% eight months after the administration of the sALP compared to the bone mineral density of the reference point in the patient before the treatment. In one embodiment, the at least one symptom includes one or more of spine curvature, kyphosis, osteoporosis, a weakened vertebra, thinning of a rib, rotation of a vertebra, vertebral wedging, erosion of a vertebra. rotational or angular spinal deformity, dural ectasia, incomplete bone mineralization, elevated blood and/or urine levels of phosphoethanolamine (PEA), hypomineralization, hypercalciuria, short stature, skeletal deformity, waddling gait, bone pain, bone fracture, weakness, and calcium pyrophosphate dihydrate crystal deposition.

Also provided herein is a method of treating at least one symptom of dystrophic scoliosis in a patient. In one embodiment, the method includes at least one surgical intervention on a patient with dystrophic scoliosis, and administering a sALP (e.g., a sALP having at least 80, 85%, 90%, 95%, 97%, 99%, or 100% sequence identity to SEQ ID NO: 1, e.g., asfotase alfa) to the patient before, during, and/or after the surgical intervention, at a dosage providing from about 0.2 mg/kg/week to about 12 mg/kg/week (e.g., from about 6 mg/kg/week to about 9 mg/kg/week, such as about 6 mg/kg/week, about 7 mg/kg/week, about 8 mg/kg/week, or about 9 mg/kg/week) of the sALP. In one embodiment, the sALP includes an amino acid sequence having at least 80, 85%, 90%, 95%, 97%, 99%, or 100% sequence identity to the sequence of SEQ ID NO: 1; preferably the sALP has the sequence of SEQ ID NO: 1. In one embodiment, the administration of the sALP results in one or more of (i) an increase in bone healing to result in new bone at a reference point in the patient compared to the reference point in the patient before the treatment, and/or (ii) an average change in bone mineral density of a reference point that is undetectable or no greater than 0.01% eight months after the administration of the sALP compared to the bone mineral density of the reference point in the patient before the treatment. In one embodiment, at least one symptom includes one or more of shorter and/or more sharply angulated curves compared to non-dystrophic scoliosis, bone abnormalities, thinning of a rib, a weakened vertebra bone, rotation of a vertebra, vertebral wedging, and erosion of a vertebra. In one embodiment, the dystrophic scoliosis includes NF1-related dystrophic scoliosis.

Further provided herein is a method of inducing bone healing in a patient. In one embodiment, the method includes administering a sALP to the patient at a dosage providing about 6 mg/kg/week of the sALP. In one embodiment, the method includes administering a sALP to the patient at a dosage providing about 9 mg/kg/week of the sALP. Alternatively, the method includes administering a dosage providing from about 0.2 mg/kg/week to about 12 mg/kg/week (e.g., from about 6 mg/kg/week to about 9 mg/kg/week, such as about 6 mg/kg/week, about 7 mg/kg/week, about 8 mg/kg/week, or about 9 mg/kg/week) of the sALP. In one embodiment, the sALP includes an amino acid sequence having at least 80, 85%, 90%, 95%, 97%, 99%, or 100% sequence identity to the sequence of SEQ ID NO: 1; preferably the sALP has the sequence of SEQ ID NO: 1. In one embodiment, the administration of the sALP is in conjunction with a surgical intervention. In one embodiment, the administration of the sALP results in one or more of (i) an increase in bone healing to result in new bone at a reference point in the patient compared to the reference point in the patient before the treatment, and/or (ii) an average change in bone mineral density of a reference point that is undetectable or no greater than 0.01% eight months after the administration of the sALP compared to the bone mineral density of the reference point in the patient before the treatment.

Further provided herein is method of treating at least one bone related disorder in a patient. The patient may be one that does not have a bone mineralization disorder (e.g., HPP, NF1, or craniosynostosis). In one embodiment, the method includes at least one surgical intervention in the patient. The method may include administering a sALP to the patient before, during, and/or after the surgical intervention, e.g., at a dosage providing from about 0.2 mg/kg/week to about 12 mg/kg/week (e.g., from about 6 mg/kg/week to about 9 mg/kg/week, such as about 6 mg/kg/week, about 7 mg/kg/week, about 8 mg/kg/week, or about 9 mg/kg/week). Administration of the sALP may result in one or more of an increase in bone healing that results in new bone at a reference point in the patient compared to the reference point in the patient before the treatment. In some embodiments, the patient has an average change in bone mineral density of a reference point that is undetectable or no greater than 0.01% eight months after the administration of the sALP compared to the bone mineral density of the reference point in the patient before the treatment. In other embodiments, the patient has an average change in bone mineral density of a reference point that is at least 0.01% eight months after the administration of the sALP compared to the bone mineral density of the reference point in the patient before the treatment. The at least one surgical intervention may be selected from the group consisting of arthroscopy of the knee, shoulder, hip, ankle, elbow, or wrist, fracture and meniscectomy, shoulder arthroscopy and decompression, carpal tunnel release, knee arthroscopy and chondroplasty, removal of support implant, knee arthroscopy and anterior cruciate ligament reconstruction, knee replacement, repair of femoral neck fracture, repair of trochanteric fracture, debridement of skin/muscle/bone/fracture, knee arthroscopy repair of one or both menisci, hip replacement, shoulder arthroscopy/distal clavicle excision, repair of rotator cuff tendon, repair fracture of radius or ulna, laminectomy, repair of ankle fracture (bimalleolar type), shoulder arthroscopy and debridement, lumbar spinal fusion, repair fracture of the distal part of radius, low back intervertebral disc surgery, incise finger tendon sheath, repair of ankle fracture (fibula), repair of femoral shaft fracture, and repair of trochanteric fracture. The hardware may be one or more of a screw, rod, plate, metal cage, nail, pin, and nut.

In one embodiment, the increase in bone healing is between two bones joined by arthrodesis, and in another embodiment the increase in bone healing is between two portions of a bone that has been separated by a fracture. In one embodiment, the increase in bone healing is in bone surrounding instrumentation. In one embodiment, the increase in bone healing is an increase in opacity. In one embodiment, the increase in opacity is determined by radiography or computed tomography (CT).

In one embodiment, the surgical intervention includes one or more of arthrodesis, removal of bone, insertion of bone graft material, or insertion of instrumentation. In one embodiment, the instrumentation includes one or more of screws, rods, plates, and metal cages. In one embodiment, the surgical intervention includes one or more of an open surgery or a minimally invasive surgery. In one embodiment, the sALP is administered about seven months after the surgical intervention (e.g., about seven to about twelve or more months after the surgical intervention).

The method can further include administering to the patient one or more bone morphogenetic protein(s) (BMP). In one embodiment, the BMP is administered during the surgical intervention.

The method can further include administering to the patient one or more bisphosphonate(s). In one embodiment, the bisphosphonate is administered after the surgical intervention. In one embodiment, the bisphosphonate is administered about three months after the surgical intervention (e.g., about three to about twelve months after the surgical intervention).

In one embodiment, the patient is about 12 years of age, or older than about 12 years of age. In one embodiment, the patient is about 18 years of age, or older than about 18 years of age. In one embodiment, the patient has not been previously administered the sALP.

In one embodiment, the sALP is formulated for daily or weekly administration. For instance, the sALP can be formulated for administration twice a week, three times a week, four times a week, five times a week, six times a week, or seven times a week. In one embodiment, the sALP is formulated at a dosage of 2 mg/kg for administration three times a week, at a dosage of 3 mg/kg for administration three times a week, or at a dosage of 1 mg/kg for administration six times a week. In one embodiment, the sALP is formulated for administration once daily, and in another embodiment is formulated for administration on consecutive or alternating days. In one embodiment, the sALP is administered for a treatment period of at least one month, at least two months, at least three months, at least four months, at least five months, at least six months, at least seven months, at least eight months, at least nine months, at least ten months, or longer.

In one embodiment, the sALP includes the amino acid sequence of SEQ ID NO: 1, and in another embodiment consists of the amino acid sequence of SEQ ID NO: 1. In one embodiment, the sALP is the soluble extracellular domain of an alkaline phosphatase.

In one embodiment, the sALP is administered in an amount that is therapeutically effective to treat at least one symptom of neurofibromatosis type 1, at least one symptom of dystrophic scoliosis, or to induce bone healing.

In one embodiment, the patient exhibits tolerability to administration of the sALP. The tolerability can include, for instance, a lack of or decreased incidence of adverse events selected from the group consisting of injection site erythema, decrease in hemoglobin, pyrexia, pneumonia, upper respiratory tract infection, otitis media, vomiting, constipation, diarrhea, tooth loss, nasopharyngitis, rash, dental caries, and irritability.

In one embodiment, the sALP is formulated in a pharmaceutical composition, with at least one pharmaceutically acceptable carrier. In one embodiment, the at least one pharmaceutically acceptable carrier is saline, and in another embodiment includes sodium chloride (e.g., 150 mM sodium chloride) and sodium phosphate (e.g., 25 mM sodium phosphate). In one embodiment, the pharmaceutical composition is formulated for subcutaneous, intramuscular, intravenous, oral, nasal, sublingual, intrathecal, or intradermal administration, or a combination thereof.

Also provided herein is a method that includes one or more of the features described herein.

By "asfotase alfa" is meant a human TNALP (hTNALP) fusion protein formulated for a method disclosed herein. Asfotase alfa (STRENSIQ®, Alexion Pharmaceuticals, Inc.) is a fusion protein including a soluble glycoprotein of two identical polypeptide chains, in which each polypeptide chain includes amino acid residues 1-726 of SEQ ID NO: 1 (see, for example, WO 2017/171871, and US Patent Application Publication 2013/0323244). The structure of each polypeptide chain includes the catalytic domain of hTNALP, the human immunoglobulin G1 Fc domain, and a deca-aspartate peptide used as a bone targeting domain (the structure hTNALP-Fc-D10). The two polypeptide chains are covalently linked by two disulfide bonds. Asfotase alfa has been approved under the trade name STRENSIQ® in many countries, including the United States, Europe, Japan, Canada, Israel, Australia, and Korea.

As used herein, "average" refers to a numerical value expressing the mean or median of a data set. The mean of a data set is calculated by dividing the sum of the values in the set by their number. The median of a date set is calculated by determining the middle value in a list of odd numbers or by determining the mean of the two data values in the middle in a list of even numbers.

The term "bone-targeting moiety," as used herein, refers to an amino acid sequence of between 1 and 50 amino acid residues (such as 1, 2, 3, 4, 5, 6, 7, 8, 9, 10, 12, 14, 15, 16, 18, 20, 22, 24, 25, 26, 28, 30, 32, 34, 35, 36, 38, 40, 42, 44, 45, 46, 48, or 50 amino acid residues) in length having a sufficient affinity to the bone matrix, such that the bone-targeting moiety, singularly, has an in vivo binding affinity to the bone matrix that is from about $10^{-6}$ M to about $10^{-15}$ M (e.g., $10^{-7}$ M, $10^{-8}$ M, $10^{-9}$ M, $10^{-10}$ M, $10^{-11}$ M, $10^{-12}$ M, $10^{-13}$ M, $10^{-14}$ M, or $10^{-15}$ M). For example, the bone-targeting moiety can include a series of consecutive aspartate (D) and/or glutamate (E) residues, in which n=1 to 50, e.g., n=3-30, e.g., 5-15, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36, 38, 39, 40, 41, 42, 43, 44, 45, 46, 47, 48, 49, or 50.

The term "catalytically competent," as used herein, refers to a sALP that hydrolyzes the bone mineralization inhibitor inorganic pyrophosphate (PPi) to provide inorganic phosphate (Pi), thereby decreasing the extracellular concentrations of PPi. Thus, the catalytically competent sALP improves skeletal mineralization in bone by regulating the concentration of PPi.

By "extracellular domain" is meant any functional extracellular portion of the native protein, e.g., alkaline phosphatase. In particular, the extracellular domain lacks the signal peptide.

By "Fc" is meant a fragment crystallizable region of an immunoglobulin, e.g., IgG-1, IgG-2, IgG-3, IgG-3 or IgG-4, including the CH2 and CH3 domains of the immunoglobulin heavy chain. Fc may also include any portion of the hinge region joining the Fab and Fc regions. The Fc can be of any mammal, including human, and may be post-translationally modified (e.g., by glycosylation). In a non-limiting example, Fc can be the fragment crystallizable region of human IgG-1 having the amino acid sequence of SEQ ID NO: 20.

By "fragment" is meant a portion of a polypeptide or nucleic acid molecule that contains, preferably, at least 10%, 20%, 30%, 40%, 50%, 60%, 70%, 75%, 80%, 85%, 90%, 95%, 96%, 97%, 98%, 99%, or more of the entire length of the reference nucleic acid molecule or polypeptide. A fragment may contain, e.g., 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 400, 500, 600, 700, or more amino acid residues, up to the entire length of the polypeptide. Exemplary sALP fragments have amino acid residues 18-498, 18-499, 18-500, 18-501, 18-502, 18-503, 18-504, 18-505, 18-506, 18-507, 18-508, 18-509, 18-510, 18-511, or 18-512 of an ALP (e.g., SEQ ID NOs: 2-6), and may include additional C-terminal and/or N-terminal portions. Biological activity of such fragments is tested in standard assays known in the art, e.g., by a non-compartmental analysis (NCA) to calculate pharmacokinetic parameters of a sALP fragment.

By "naïve patient" is meant a patient having at least one symptom of neurofibromatosis type 1, having at least one symptom of dystrophic scoliosis, or in need of bone healing that has never received treatment with a sALP (such as TNALP, for example the sALP fusion polypeptide of SEQ ID NO: 1 or a polypeptide variant having at least 95% sequence identity to the sequence of SEQ ID NO: 1, e.g., asfotase alfa).

The terms "peptide," "polypeptide," and "protein" are used interchangeably and refer to any chain of two or more natural or unnatural amino acid residues, regardless of post-translational modification (e.g., glycosylation or phosphorylation), constituting all or part of a naturally-occurring or non-naturally occurring polypeptide or peptide, as is described herein.

By "pharmaceutically acceptable carrier" or "pharmaceutically acceptable excipient" is meant at least one carrier or excipient, respectively, which is physiologically acceptable to the treated patient while retaining the therapeutic properties of the compound with which it is administered. One exemplary pharmaceutically acceptable carrier substance is physiological saline. For instance, the pharmaceutically acceptable carrier can include sodium chloride (e.g., 150 mM sodium chloride) and sodium phosphate (e.g., 25 mM sodium phosphate). Other physiologically acceptable carriers and their formulations are known to those skilled in the art and described, e.g., in Remington's Pharmaceutical Sciences (20th edition), A. Gennaro, Ed., 2000, Lippincott, Williams & Wilkins, Philadelphia, PA.

By "pharmaceutical composition" is meant a composition containing a polypeptide or nucleic acid molecule as described herein formulated with at least one pharmaceutically acceptable excipient, diluent, or carrier. The pharmaceutical composition may be manufactured or sold with the approval of a governmental regulatory agency as part of a therapeutic regimen for the treatment or prevention of a disease or event in a patient. Pharmaceutical compositions can be formulated, for example, for subcutaneous administration, intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form.

The term "physiologically active," as used herein, refers to a sALP that hydrolyzes phosphoethanolamine (PEA), inorganic pyrophosphate (PPi), and pyridoxal 5'-phosphate (PLP) to provide Pi, thereby decreasing extracellular concentrations of PEA, PPi, and PLP.

The terms "sALP," "soluble alkaline phosphatase," and "extracellular domain of an alkaline phosphatase" are used interchangeably and refer to a soluble, non-membrane bound alkaline phosphatase (ALP) or a domain or a biologically active fragment of the soluble, non-membrane bound ALP. sALPs include, for example, an alkaline phosphatase lacking a C-terminal glycolipid anchor (GPI signal sequence, e.g., polypeptides including or consisting of the amino acid residues 18-502 of a human TNALP (SEQ ID NOs: 2, 3, 4, 5, or 6)). In particular, a TNALP may include, e.g., a polypeptide including or consisting of amino acid residues 1-485 of SEQ ID NO: 1, such as asfotase alfa, or a polypeptide variant having at least 95% sequence identity to the amino acid residues 1-485 of SEQ ID NO: 1. sALPs further include, for example, mammalian orthologs of human TNALP, such as a rhesus TNALP (SEQ ID NO: 7), a rat TNALP (SEQ ID NO: 8), a canine TNALP (SEQ ID NO: 9), a porcine TNALP (SEQ ID NO: 10), a murine TNALP (SEQ ID NO: 11), a bovine TNALP (SEQ ID NOs: 12-14), or a feline TNALP (SEQ ID NO: 15). sALPs also include soluble, non-membrane-bound forms of human PALP (e.g., polypeptides including or consisting of amino acid residues 18-502 of SEQ ID NOs: 16 or 17), GCALP (e.g., polypeptides including or consisting of amino acid residues 18-502 of SEQ ID NO: 18), and IALP (e.g., polypeptides including or consisting of amino acid residues 18-502 of SEQ ID NO: 19), and additional variants and analogs thereof that retain alkaline phosphatase activity, e.g., the ability to hydrolyze PPi. A sALP, in particular, lacks the N-terminal signal peptide (e.g., aa 1-17 of SEQ ID NOs: 2-6, 8, 11-13, or 15 or aa 1-25 of SEQ ID NO: 7).

By "sALP fusion polypeptide" is meant a polypeptide having the structure Z-sALP-Y-spacer-X-Wn-V, Z-Wn-X-spacer-Y-sALP-V, Z-sALP-Y-Wn-X-spacer-V, and Z-Wn-X-sALP-Y-spacer-V. In particular, the sALP fusion polypeptide can be Z-sALP-Y-spacer-X-Wn-V or Z-Wn-X-spacer-Y-sALP-V, such as hTNALP-Fc-D10 (e.g., asfotase alfa; the amino acid sequence SEQ ID NO: 1). Any one of X, Y, Z, V, the spacer, and/or Wn can be absent or an amino acid sequence of at least one amino acid. For example, X, Y, Z, and V may be a dipeptide sequence (e.g., leucine-lysine or aspartic acid-isoleucine), such as a two-residue linker at the Y position (e.g., leucine-lysine) and a two residue linker at the X position (e.g., aspartic acid-isoleucine). Spacers include, for example, a Fc region of an immunoglobulin, such as the amino acid sequence of SEQ ID NO: 20. Wn can be a bone-targeting moiety as defined herein, e.g., having a series of consecutive aspartate (D) or glutamate (E) residues, in which n=1 to 50, e.g., n=3-30, e.g., 5-15, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36, 38, 39, 40, 41, 42, 43, 44, 45, 46, 47, 48, 49, or 50.

By "signal peptide" is meant a short peptide (5-30 amino acids long) at the N-terminus of a polypeptide that directs a polypeptide towards the secretory pathway (e.g., the extracellular space). The signal peptide is typically cleaved during secretion of the polypeptide. The signal sequence may direct the polypeptide to an intracellular compartment or organelle, e.g., the Golgi apparatus. A signal sequence may be identified by homology, or biological activity, to a peptide with the known function of targeting a polypeptide to a particular region of the cell. One of ordinary skill in the art can identify a signal peptide by using readily available software (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). A signal peptide can be one that is, for example, substantially identical to amino acid residues 1-17 of SEQ ID NOs: 2-6 or amino acid residues 1-25 of SEQ ID NO: 7.

As used herein, when a polypeptide or nucleic acid sequence is referred to as having "at least X % sequence identity" to a reference sequence, wherein "X" is a real number, it is meant that at least X percent of the amino acid residues or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., *J. Mol. Biol.* 147:195-7, 1981) and BLAST (Basic Local Alignment Search Tool; Altschul et al., *J. Mol. Biol.* 215: 403-10, 1990). These and other alignment algorithms are accessible using publicly available computer software such as "Best Fit" (Smith and Waterman, *Advances in Applied Mathematics,* 482-489, 1981) as incorporated into GeneMatcher Plus (Schwarz and Dayhoff, *Atlas of Protein Sequence and Structure, Dayhoff,* M. O., Ed pp 353-358, 1979), BLAST, BLAST-2, BLAST-P, BLAST-N, BLAST-X, WU-BLAST-2, ALIGN, ALIGN-2, CLUSTAL, Megalign (DNASTAR), or other software/hardware for alignment. In addition, those skilled in the art can determine appropriate parameters for measuring alignment, including any algorithms needed to achieve optimal alignment over the length of the sequences being compared.

The terms "patient" or "subject" refer to a mammal, including, but not limited to, a human or a non-human mammal, such as a bovine, equine, canine, ovine, or feline.

"Parenteral administration," "administered parenterally," and other grammatically equivalent phrases, as used herein, refer to modes of administration other than enteral and topical administration, usually by injection, and include, without limitation, subcutaneous, intradermal, intravenous, intranasal, intraocular, pulmonary, intramuscular, intra-arterial, intrathecal, intracapsular, intraorbital, intracardiac, intradermal, intrapulmonary, intraperitoneal, transtracheal, subcuticular, intraarticular, subcapsular, subarachnoid, intraspinal, epidural, intracerebral, intracranial, intracarotid, and intrasternal injection and infusion.

By "therapeutically effective amount" is meant an amount of a polypeptide or nucleic acid molecule described herein that is sufficient to substantially improve, treat, prevent, delay, suppress, or arrest at least one symptom of neurofibromatosis type 1, at least one symptom of dystrophic scoliosis, or induce bone healing. A therapeutically effective amount of a composition described herein may depend on the severity of the disorder being treated and the condition, weight, and general state of the patient and can be determined by an ordinarily-skilled artisan with consideration of such factors. A therapeutically effective amount of a composition described herein can be administered to a patient in a single dose or in multiple doses administered over a period of time.

By "treating," "treat," or "treatment" is meant the medical management of a patient with the intent to cure, ameliorate, stabilize, reduce the likelihood of, or prevent at least one symptom of neurofibromatosis type 1, or at least one symptom of dystrophic scoliosis and/or management of a patient exhibiting or likely to have at least one symptom of neurofibromatosis type 1, or at least one symptom of dystrophic scoliosis, e.g., by administering a pharmaceutical composition. This term also means the medical management of a patient with the intent to cure, ameliorate, or stabilize a condition requiring bone healing and/or management of a patient exhibiting or likely to have a condition requiring bone healing, e.g., by administering a pharmaceutical composition. This term includes active treatment, that is, treatment directed specifically toward the improvement or associated with the cure of a disease, pathological condition, disorder, or event, and also includes causal treatment, that is, treatment directed toward removal of the cause of the associated disease, pathological condition, disorder, or event. In addition, this term includes palliative treatment, that is, treatment designed for the relief or improvement of at least one symptom rather than the curing of the disease, pathological condition, disorder, or event; symptomatic treatment, that is, treatment directed toward constitutional symptoms of the associated disease, pathological condition, disorder, or event; preventative treatment, that is, treatment directed to minimizing or partially or completely inhibiting the development of the associated disease, pathological condition, disorder, or event, e.g., in a patient who is not yet ill, but who is susceptible to, or otherwise at risk of, a particular disease, pathological condition, disorder, or event; and supportive treatment, that is, treatment employed to supplement another specific therapy directed toward the improvement of the associated disease, pathological condition, disorder, or event.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.8, 4, 5, etc.).

For any method disclosed herein that includes discrete steps, the steps may be conducted in any feasible order. And, as appropriate, any combination of two or more steps may be conducted simultaneously.

The above summary of the disclosure is not intended to describe each disclosed embodiment or every implementation of the disclosure. The description that follows more particularly exemplifies illustrative embodiments. In several places throughout the application, guidance may be provided through lists of examples, which examples can be used in various combinations. In each instance, the recited list serves only as a representative group and should not be interpreted as an exclusive list.

BRIEF DESCRIPTION OF THE DRAWINGS

FIG. 3A shows peripheral lucency of the left posterior iliac spine screw, denoted by an arrow.

FIG. 3B shows fracture of the left vertical connecting rod below the left L4 pedicle screw, denoted by an arrow.

FIG. 5A shows stable lucency around the left posterior iliac screw, denoted by an arrow. FIG. 5B shows fracture of outer cortex of the bone at the tip of the left posterior iliac screw, denoted by an arrow.

DETAILED DESCRIPTION

Figure 1:
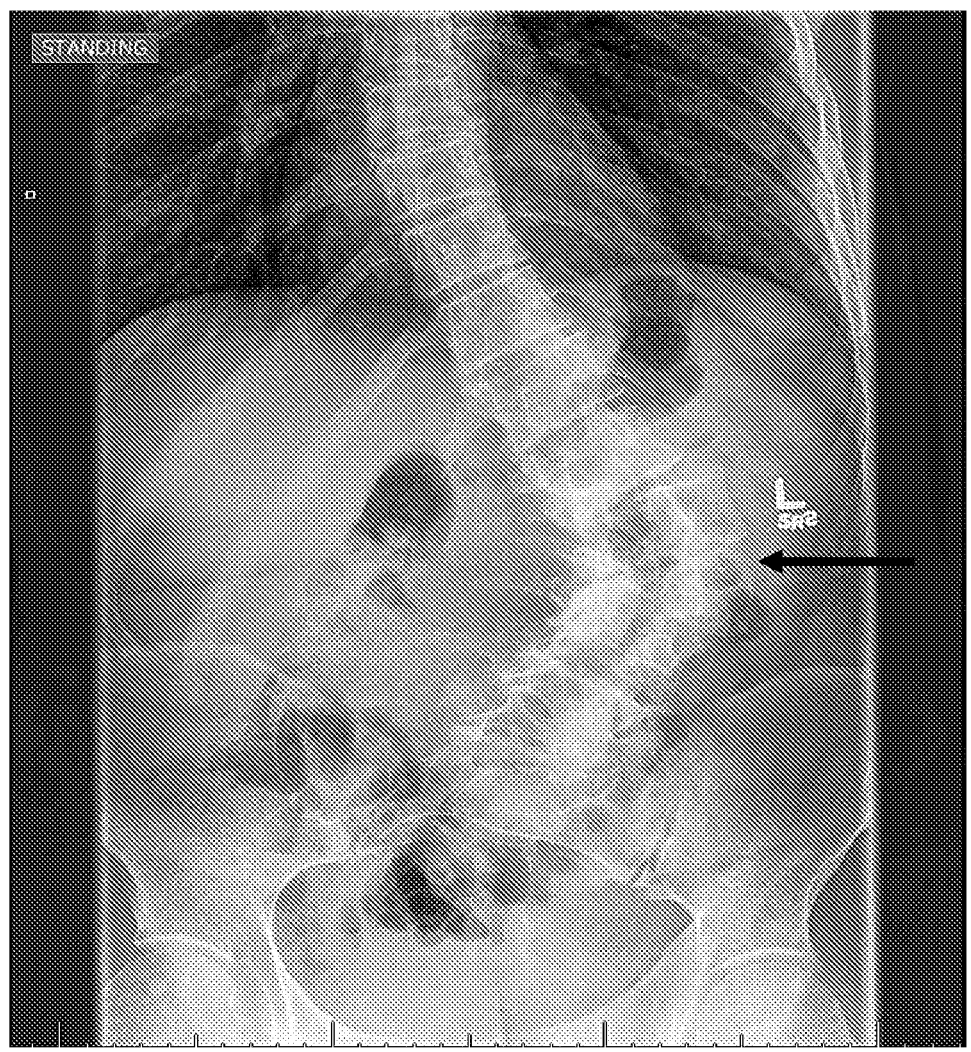
FIG. 1 is a radiograph showing severe dystrophic lumbar scoliosis in a 47 year old patient. The arrow points to the marked left convex dystrophic scoliosis of thoracolumbar spine with apex at L3. This radiograph shows a dystrophic curve because of the short, sharp angles, dural ectasia, vertebral body scalloping, vertebral wedging, and narrowed pedicles.

We have discovered several new and unexpected uses for asfotase alfa (SEQ ID NO: 1, STRENSIQ®, Alexion Pharmaceuticals, Inc.). Asfotase alfa, when combined with bone morphogenetic protein (BMP) and bisphosphonate therapy, resulted in solid arthrodesis after spinal surgery in a patient with NF1-related dystrophic scoliosis, where surgery combined with BMP therapy alone had previously failed. This result was unexpected because the patient was not deficient for tissue-nonspecific alkaline phosphatase, yet administration of the tissue-nonspecific alkaline phosphatase, asfotase alfa, resulted in solid arthrodesis. Thus, there was a synergistic effect when asfotase alfa was combined with surgical intervention, resulting in, for instance, improved postsurgical bone healing and/or mineralization. In one embodiment, asfotase alfa can be used to treat patients with one or more symptoms of neurofibromatosis type 1. In one embodiment, asfotase alpha can be used to treat patients with dystrophic scoliosis. In one embodiment, asfotase alfa can be used to promote bone healing. The use of asfotase alfa may occur in conjunction with a physical intervention, such as a surgical intervention. Optionally, the use of asfotase alfa occurs in conjunction with administration of one or more bone morphogenetic protein, one or more bisphosphonates, or a combination thereof.

Methods of Treatment

In some embodiments of the method, sALP (such as TNALP, for example the sALP fusion polypeptide of SEQ ID NO: 1 or a polypeptide variant described herein, such as a variant having at least 95% sequence identity to the sequence of SEQ ID NO: 1, e.g., asfotase alfa) is administered to a patient in an amount that is therapeutically effective to treat at least one symptom of neurofibromatosis type 1, e.g., spine curvature, kyphosis, osteoporosis, weakened vertebral bones, thinning of the ribs, rotation of the vertebrae, vertebral wedging, erosion of vertebrae. rotational or angular spinal deformity, dural ectasia, incomplete bone mineralization, elevated blood and/or urine levels of phosphoethanolamine (PEA), hypomineralization, hypercalciuria, short stature, skeletal deformity, waddling gait, bone pain, bone fracture, weakness, and calcium pyrophosphate dihydrate crystal deposition).

In some embodiments of the method, sALP (such as TNALP, for example the sALP fusion polypeptide of SEQ ID NO: 1 or a polypeptide variant having at least 80, 85%, 90%, 95%, 97%, 99%, or 100% sequence identity to the sequence of SEQ ID NO: 1, e.g., asfotase alfa) is administered to a patient in an amount that is therapeutically effective to treat at least one symptom of dystrophic scoliosis, for example NF1-related dystrophic scoliosis, e.g., shorter and more sharply angulated curves than seen in non-dystrophic scoliosis, bone abnormalities including thinning of the ribs, weakened vertebral bones, significant rotation of the vertebrae, vertebral wedging, and erosion of the vertebrae by the spinal fluid.

In one embodiment of the method, sALP (such as TNALP, for example the sALP fusion polypeptide of SEQ ID NO: 1 or a polypeptide variant having at least 80, 85%, 90%, 95%, 97%, 99%, or 100% sequence identity to the sequence of SEQ ID NO: 1, e.g., asfotase alfa) is administered to a patient in an amount that is therapeutically effective to induce bone healing. Examples of inducing bone healing includes treating a bone fracture and arthrodesis, the surgical fusion of two joints. For example, the method is useful to promote spinal fusion. Spinal fusion surgery can be used to eliminate bone-on-bone friction and/or to relive nerve compression that cause pain and other symptoms. Surgical bone fusion can also be used on fingers, ankles, and feet, for instance.

In some embodiments of the method, sALP (such as TNALP, for example the sALP fusion polypeptide of SEQ ID NO: 1 or a polypeptide variant described herein, such as a variant having at least 95% sequence identity to the sequence of SEQ ID NO: 1, e.g., asfotase alfa) is administered to a patient who has undergone an orthopedic surgery. The surgery may include at least one implant or hardware inserted during the surgery. The patient may be one that does not have neurofibromatosis type 1 (NF1), HPP, or craniosynostosis. The patient may have a disease or disorder, or may have one or more bone related conditions, such as spine curvature, kyphosis, osteoporosis, weakened vertebral bones, thinning of the ribs, rotation of the vertebrae, vertebral wedging, erosion of vertebrae. rotational or angular spinal deformity, dural ectasia, incomplete bone mineralization, elevated blood and/or urine levels of phosphoethanolamine (PEA), hypomineralization, hypercalciuria, short stature, skeletal deformity, waddling gait, bone pain, bone fracture, weakness, and calcium pyrophosphate dihydrate crystal deposition. In some embodiments, the patient has hardware inserted into bone that fails. The patient may have had one or more orthopedic surgeries (e.g., revision surgeries) in which implant fixation has failed. For example, the patient may have, or may be in need of, a craniofacial implant, dental implant, spinal implant, joint replacement part for hip, knee, shoulder, spine, elbow, or wrist, or a bone fixation material, such as a nail, screw, pin, nut, rod, and plate. The patient may also be in need of a revision surgery, in which a craniofacial implant, dental implant, spinal implant, joint replacement part for hip, knee, shoulder, spine, elbow, or wrist, or a bone fixation material, such as a nail, screw, pin, nut, rod, and plate, has failed.

Orthopedic surgeries that may include an implant or hardware include, for example, surgeries to the hand or upper extremity, shoulder, elbow, joint (e.g., total joint reconstruction, e.g., arthroplasty), foot, ankle, spine, musculoskeletal oncology related surgery, sports injury related surgery, trauma, and the like. Other common orthopedic surgeries that may include the use of hardware or an implant include, for example, arthroscopy of the knee, shoulder, hip, ankle, elbow, or wrist, fracture and meniscectomy, shoulder arthroscopy and decompression, carpal tunnel release, knee arthroscopy and chondroplasty, removal of support implant, knee arthroscopy and anterior cruciate ligament reconstruction, knee replacement, repair of femoral neck fracture, repair of trochanteric fracture, debridement of skin/muscle/bone/fracture, knee arthroscopy repair of one or both menisci, hip replacement, shoulder arthroscopy/distal clavicle excision, repair of rotator cuff tendon, repair fracture of radius (bone)/ulna, laminectomy, repair of ankle fracture (bimalleolar type), shoulder arthroscopy and debridement, lumbar spinal fusion, repair fracture of the distal part of radius, low back intervertebral disc surgery, incise finger tendon sheath, repair of ankle fracture (fibula), repair of femoral shaft fracture, and repair of trochanteric fracture. A patient who has undergone any of the foregoing orthopedic procedures may be treated with a sALP according to the methods described herein in order to improve the repair of the bone or to improve fixation of the implant or hardware.

The sALP may be used for repair of bone trauma or a bone defect that may have resulted from surgery or disease. The damaged or fragmented bone tissue may be reconstructed using an implant or hardware and supplemented by administration of a sALP before, during, or after a surgery to repair the defect. The implant or hardware, in combination with sALP administration, may further provide the necessary mechanical support for the remaining pieces of bone fragments at the site of damage and simultaneously allow blood and bone forming cells from adjacent tissues to penetrate the implant for improved healing. For example, the methods described herein can be used to repair calvarial bone defects after neurosurgical operations and traumas, in reconstructions of bony orbital floors and jaw bones. The methods described herein can also be used in orthopedics and spine surgery, as well as in fixation of fragmented pieces of bone and cosmetic surgeries. In the presence of long bones weakened by diseases, or when parts of the cortical bone are lost, the implant can be used to reinforce the long bones and cover openings where cortical bone is lost.

The methods described herein may also be used with bones of reduced quality (e.g., osteoporotic bone) or in revision surgeries (e.g., they can be used to replace previously inserted implants). The sALP (such as TNALP, for example the sALP fusion polypeptide of SEQ ID NO: 1 or a polypeptide variant described herein, such as a variant having at least 95% sequence identity to the sequence of SEQ ID NO: 1, e.g., asfotase alfa) can be used, for example, in osteosynthesis to internally stabilize and/or join bones, e.g., fractured (broken) bones, either in conjunction with mechanical stabilizing devices, such as metal plates, pins, rods, or wires, or individually.

The methods described herein may also be used to treat a bone defect in a patient with a fracture requiring compression. In particular, the sALP can be administered in conjunction with an implant that may be used to provide compressive fixation in a patient.

Bones that can be treated according to the methods described herein include, for example, subarticular fracture, a defect of the spine or vertebra, or a defect of the radius, ulna, fibula, clavicle, humerus, pelvis, femur, patella, tibia, talus, calcaneus, navicular, cuneiforms, metatarsals, metacarpals, phalanges, scapula, ankle, maxilla, or mandible. The implant or hardware can be positioned in proximity to the bone defect (e.g., positioning the implant so that it contacts the intraosseous space of a bone). The sALP (such as TNALP, for example the sALP fusion polypeptide of SEQ ID NO: 1 or a polypeptide variant described herein, such as a variant having at least 95% sequence identity to the sequence of SEQ ID NO: 1, e.g., asfotase alfa) may be administered at any time before, during, or after administration of the implant or hardware. The sALP may be coated on the implant or hardware.

Treatment methods of the invention also include maxillomandibular or craniofacial fixation, temporary fixation for repairing a bone defect in a staged reconstruction, glenoid or humeral fixation, patellar fixation, or spine fixation. For example, in spinal surgeries, the implant may be placed within a pedicle, used to anchor an interbody device, used to anchor spinal fusion plates and spacer replacement, used in an osteoporotic vertebra, or positioned in proximity to the spinous processes of adjacent vertebrae. The method may also include the insertion of a rod, pin, nail, or mesh or bone plate in proximity to the bone defect. The sALP may be administered at any time before, during, or after the surgery. The sALP may be coated on any implant or hardware.

Particular bone defects that may be treated using the methods described herein include, e.g., any bone deficient region, such as a void, gap, recess, or other discontinuity in a bone. The bone defect may be due to, for example, disease or trauma. The implants or hardware described herein can be applied, for example, in the repair of periodontal defects, in craniofacial or maxillofacial surgery or reconstruction, in cosmetic surgery, in hand surgery, in joint reconstruction, in fracture repair, in orthopedic surgical procedures, and in spinal fusion. The implants may also be used, for example, in osteosynthesis to internally stabilize and/or join bones, e.g., fractured (broken) bones, either in conjunction with other mechanical devices, such as washers (e.g., a washer of the invention), metal plates, pins, rods, or wires, or individually. For example, the implants can be used with a washer to provide compressive fixation of bone defects and bone fractures. In particular, the methods are useful for the treatment of defects or breaks in large bones. Non-limiting examples of bone fractures include, e.g., stable fractures, transverse fractures, oblique fractures, spiral fractures, comminuted fractures and open and displaced fractures. Exemplary large bones that may require fracture fixation include, e.g., the femur, tibia, fibula, humerus, ulna, radius, ribs, innominate bone (hip bone), and sternum. For each of these surgeries, the sALP may be administered at any time before, during, or after the surgery.

Surgical Intervention

Administration of sALP (such as TNALP, for example the sALP fusion polypeptide of SEQ ID NO: 1, or a polypeptide variant having at least 95% sequence identity to the sequence of SEQ ID NO: 1, e.g., asfotase alfa) in any of the disclosed methods can occur in conjunction with a physical intervention, for instance, surgical intervention. Surgical intervention can be used for arthrodesis, removal of bone, insertion of bone graft material, or setting a fractured bone. Surgical intervention can include instrumentation (e.g., implantation of hardware, such as screws, rods, plates, and metal cages) to aid in bone fusion. Surgical intervention can include traditional open surgery, such as open neck or open back surgery, a minimally invasive surgery, or a combination thereof.

Bone Morphogenetic Protein

Administration of sALP (such as TNALP, for example the sALP fusion polypeptide of SEQ ID NO: 1, or a polypeptide variant having at least 95% sequence identity to the sequence of SEQ ID NO: 1, e.g., asfotase alfa) in any of the disclosed methods can occur in conjunction with administration of bone morphogenetic protein (BMP). The use of BMP to induce bone formation and bone healing (e.g., arthrodesis or treating a bone fracture) is known. In one embodiment, treating at least one symptom of neurofibromatosis type 1, treating at least one symptom of dystrophic scoliosis, or inducing bone healing occurs in conjunction with administration of BMP. A BMP can be administered directly to the affected area, e.g., a bone fracture, or by subcutaneous, intramuscular, intravenous, oral, nasal, sublingual, intrathecal, or intradermal administration. In one embodiment, BMP is administered during a physical intervention, for instance, surgical intervention. The BMP can be any BMP effective to induce bone formation. Examples of useful BMPs are BMP-2, BMP-4, and BMP-7. BMP gene sequences, protein sequences, and methods for producing recombinant and naturally-derived BMPs are known in the art. BMPs may be administered on collagen absorbable sponges admixed with freeze dried crushed cancellous allograft bone.

Bisphosphonates

Administration of sALP (such as TNALP, for example the sALP fusion polypeptide of SEQ ID NO: 1 or a polypeptide variant having at least 95% sequence identity to the sequence of SEQ ID NO: 1, e.g., asfotase alfa) in any of the disclosed methods can occur in conjunction with administration of at least one bisphosphonate. In one embodiment, treating at least one symptom of neurofibromatosis type 1, treating at least one symptom of dystrophic scoliosis, or inducing bone healing occurs in conjunction with administration of at least one bisphosphonate. The use of at least one bisphosphonate to prevent the loss of bone density is known in the art and routine. Examples of bisphosphonates include, but are not limited to, zolendronic acid and pamidronate.

In one embodiment, at least one bisphosphonate is administered during or after a physical intervention, for instance, surgical intervention. For instance, at least one bisphosphonate can be provided in either a single or multiple dosage regimens. One or more doses can be administered, e.g., hourly, every other hour, daily, every other day, twice a week, three times a week, four times a week, five times a week, six times a week, weekly, biweekly, monthly, bimonthly, or yearly. Alternatively, doses can be administered, e.g., twice, three times, four times, five times, six times, seven times, eight times, nine times, 10 times, 11 times, or 12 times per day. In one embodiment, the dosing regimen is a single administration. The duration of the dosing regimen can be, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day(s), week(s), or month(s). In one embodiment, the administration can begin 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day(s), week(s), or month(s) after the physical intervention, for instance, surgical intervention. The at least one bisphosphonate can be delivered at a dosage of, e.g., 0.01, 0.05, 0.1, 0.5, 1, 2, 2.5, 5, 10, 20, 25, 50, 100, 125, 150, 200, 250, or 500 mg/kg; or 1, 2, 2.5, 5, 10, 20, 25, 50, 100, 125, 150, 200, 250, 500, 750, 900, or 1,000 mg/kg. The at least one bisphosphonate can be administered by subcutaneous, intramuscular, intravenous, oral, nasal, sublingual, intrathecal, or intradermal administration. In one embodiment, the pharmaceutical composition is formulated for intravenous administration. The amount, frequency, and duration of dosage will be adapted by the clinician in accordance with conventional factors presented by the patient, such as the symptoms of the neurofibromatosis type 1, the dystrophic scoliosis, the need for bone healing/mineralization, and different parameters from the patient.

Evaluation of Treatment Efficacy

Exemplary metrics useful for evaluating the efficacy of treatment using a sALP (such as TNALP, for example the sALP fusion polypeptide of SEQ ID NO: 1 or a polypeptide variant having at least 95% sequence identity to the sequence of SEQ ID NO: 1, e.g., asfotase alfa) include (1) bone healing, (2) bone mineralization, (3) bone mineral density, and (4) plasma PPi and PLP concentrations. The methods may further include the use of one or more of the described metrics (e.g., bone healing, mineralization, bone mineral density, or plasma PPi and PLP concentrations), singly or in combination, to assess treatment efficacy, in which improvements as described herein demonstrate that sALP is an effective treatment for the treated condition.

Additionally, the method may further include changing the dosage and/or frequency of sALP (e.g., SEQ ID NO: 1; e.g., asfotase alfa) administration in order to determine the effective amount of sALP to administer to patient in need thereof.

Bone Healing and Mineralization

In some instances, administration of sALP (such as TNALP, for example the sALP polypeptide of SEQ ID NO: 1, or a polypeptide variant described herein, such as a variant having at least 95% sequence identity to the sequence of SEQ ID NO: 1, e.g., asfotase alfa) according to the disclosure results in an increase in bone healing in the patient following the treatment. An increase in bone healing results in new bone, and includes the increased mineralization to result in the union of two or more bones (e.g., fusion of two normally separate bones, or union of two portions of a bone that have been separated by a fracture), or increased bone healing near instrumentation. Methods for identifying an increase in bone healing and mineralization are routine and include non-invasive techniques such as radiography and computed tomography (CT). Typically, images of the relevant area of the patient are taken before and at one or more time points following the treatment method, and the images are compared. Increased bone healing and/or mineralization can be identified as increased opacity. Thus, successful arthrodesis can be identified as increased opacity after treatment between two bones targeted for fusion. Reduced loosening of hardware in bone, e.g., screws, can be identified as increased opacity in the bone surrounding, e.g., anchoring, the instrumentation. Pre-treatment images can be taken at any time before the treatment method begins, and can be timed to be 1, 2, 3, 4, 5, or 6 day(s), week(s), or month(s) before treatment is initiated. Post-treatment images can be taken 1, 2, 3, 4, 5, 6, 7, 8, 9, 10, 11, or 12 day(s), week(s), month(s), or year(s) after treatment is initiated. The increase in bone healing and/or mineralization in the patient may become detectable at least 1, 2, 3, 4, 5, 6, 7, 8, 9, 10, 11, or 12 week(s) or month(s) following a treatment period. The increase in bone healing and/or mineralization in the patient may in some cases be sustained for at least 1, 2, 3, 4, 5, 6, 7, 8, 9, 10, 11, or 12 week(s), month(s), or year(s) following a treatment period. A reference bone can be one or more specific bones. In one embodiment, the reference point is the one or more specific bones being fused (e.g., tibia, radius, ulna, and spinal bones, e.g., vertebrae, e.g., cervical spine C1-C7, thoracic spine T1-T12, lumbar spine L1-L5, sacrum S1-S5, and coccyx). by a disclosed method. In one embodiment, the reference point is the specific bone having a fracture that is being treated by a disclosed method. In one embodiment, the reference point is the bone surrounding instrumentation.

Bone Mineral Density (BMD)

In some instances, administration of sALP (such as TNALP, for example the sALP polypeptide of SEQ ID NO: 1, or a polypeptide variant having at least 95% sequence identity to the sequence of SEQ ID NO: 1, e.g., asfotase alfa) according to the disclosure results in a limited change in BMD in the patient following the treatment. Methods for measuring BMD are known and include, for instance, bone biopsy, dual-energy X-ray absorptiometry (DXA or DEXA), peripheral quantitative CT (pQCT), high-resolution pQCT (HR-pQCT), and quantitative ultrasound (QUS). Measurement can be by any method, including CT Hounsfield measurement, and can use comparison of results to a normative database or control patient. BMD is typically reported as a Z-score or a T-score. Pre-treatment BMD values can be measured at any time before the treatment method begins, and can be timed to be 1, 2, 3, 4, 5, 6, 7, 8, 9, 10, 11, or 12 day(s), week(s), month(s), or year(s) before treatment is initiated. Post-treatment BMD values can be measured 1, 2, 3, 4, 5, 6, 7, 8, 9, 10, 11, or 12 day(s), week(s), month(s), or year(s) after treatment is initiated. In one embodiment, the BMD value of a reference point after treatment is decreased by no greater than 0.01%, 0.05%, 0.1%, 0.5%, 1%. In one embodiment, the BMD value of a reference point after treatment is increased by at least 0.01%, 0.05%, 0.1%, 0.5%, or 1%. In one embodiment, the change in a BMD value of a reference point after treatment is unchanged, or a change is undetectable. The change in BMD of the patient may in some cases be sustained following a treatment period for at least 1, 2, 3, 4, 5, 6, 7, 8, 9, 10, 11, or 12 day(s), week(s), month(s), or year(s) or years or more. A reference point can be, e.g., one or more specific bones. In one embodiment, the reference point is the one or more specific bone(s) being treated by a disclosed method.

PPi and PLP Concentrations

The average decrease in PPi concentrations in a plasma sample from the patient to whom the sALP or sALP polypeptide (such as TNALP, for example the sALP polypeptide of SEQ ID NO: 1 or a polypeptide variant having at least 95% sequence identity to the sequence of SEQ ID NO: 1, e.g., asfotase alfa) is administered according to the disclosure may be about 25% or greater (e.g., 30%, 35%, 40%, 45%, 50%, 55%, 60%, or more than 60%) relative to PPi concentrations in a plasma sample from the patient prior to administration of the sALP. The average decrease in PPi concentrations in a plasma sample from the patient may in some cases be sustained during a treatment period of at least one week, six months, or up to one year or more. Typically, the decrease is sustained for the duration of the treatment period with asfotase alfa.

The average decrease in PLP concentrations in a plasma sample from the patient to whom the sALP or sALP polypeptide (such as TNALP, for example the sALP polypeptide of SEQ ID NO: 1 or a polypeptide variant having at least 95% sequence identity to the sequence of SEQ ID NO: 1, e.g., asfotase alfa) is administered may be about 50% or greater (e.g., 55%, 60%, 65%, 70%, 75%, 80%, 85%, 90%, 95%, or more than 95%) relative to PLP concentrations in a plasma sample from the patient prior to administration of the sALP. The average decrease in PLP concentrations in a plasma sample from the patient may in some cases be sustained during a treatment period of at least one week and up to one year or more. Typically, the decrease is sustained for the duration of the treatment period with asfotase alfa.

Alkaline Phosphatase

Asfotase alfa is a human TNALP (hTNALP; SEQ ID NO: 1) fusion polypeptide. In particular, asfotase alfa (SEQ ID NO: 1) can be used effectively to treat at least one symptom of neurofibromatosis type 1, treat at least one symptom of dystrophic scoliosis, or induce bone healing, and physical impairments associated therewith.

Given the results described herein, the treatment methods are not limited to administration of a particular alkaline phosphatase (ALP) or nucleic acid sequence encoding an ALP. Alkaline phosphatases encompass a group of enzymes that catalyze the cleavage of a phosphate moiety (e.g., hydrolysis of pyrophosphate, PPi). There are four known mammalian alkaline phosphatase (ALP) isozymes: tissue nonspecific alkaline phosphatase (TNALP; described further below), placental alkaline phosphatase (PLALP) (e.g., Accession Nos. P05187, NP_112603, and NP_001623), germ cell alkaline phosphatase (GALP) (e.g., Accession No. P10696), and intestinal alkaline phosphatase (IALP) (e.g., Accession Nos. P09923 and NP_001622). In addition to the exemplary ALPs discussed herein, any polypeptide having the identical or similar catalytic site structure and/or enzymatic activity of ALP can be used (e.g., as a sALP or a sALP fusion polypeptide as defined herein) in a method disclosed herein. Bone delivery conjugates including sALP are further described in PCT Publication Nos: WO 2005/103263 and WO 2008/138131.

TNALPs that can be used according to the methods described herein include, e.g., human TNALP (Accession Nos. NP_000469, AA10910, AAH90861, AAH66116, AAH21289, and AAI26166), rhesus TNALP (Accession No. XP_01109717), rat TNALP (Accession No. NP_037191), dog TNALP (Accession No. AAF64516), pig TNALP (Accession No. AAN64273), mouse (Accession No. NP_031457), cow TNALP (Accession Nos. NP_789828, NP_776412, AAM 8209, and AAC33858), and cat TNALP (Accession No. NP_001036028). In particular, TNALP can be a recombinant human TNALP (e.g., SEQ ID NO: 1, asfotase alfa; see U.S. Pat. Nos. 7,763,712 and 7,960,529) used in a method disclosed herein. The TNALP can also be one that exhibits at least about 95% sequence identity to the polypeptide or nucleic acid sequence of the above-noted TNALPs.

Soluble Alkaline Phosphatases

An ALP that can be used in the methods described herein includes soluble (e.g., extracellular or non-membrane-bound) forms of any of the alkaline phosphatases described herein. The sALP can be, for example, a soluble form of human tissue non-specific alkaline phosphatase (human TNALP (hTNALP)). The methods are not limited to a particular sALP and can include any sALP that is physiologically active toward, e.g., phosphoethanolamine (PEA), inorganic pyrophosphate (PPi), and pyridoxal 5'-phosphate (PLP). In particular, a sALP is one that is catalytically competent to improve skeletal mineralization in bone. The methods further include nucleic acids encoding the sALPs described herein that can be used in a method described herein.

TNALP is a membrane-bound protein anchored by a glycolipid moiety at the C-terminal (Swiss-Prot, P05186). This glycolipid anchor (GPI) is added post-translationally after the removal of a hydrophobic C-terminal end, which serves both as a temporary membrane anchor and as a signal for the addition of the GPI. While the GPI anchor is located in the cell membrane, the remaining portions of TNALP are extracellular. In particular, TNALP (e.g., human TNALP (hTNALP)) can be engineered to replace the first amino acid of the hydrophobic C-terminal sequence (an alanine) with a stop codon, thereby producing an engineered hTNALP that contains all amino acid residues of the native anchored form of TNALP and lacks the GPI membrane anchor. One skilled in the art will appreciate that the position of the GPI membrane anchor will vary in different ALPs and can include, e.g., the last 10, 12, 14, 16, 18, 20, 21, 22, 23, 24, 25, 26, 27, 28, 29, 30, 32, 34, 36, 38, 40, 45, 50, or more amino acid residues on the C-terminus of the polypeptide. Recombinant sTNALP can include, e.g., amino acids 1 to 502 (18 to 502 when secreted), amino acids 1 to 501 (18 to 501 when secreted), amino acids 1 to 504 (18 to 504 when secreted), amino acids 1 to 505 (18-505 when secreted), or amino acids 1 to 502. Thus, the C-terminal end of the native ALP can be truncated by certain amino acids without affecting ALP activity.

In addition to the C-terminal GPI anchor, TNALP also has an N-terminal signal peptide sequence. The N-terminal signal peptide is present on the synthesized protein when it is synthesized, but cleaved from TNALP after translocation into the ER. The sALPs include both secreted (i.e., lacking the N-terminal signal) and non-secreted (i.e., having the N-terminal signal) forms thereof. One skilled in the art will appreciate that the position of the N-terminal signal peptide will vary in different alkaline phosphatases and can include, for example, the first 5, 8, 10, 11, 12, 13, 14, 15, 16, 17, 18, 19, 20, 21, 22, 23, 24, 25, 27, 30, or more amino acid residues on the N-terminus of the polypeptide. One of skill in the art can predict the position of a signal sequence cleavage site, e.g., by an appropriate computer algorithm such as that described in Bendtsen et al. (J. Mol. Biol. 340(4):783-795, 2004) and available on the Web at www.cbs.dtu.dk/services/SignalP/.

The methods can also be performed using sALP consensus sequences derived from the extracellular domain of ALP isozymes (e.g., TNALP, PALP, GCALP, IALP, etc.). Thus, similar to sTNALP discussed above, the present disclosure also provides other soluble human ALP isozymes, i.e., without the peptide signal, preferably comprising the extracellular domain of the ALPs. The sALPs also include polypeptide sequences satisfying a consensus sequence derived from the ALP extracellular domain of human ALP isozymes and of mammalian TNALP orthologs (human, mouse, rat, cow, cat, and dog) or a consensus derived from the ALP extracellular domain of just mammalian TNALP orthologs (human, mouse, rat, cow, cat, and dog). The sALPs also include those which satisfy similar consensus sequences derived from various combinations of these TNALP orthologs or human ALP isozymes. Such consensus sequences are given, for example, in WO 2008/138131.

sALPs of the present methods can include not only the wild-type sequence of the sALPs described above, but any polypeptide having at least 50% (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more) sequence identity to these alkaline phosphatases (e.g., SEQ ID NOs: 1-19; for example the sALP fusion polypeptide of SEQ ID NO: 1 or a polypeptide variant having at least 95% sequence identity to the sequence of SEQ ID NO: 1, e.g., asfotase alfa). Examples of mutations that can be introduced into an ALP sequence are described in US Publication No. 2013/0323244. A sALP can optionally be glycosylated at any appropriate one or more amino acid residues. In addition, an sALP can have at least 50% (e.g., 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more) sequence identity to any of the sALPs described herein (such as TNALP, for example the sALP fusion polypeptide of SEQ ID NO: 1 or a polypeptide variant having at least 95% sequence identity to the sequence of SEQ ID NO: 1, e.g., asfotase alfa). A sALP can have 1, 2, 3, 4, 5, 6, 7, 8, 9, 10, or more additions, deletions, or substitutions relative to any of the sALPs described herein (such as TNALP, for example the sALP fusion polypeptide of SEQ ID NO: 1 or a polypeptide variant having at least 95% sequence identity to the sequence of SEQ ID NO: 1, e.g., asfotase alfa).

sALP Fusion Polypeptides

Any of the sALPs (such as TNALP, for example the sALP fusion polypeptide of SEQ ID NO: 1 or a polypeptide variant having at least 95% sequence identity to the sequence of SEQ ID NO: 1, e.g., asfotase alfa), linkers, spacers (e.g., Fc regions), and bone-targeting moieties described herein can be combined in a fusion polypeptide, which includes the structures Z-sALP-Y-spacer-X-Wn-V, Z-Wn-X-spacer-Y-sALP-V, Z-sALP-Y-Wn-X-spacer-V, and Z-Wn-X-sALP-Y-spacer-V. In particular, the structure of the sALP fusion polypeptide can be Z-sALP-Y-spacer-X-Wn-V or Z-Wn-X-spacer-Y-sALP-V. The sALP of the sALP fusion polypeptide can be the full-length ALP or functional fragments of ALPs, such as the soluble, extracellular domain of the ALP, as is described herein (e.g., TNALP, PALP, GCALP and IALP).

Any one of X, Y, Z, and V and/or the spacer can be absent or a linker region including an amino acid sequence of at least one amino acid. For example, X, Y, Z, and V may be a dipeptide sequence (e.g., leucine-lysine or aspartic acid-isoleucine), such as a two residue linker at the Y position (e.g., leucine-lysine) or a two residue linker at the X position (e.g., aspartic acid-isoleucine). For example, sALP fusion polypeptides can have the structure hTNALP-Fc-D10 (e.g., a sALP fusion polypeptide including the amino acid sequence of SEQ ID NO: 1 or a polypeptide variant having at least 95% sequence identity to the sequence of SEQ ID NO: 1, e.g., asfotase alfa).

The linker region can be of any sequence and length that allows the sALP to remain biologically active, e.g., not sterically hindered. Exemplary linker lengths are between 1 and 200 amino acid residues, e.g., 1-5, 6-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, or 191-200 amino acid residues. For instance, linkers include or consist of flexible portions, e.g., regions without significant fixed secondary or tertiary structure. Exemplary flexible linkers are glycine-rich linkers, e.g., containing at least 50%, 60%, 65%, 70%, 75%, 80%, 85%, 90%, 95%, or even 100% glycine residues. Linkers can also contain, e.g., serine residues. In some cases, the amino acid sequence of linkers consists only of glycine and serine residues. A linker can optionally be glycosylated at any appropriate one or more amino acid residues. Additionally, a linker as described herein can include any other sequence or moiety, attached covalently or non-covalently. The linker can also be absent, in which the spacer (e.g., the Fc region) and the sALP are fused together directly, with no intervening residues.

Useful spacers include, but are not limited to, polypeptides comprising an Fc region. For example, a sALP can be a fusion polypeptide including an Fc region of an immunoglobulin at the N-terminal or C-terminal domain. An immunoglobulin molecule has a structure that is well known in the art. It includes two light chains (~23 kD each) and two heavy chains (~50-70 kD each) joined by inter-chain disulfide bonds. Immunoglobulins are readily cleaved proteolytically (e.g., by papain cleavage) into Fab (containing the light chain and the VH and CH1 domains of the heavy chain) and Fc (containing the CH2 and CH3 domains of the heavy chain, along with adjoining sequences). Useful Fc fragments as described herein include the Fc fragment of any immunoglobulin molecule, including IgG, IgM, IgA, IgD, or IgE, and their various subclasses (e.g., IgG-1, IgG-2, IgG-3, IgG-4, IgA-1, IgA-2), from any mammal (e.g., human). For instance, the Fc fragment is human IgG-1. The Fc fragments can include, for example, the CH2 and CH3 domains of the heavy chain and any portion of the hinge region. The Fc region can optionally be glycosylated at any appropriate one or more amino acid residues known to those skilled in the art. In particular, the Fc fragment of the fusion polypeptide has the amino acid sequence of SEQ ID NO: 20, or has at least 50% (e.g., 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more) sequence identity to SEQ ID NO: 20. Engineered, e.g., non-naturally occurring, Fc regions can be incorporated into the sALP fusion polypeptides described herein, e.g., those described in WO 2005/007809. An Fc fragment as described herein can have 1, 2, 3, 4, 5, 6, 7, 8, 9, 10, 11, 12, 13, 14, 15, 16, 17, 18, 19, 20, 25, 30, 35, 40, 50, or more additions, deletions, or substitutions relative to any of the Fc fragments described herein.

Wn can be a bone-targeting moiety, e.g., having a series of consecutive aspartate (D) or glutamate (E) residues, in which n=1 to 50, e.g., n=3-30, e.g., 5-15, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 38, 39, 40, 41, 42, 43, 44, 45, 46, 47, 48, 49, or 50. The bone-targeting moiety, if present, can be positioned anywhere in the fusion polypeptide, e.g., at or near the N-terminal or C-terminal end, and/or in the linker region. For instance, the bone-targeting moiety can be present at the C-terminal end of a sALP fusion polypeptide. sALPs and fusion polypeptides can also lack a bone-targeting moiety.

Additional amino acid residues can be introduced into the polypeptide according to the cloning strategy used to produce the fusion polypeptides. For instance, the additional amino acid residues do not provide an additional GPI anchoring signal so as to maintain the polypeptide in a soluble form. Furthermore, any such additional amino acid residues, when incorporated into the polypeptide of the methods, do not provide a cleavage site for endoproteases of the host cell. The likelihood that a designed sequence would be cleaved by the endoproteases of the host cell can be predicted as described, e.g., by Ikezawa (*Biol. Pharm. Bull.* 25:409-417, 2002).

The sALP fusion polypeptides (such as a TNALP, for example the sALP fusion polypeptide of SEQ ID NO: 1 or a polypeptide variant having at least 95% sequence identity to the sequence of SEQ ID NO: 1, e.g., asfotase alfa) can be associated into dimers or tetramers. For example, two sALP-Fc monomers can be covalently linked through two disulfide bonds located in the hinge regions of the Fc fragments. Additionally, the sALP fusion polypeptide (e.g., a sALP or a sALP fusion polypeptide) can be glycosylated or PEGylated.

Production of Nucleic Acids and Polypeptides

The nucleic acids encoding sALPs (such as TNALP, for example the sALP fusion polypeptide of SEQ ID NO: 1 or a polypeptide variant having at least 95% sequence identity to the sequence of SEQ ID NO: 1, e.g., asfotase alfa) can be produced by any method known in the art. Typically, a nucleic acid encoding the desired fusion polypeptide is generated using molecular cloning methods, and is generally placed within a vector, such as a plasmid or virus. The vector is used to transform the nucleic acid into a host cell appropriate for the expression of the fusion polypeptide. Representative methods are disclosed, for example, in Maniatis et al. (Cold Springs Harbor Laboratory, 1989). Many cell types can be used as appropriate host cells, although mammalian cells are preferable because they are able to confer appropriate post-translational modifications. Host cells can include, e.g., Chinese Hamster Ovary (CHO) cell, L cell, C127 cell, 3T3 cell, BHK cell, COS-7 cell or any other suitable host cell known in the art. For example, the host cell is a Chinese Hamster Ovary (CHO) cell (e.g., a CHO-DG44 cell).

The sALPs (such as TNALP, for example the sALP fusion polypeptide of SEQ ID NO: 1 or a polypeptide variant having at least 95% sequence identity to the sequence of SEQ ID NO: 1, e.g., asfotase alfa) can be produced under any conditions suitable to effect expression of the sALP polypeptide in the host cell. Such conditions include appropriate selection of a media prepared with components such as a buffer, bicarbonate and/or HEPES, ions like chloride, phosphate, calcium, sodium, potassium, magnesium, iron, carbon sources like simple sugars, amino acids, potentially lipids, nucleotides, vitamins and growth factors like insulin; regular commercially available media like alpha-MEM, DMEM, Ham's-F12, and IMDM supplemented with 2-4 mM L-glutamine and 5% Fetal bovine serum; regular commercially available animal protein free medialike Hyclone™ SFM4CHO, Sigma CHO DHFR-, Cambrex POWER™ CHO CD supplemented with 2-4 mM L-glutamine. These media are desirably prepared without thymidine, hypoxanthine and L-glycine to maintain selective pressure, allowing stable protein-product expression.

Patient Treated by the Methods

The patient to whom sALP is administered can be of any age, but particularly can be an adolescent, e.g., a person of about 12 to about 18 years of age, or an adult older than about 18 years of age. The patient may be afflicted with at least one symptom of neurofibromatosis type 1. The patient may be afflicted with dystrophic scoliosis. The patient may be in need of induced bone healing and/or mineralization. For instance, the patient may be afflicted with one or more bone fractures, such as fractures in spinal bones, e.g., vertebrae. The patient may have at least one symptom of dystrophic scoliosis, including NF1-related dystrophic scoliosis.

Administration and Dosage

In any of the disclosed methods, any amount of a pharmaceutical composition (e.g., including a sALP or sALP fusion polypeptide, such as TNALP, for example the sALP polypeptide of SEQ ID NO: 1 or a polypeptide variant described herein, such as a variant having at least 80, 85%, 90%, 95%, 97%, 99%, or 100% sequence identity to the sequence of SEQ ID NO: 1, e.g., asfotase alfa) can be administered to a patient. The dosages will depend on many factors including the mode of administration and the age of the patient. Typically, the amount of the composition (e.g., a sALP or sALP fusion polypeptide, such as TNALP, for example the sALP polypeptide of SEQ ID NO: 1 or a polypeptide variant having at least 95% sequence identity to the sequence of SEQ ID NO: 1, e.g., asfotase alfa) contained within a single dose will be an amount that is effective to treat a patient described herein without inducing significant toxicity.

For example, in any of the disclosed methods the sALP (such as TNALP, for example the sALP polypeptide of SEQ ID NO: 1 or a polypeptide variant having at least 95% sequence identity to the sequence of SEQ ID NO: 1, e.g., asfotase alfa) described herein can be administered to a patient in individual doses ranging, e.g., from 0.01 mg/kg to 500 mg/kg (e.g., from 0.05 mg/kg to 500 mg/kg, from 0.1 mg/kg to 20 mg/kg, from 5 mg/kg to 500 mg/kg, from 0.1 mg/kg to 100 mg/kg, from 10 mg/kg to 100 mg/kg, from 0.1 mg/kg to 50 mg/kg, from 0.5 mg/kg to 25 mg/kg, from 1.0 mg/kg to 10 mg/kg, from 1.5 mg/kg to 5 mg/kg, or from 2.0 mg/kg to 3.0 mg/kg) or from 1 µg/kg to 1,000 µg/kg (e.g., from 5 µg/kg to 1,000 µg/kg, from 1 µg/kg to 750 µg/kg, from 5 µg/kg to 750 µg/kg, from 10 µg/kg to 750 µg/kg, from 1 µg/kg to 500 µg/kg, from 5 µg/kg to 500 µg/kg, from 10 µg/kg to 500 µg/kg, from 1 µg/kg to 100 µg/kg, from 5 µg/kg to 100 µg/kg, from 10 µg/kg to 100 µg/kg, from 1 µg/kg to 50 µg/kg, from 5 µg/kg to 50 µg/kg, or from 10 µg/kg to 50 µg/kg).

Exemplary doses of a sALP include, e.g., 0.01, 0.05, 0.1, 0.5, 1, 2, 2.5, 5, 10, 20, 25, 50, 100, 125, 150, 200, 250, or 500 mg/kg; or 1, 2, 2.5, 5, 10, 20, 25, 50, 100, 125, 150, 200, 250, 500, 750, 900, or 1,000 µg/kg. For all dosages or ranges recited herein, the term "about" can be used to modify these dosages by ±10% of the recited values or range endpoints. In particular, compositions (e.g., including sALP (such as TNALP, for example the sALP polypeptide of SEQ ID NO: 1 or a polypeptide variant having at least 95% sequence identity to the sequence of SEQ ID NO: 1, e.g., asfotase alfa)) in accordance with the present disclosure can be administered to a patient in doses ranging from about 0.001 mg/kg/day to about 500 mg/kg/day, about 0.01 mg/kg/day to about 100 mg/kg/day, or about 0.01 mg/kg/day to about 20 mg/kg/day. For example, the sALP compositions (such as TNALP, for example the sALP polypeptide of SEQ ID NO: 1 or a polypeptide variant having at least 95% sequence identity to the sequence of SEQ ID NO: 1, e.g., asfotase alfa) can be administered to a patient in a weekly dosage ranging, e.g., from about 0.5 mg/kg/week to about 140 mg/kg/week, e.g., about 0.8 mg/kg/week to about 50 mg/kg/week, or about 1 mg/kg/week to about 10 mg/kg/week (e.g., about 3 or about 6 or about 9 mg/kg/week). In particular, the sALP (such as TNALP, for example the sALP polypeptide of SEQ ID NO: 1 or a polypeptide variant having at least 95% sequence identity to the sequence of SEQ ID NO: 1, e.g., asfotase alfa) can be administered at a dosage of 2 mg/kg three times a week (total dose about 6 mg/kg/week), 1 mg/kg six times a week (total dose about 6 mg/kg/week), 3 mg/kg three times a week (total dose 9 mg/kg/week), 0.5 mg/kg three times a week (total dose of 1.5 mg/kg/week), or 9.3 mg/kg three times a week (total dose about 28 mg/kg/week). The dosage will be adapted by the clinician in accordance with conventional factors such as, for instance, the extent of the neurofibromatosis type 1, the dystrophic scoliosis, the need for bone healing, and different parameters from the patient.

Dosages of pharmaceutical compositions including sALPs (such as TNALP, for example the sALP polypeptide of SEQ ID NO: 1 or a polypeptide variant having at least 95% sequence identity to the sequence of SEQ ID NO: 1, e.g., asfotase alfa) can be provided in either a single or multiple dosage regimens. Doses can be administered, e.g., hourly, bihourly, daily, bidaily, twice a week, three times a week, four times a week, five times a week, six times a week, weekly, biweekly, monthly, bimonthly, or yearly. Alternatively, doses can be administered, e.g., twice, three times, four times, five times, six times, seven times, eight times, nine times, 10 times, 11 times, or 12 times per day. In particular, the dosing regimen is three times a week. The duration of the dosing regimen can be, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day(s), week(s), or month(s). The dosing regimen can begin before, during, or after a physical intervention, such as a surgical intervention. The amount, frequency, and duration of dosage will be adapted by the clinician in accordance with conventional factors such as the extent of the neurofibromatosis type 1, the dystrophic scoliosis, the bone fracture, or bone mineralization, and different parameters from the patient.

For example, a sALP or sALP fusion polypeptide (such as TNALP, for example the sALP polypeptide of SEQ ID NO: 1 or a polypeptide variant having at least 95% sequence identity to the sequence of SEQ ID NO: 1, e.g., asfotase alfa) can be formulated as a solution for injection, which is a clear, colorless to slightly yellow, aqueous solution, pH 7.4. The sALP (such as TNALP, for example the sALP polypeptide of SEQ ID NO: 1 or a polypeptide variant having at least 95% sequence identity to the sequence of SEQ ID NO: 1, e.g., asfotase alfa) may be formulated at a concentration of, for instance, 12 mg/0.3 mL, 18 mg/0.45 mL, 28 mg/0.7 mL, 40 mg/1 ml, or 80 mg/0.8 mL. In particular, the composition can be formulated as a 40 mg/ml solution for injection, in which each ml of solution contains 40 mg of sALP (e.g., each vial contains 0.3 ml solution and 12 mg of sALP (40 mg/ml), each vial contains 0.45 ml solution and 18 mg of sALP (40 mg/ml), each vial contains 0.7 ml solution and 28 mg of sALP (40 mg/ml), or each vial contains 1.0 ml solution and 40 mg of asfotase alfa (40 mg/ml)). A sALP (such as TNALP, for example the sALP polypeptide of SEQ ID NO: 1 or a polypeptide variant having at least 95% sequence identity to the sequence of SEQ ID NO: 1, e.g., asfotase alfa) can be formulated as a solution for injection at a concentration of 100 mg/ml, in which each 1 ml of solution contains 100 mg of sALP or sALP polypeptide (e.g., each vial contains 0.8 ml solution and 80 mg of asfotase alfa (100 mg/ml)).

For example, the recommended dosage of a sALP (such as TNALP, for example the sALP polypeptide of SEQ ID NO: 1 or a polypeptide variant having at least 95% sequence identity to the sequence of SEQ ID NO: 1, e.g., asfotase alfa) is 2 mg/kg of body weight administered subcutaneously three times per week, or a dosage regimen of 1 mg/kg of body weight administered subcutaneously six times per week. Additional dosage information is provided below (Table 1).

TABLE 1

DOSING OF ASFOTASE ALFA

| | If injecting 3x per week | | | If injecting 6 x per week | | |
|---|---|---|---|---|---|---|
| Body Weight (kg) | Dose to be injected | Volume to be injected | Vial type used for injection | Dose to be injected | Volume to be injected | Vial type used for injection |
| 3 | 6 mg | 0.15 ml | 0.3 ml | | | |
| 4 | 8 mg | 0.20 ml | 0.3 ml | | | |
| 5 | 10 mg | 0.25 ml | 0.3 ml | | | |
| 6 | 12 mg | 0.30 ml | 0.3 ml | 6 mg | 0.15 ml | 0.3 ml |
| 7 | 14 mg | 0.35 ml | 0.45 ml | 7 mg | 0.18 ml | 0.3 ml |
| 8 | 16 mg | 0.40 ml | 0.45 ml | 8 mg | 0.20 ml | 0.3 ml |
| 9 | 18 mg | 0.45 ml | 0.45 ml | 9 mg | 0.23 ml | 0.3 ml |
| 10 | 20 mg | 0.50 ml | 0.7 ml | 10 mg | 0.25 ml | 0.3 ml |
| 11 | 22 mg | 0.55 ml | 0.7 ml | 11 mg | 0.28 ml | 0.3 ml |
| 12 | 24 mg | 0.60 ml | 0.7 ml | 12 mg | 0.33 ml | 0.3 ml |
| 13 | 26 mg | 0.65 ml | 0.7 ml | 13 mg | 0.35 ml | 0.45 ml |
| 14 | 28 mg | 0.70 ml | 0.7 ml | 14 mg | 0.35 ml | 0.45 ml |
| 15 | 30 mg | 0.75 ml | 1 ml | 15 mg | 0.38 ml | 0.45 ml |
| 16 | 32 mg | 0.80 ml | 1 ml | 16 mg | 0.40 ml | 0.45 ml |
| 17 | 34 mg | 0.85 ml | 1 ml | 17 mg | 0.43 ml | 0.45 ml |
| 18 | 36 mg | 0.90 ml | 1 ml | 18 mg | 0.45 ml | 0.45 ml |
| 19 | 38 mg | 0.95 ml | 1 ml | 19 mg | 0.48 ml | 0.7 ml |
| 20 | 40 mg | 1.00 ml | 1 ml | 20 mg | 0.50 ml | 0.7 ml |
| 25 | 50 mg | 0.50 ml | 0.8 ml | 25 mg | 0.63 ml | 0.7 ml |
| 30 | 60 mg | 0.60 ml | 0.8 ml | 30 mg | 0.75 ml | 1 ml |
| 35 | 70 mg | 0.70 ml | 0.8 ml | 35 mg | 0.88 ml | 1 ml |
| 40 | 80 mg | 0.80 ml | 0.8 ml | 40 mg | 1.00 ml | 1 ml |
| 50 | | | | 50 mg | 0.50 ml | 0.8 ml |
| 60 | | | | 60 mg | 0.60 ml | 0.8 ml |
| 70 | | | | 70 mg | 0.70 ml | 0.8 ml |
| 80 | | | | 80 mg | 0.80 ml | 0.8 ml |
| 90 | | | | 90 mg | 0.90 ml | 0.8 ml (×2) |
| 100 | | | | 100 mg | 1.00 ml | 0.8 ml (×2) |

In some instances, administration of the sALP (such as TNALP, for example the sALP polypeptide of SEQ ID NO: 1 or a polypeptide variant having at least 95% sequence identity to the sequence of SEQ ID NO: 1, e.g., asfotase alfa) according to the disclosure can result in one or more of the following: (i) an increase in bone healing in the patient; and/or (ii) a change in bone mineral density that is undetectable or increased.

In any of the aspects disclosed herein, the patient exhibits tolerability to administration of the sALP (such as TNALP, for example the sALP polypeptide of SEQ ID NO: 1 or a polypeptide variant having at least 95% sequence identity to the sequence of SEQ ID NO: 1, e.g., asfotase alfa), such as a lack of or decreased incidence of adverse events selected from the group consisting of injection site erythema, decrease in hemoglobin, pyrexia, pneumonia, upper respiratory tract infection, otitis media, vomiting, constipation, diarrhea, tooth loss, nasopharyngitis, rash, dental caries, and irritability.

In any of the aspects disclosed herein, the sALP (such as TNALP, for example the sALP polypeptide of SEQ ID NO: 1 or a polypeptide variant having at least 95% sequence identity to the sequence of SEQ ID NO: 1, e.g., asfotase alfa) is formulated in a pharmaceutical composition, with at least one pharmaceutically acceptable carrier, such as saline (e.g., sodium chloride and sodium phosphate). For example, the at least one pharmaceutically acceptable carrier can include 150 mM sodium chloride and 25 mM sodium phosphate.

In any of the above aspects, the sALP (such as TNALP, for example the sALP polypeptide of SEQ ID NO: 1 or a polypeptide variant having at least 95% sequence identity to the sequence of SEQ ID NO: 1, e.g., asfotase alfa) is physiologically active toward PEA, PPi, and PLP, catalytically competent to improve skeletal mineralization in bone, and/or is the soluble extracellular domain of an alkaline phosphatase.

Formulations

The pharmaceutical compositions including sALPs (such as TNALP, for example the sALP polypeptide of SEQ ID NO: 1 or a polypeptide variant having at least 95% sequence identity to the sequence of SEQ ID NO: 1, e.g., asfotase alfa) can be formulated according to standard methods. Pharmaceutical formulation is a well-established art, and is further described in, e.g., Gennaro (2000) *Remington: The Science and Practice of Pharmacy,* 20th Edition, Lippincott, Williams & Wilkins (ISBN: 0683306472); Ansel et al. (1999) *Pharmaceutical Dosage Forms and Drug Delivery Systems,* 7th Edition, Lippincott Williams & Wilkins Publishers (ISBN: 0683305727); and Kibbe (2000) *Handbook of Pharmaceutical Excipients,* American Pharmaceutical Association, 3rd Edition (ISBN: 091733096X). For instance, a sALP composition (such as TNALP, for example the sALP polypeptide of SEQ ID NO: 1 or a polypeptide variant having at least 95% sequence identity to the sequence of SEQ ID NO: 1, e.g., asfotase alfa) can be formulated, for example, as a buffered solution at a suitable concentration and suitable for storage at 2-8° C. (e.g., 4° C.). A composition can also be formulated for storage at a temperature below 0° C. (e.g., −20° C. or −80° C.). A composition can further be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, the compositions described herein can be stable in storage for at least 1 year at 2-8° C. (e.g., 4° C.).

The pharmaceutical compositions including sALPs (such as TNALP, for example the sALP polypeptide of SEQ ID NO: 1 or a polypeptide variant having at least 95% sequence identity to the sequence of SEQ ID NO: 1, e.g., asfotase alfa) can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application.

For example, compositions intended for systemic or local delivery can be in the form of injectable or infusible solutions. Accordingly, the compositions including sALPs (such as TNALP, for example the sALP polypeptide of SEQ ID NO: 1 or a polypeptide variant having at least 95% sequence identity to the sequence of SEQ ID NO: 1, e.g., asfotase alfa) can be formulated for administration by a parenteral mode (e.g., subcutaneous, intravenous, intraperitoneal, or intramuscular injection).

The pharmaceutical compositions including sALPs (such as TNALP, for example the sALP fusion polypeptide of SEQ ID NO: 1 or a polypeptide variant having at least 95% sequence identity to the sequence of SEQ ID NO: 1, e.g., asfotase alfa) can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see herein) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The pharmaceutical compositions described herein can also be formulated in immunoliposome compositions. Such formulations can be prepared by methods known in the art such as, e.g., the methods described in Epstein et al. (1985) *Proc Natl Acad Sci USA* 82:3688; Hwang et al. (1980) *Proc Natl Acad Sci USA* 77:4030; and U.S. Pat. Nos. 4,485,045 and 4,544,545. Liposomes with enhanced circulation time are disclosed in, e.g., U.S. Pat. No. 5,013,556.

Pharmaceutical compositions including sALPs (such as TNALP, for example the sALP polypeptide of SEQ ID NO: 1 or a polypeptide variant having at least 95% sequence identity to the sequence of SEQ ID NO: 1, e.g., asfotase alfa) can also be formulated with a carrier that will protect the composition (e.g., a sALP polypeptide or sALP fusion polypeptide) against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) *Sustained and Controlled Release Drug Delivery Systems*, Marcel Dekker, Inc., New York.

When compositions are to be used in combination with a second active agent, the compositions can be co-formulated with the second agent, or the compositions can be formulated separately from the second agent formulation. For example, the respective pharmaceutical compositions can be mixed, e.g., just prior to administration, and administered together or can be administered separately, e.g., at the same or different times.

Carriers/Vehicles

Preparations containing a sALP (such as TNALP, for example the sALP polypeptide of SEQ ID NO: 1 or a polypeptide variant having at least 95% sequence identity to the sequence of SEQ ID NO: 1, e.g., asfotase alfa) can be provided to a patient, such as a patient having at least one symptom of neurofibromatosis type 1, at least one symptom of dystrophic scoliosis, or in need of bone healing, in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. For example, the pharmaceutically acceptable carrier can include sodium chloride and/or sodium phosphate, in which the composition includes, e.g., about 150 mM sodium chloride and/or about 25 mM sodium phosphate, pH 7.4.

Intravenous vehicles can include fluid and nutrient replenishers, electrolyte replenishers, such as those based upon Ringer's dextrose, and the like. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, can be present in such vehicles. A thorough discussion of pharmaceutically acceptable carriers is available in *Remington's Pharmaceutical Sciences* (Mack Pub. Co., N.J. 1991).

EXAMPLES

The following example is intended to illustrate, rather than limit, the disclosure. It is to be understood that the particular examples, materials, amounts, and procedures are to be interpreted broadly in accordance with the scope and spirit of the disclosure as set forth herein.

Example 1. The Use of Asfotase Alfa to Promote Mineralization after Spinal Fusion for Dystrophic Scoliosis in a Patient with Neurofibromatosis Type 1 (NF1)

Dystrophic scoliosis is a rare, but serious, skeletal manifestation in patients with neurofibromatosis type 1 (NF1) and may be associated with debilitating neurological impairment. Dystrophic curves progress rapidly and require early fusion, which is often complicated by poor bone healing and pseudoarthrosis. Poor bone healing in NF1 is thought to be due to a combination of reduced bone healing, increased bone resorption, and poor bone mineralization. Loss of neurofibromin can upregulate genes that promote pyrophosphate (PPi) synthesis, leading to PPi accumulation and inhibition of mineralization, impaired osteoblast differentiation with reduced alkaline phosphatase expression, and increased bone resorption.

Pre-clinical studies in mouse knock-out models of NF1 showed a decrease in the expression of Enpp1 and Ank, two main genes controlling PPi homeostasis. This result, however, was inconsistent with a reported human cell assay in adherent bone marrow cells (De la Croix Ndong, J., et al., *Nature Medicine*; 20: 904-910, 2014).

Figure 2:
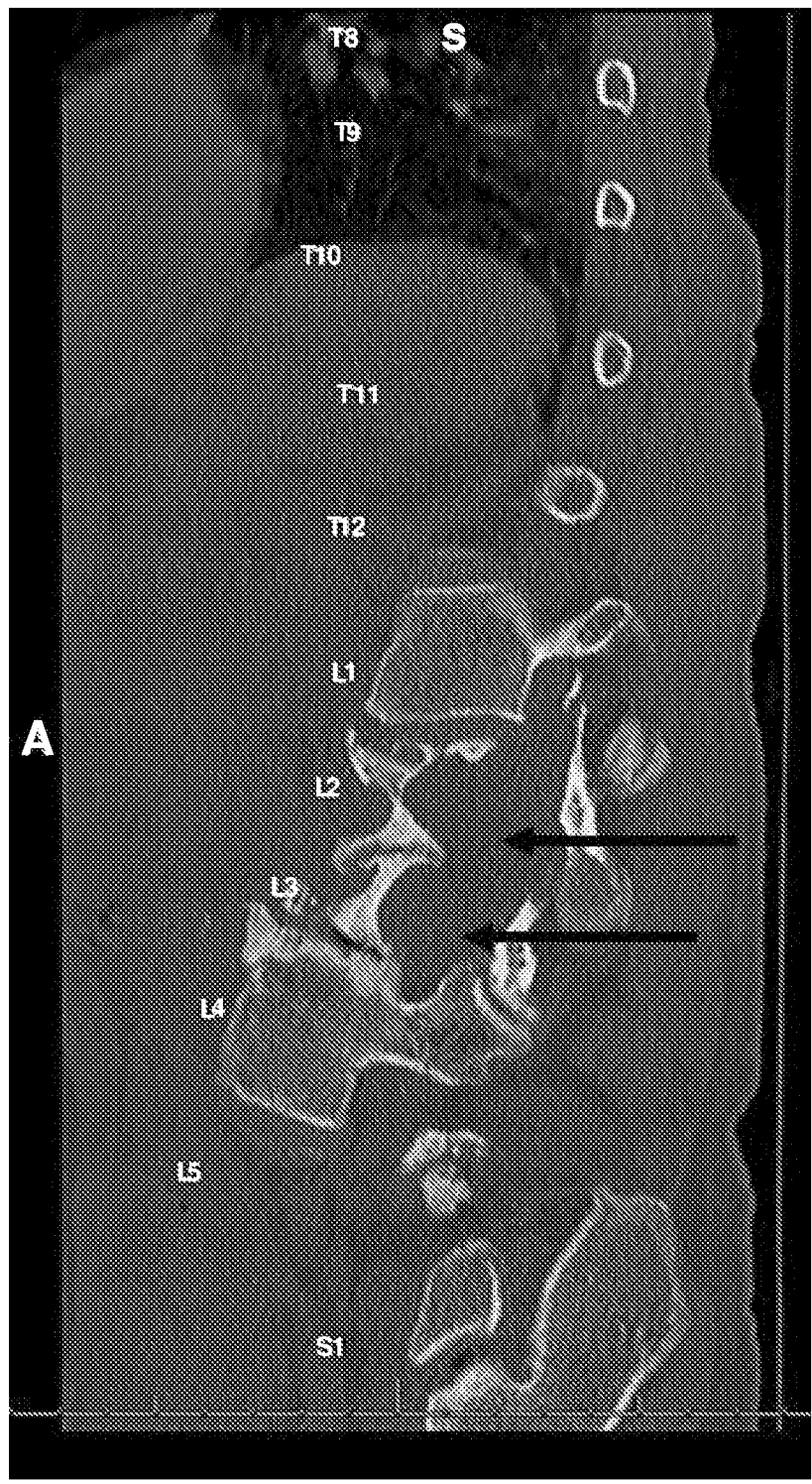
FIG. 2 is a computed tomography (CT) scan of the lumbar spine of the same 47 year old patient identified in FIG. 1. The CT scan shows severe dural ectasia throughout the lumbar but most pronounced at L2 and L3, denoted by arrows, where there is prominent posterior vertebral body scalloping.

In this study, a 54-year-old post-menopausal woman with severe NF1-related dystrophic scoliosis and osteoporosis underwent three prior back surgeries over a period of 7 years, including prior T11 to pelvis spinal fusion (FIG. 1). The spinal fusion was complicated by advanced dural ectasia (FIG. 2), pseudoarthrosis, and life-threatening hemorrhage. An anterior approach was attempted, but was aborted due to left iliac vein complications. The patient also received posterior instrumentation and augmentation revision with bone morphogenetic proteins (BMPs), but continued to have progressive loosening of the screws, paresthesia of anterior thighs, and intractable back pain. She developed displacement of the rod at the L4 pedicle, requiring repeat surgery. The patient was also was taking 5 mg of morphine to help with the intractable back pain. The patient was managed conservatively with morphine treatment; however, back pain persisted with visual analog scale (VAS) pain score of 9 and Oswestry low back disability score of 52%. A CT scan revealed advanced peripheral lucency of the left posterior iliac screw, indicative of loosening (FIG. 3A) and a fracture of the left vertical rod at the L4 pedicle screw connection (FIG. 3B), necessitating a fourth spinal surgery.

Given a high probability of implant failure and difficulty in achieving solid arthrodesis after surgery, a decision was made to combine surgical intervention with additional available medical interventions including bone morphogenetic proteins (recombinant human BMP-2) to enhance bone healing, bisphosphonates (e.g., zoledronic acid) to inhibit bone resorption, and asfotase alfa (recombinant human alkaline phosphatase) to improve bone mineralization to achieve solid arthrodesis.

Figure 4:
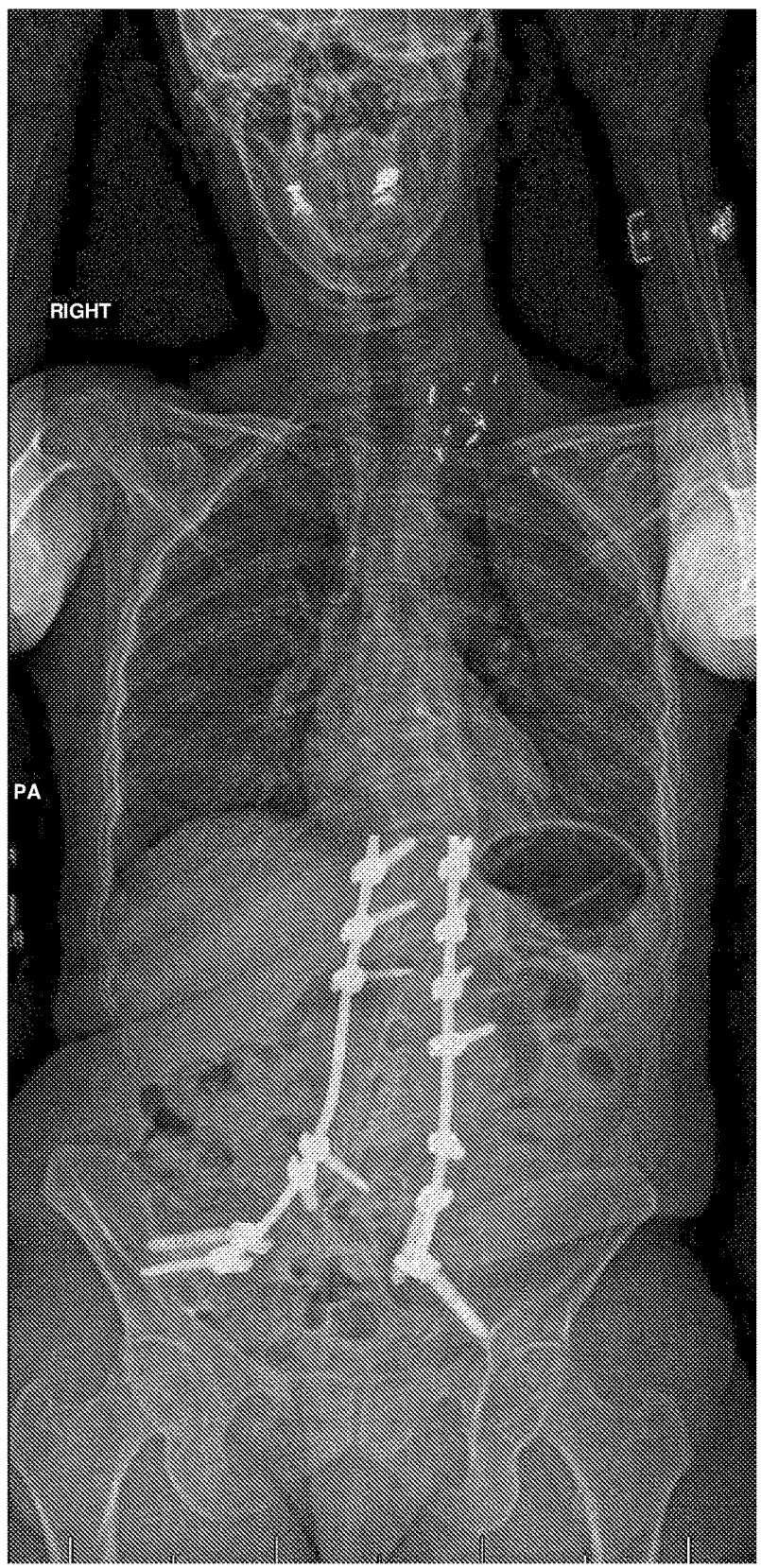
FIG. 4 is a radiograph of a postoperative plain film showing spinal fusion instrumentation from T11 to sacrum with bilateral iliac screws and markedly improved dystrophic scoliosis deformity.

At the start of the study, the patient underwent a revision of lumbar fusion including reinsertion of spinal instrumentation of thoracic spine T11 to sacrum, reinsertion of pelvic fixation and posterior spinal fusion from T11 to pelvis (FIG. 4). This was her fourth spinal surgery. Medical intervention during and after the repeat surgery included intrasurgical BMPs applied directly to the bone being operated on in order to enhance bone healing.

Approximately 3 months after surgery, to inhibit bone resorption, the patient received bisphosphonate therapy as a single 5 mg intravenous infusion of zoledronic acid without side effects.

Approximately 7 months after surgery and continuing for a 6 month period, asfotase alfa (recombinant human alkaline phosphatase, STRENSIQ®, Alexion Pharmaceuticals, Inc.) was administered subcutaneously at a dose of 2 mg/kg 3×/week to improve bone mineralization. Administration of asfotase alfa was discontinued at the end of six months (i.e., 13 months post-surgery). The patient did not experience serious adverse events during the treatment.

Solid arthrodesis was successfully obtained 13 months after this fourth surgery. Stable instrumented spinal fusion, as determined by CT scan (spinal radiograph) was observed at 13 months. No substantial change in overall bone mineral density was seen at that time, with T10 vertebral body as a reference point, using Hounsfield unit scale measurement.

BMPs alone (used to enhance bone formation) did not result in successful spinal fusion in this patient during earlier surgeries. They were used again during the patient surgery, but this time alongside combination therapy with a bisphosphonate and asfotase alfa. It was found that asfotase alfa in combination with BMPs (e.g., rhBMP-2) and bisphosphonate resulted in solid arthrodesis after spinal surgery in a patient with NF1-related dystrophic scoliosis, where BMP therapy alone had previously failed.

It was noted that markers of bone resorption increased after surgery. Following administration of the bisphosphonate zolendronic acid (ZOL) three months after surgery, bone resorption markers (NTX and CTX) decreased, but so also did bone formation markers (OCN and P1NP). Without being bound by theory, a decrease in these markers may be due to reduced bone turnover after ZOL. Consequently, the patient may experience inhibition of bone mineralization due to both the underlying disease and the use of ZOL (which otherwise has the beneficial effect of inhibiting bone resorption).

Meanwhile, however, both bone-specific alkaline phosphatase (BSAP) and total ALP levels increased significantly after administration of asfotase alfa. The study results suggest that administration of asfotase alfa following administration of a bisphosphonate such as ZOL can improve bone mineralization, somewhat like a "rescue" therapy. Administration of asfotase alfa was shown to improve bone mineralization despite the potentially confounding effects of administration of ZOL: fracture healing occurred, and loosening of the screws showed signs of resolution. These results suggest a more general treatment protocol that employs asfotase alfa as an adjunct to bisphosphonate therapy. More particularly, administration of bisphosphonates such as ZOL to inhibit bone resorption can be followed by administration of asfotase alfa to counteract possible adverse effects on bone mineralization of the bisphosphonate. This is in contrast to prevailing standard of care, which suggests that bisphosphonate treatment is contraindicated during asfotase alfa treatment (Kishnani, P., et al., *Mol. Gen. Metab.* 122: 4-17, 2017).

Study Details

Table 2 summarizes laboratory and radiological investigations performed during the study's period, including reference ranges. The timing of all procedures was approximate, with specific date flexibility allowed based on the clinical progress of the patient, and to accommodate patient's schedule.

TABLE 2

Laboratory and Radiological Investigations during Study Period

| | Baseline (before surgery as noted) | | ~5 days after surgery | 3 mo. after surgery | 4-7 mo. after surgery | | 8 mo. after surgery 1 month after starting asfotase alfa | 1.2 yr after surgery 6 months after starting asfotase alfa |
|---|---|---|---|---|---|---|---|---|
| Creatinine (0.52-1.04 mg/dl) | 0.63 | Surgery | 0.38 | 0.58 | | Asfotase alfa started 7 months after surgery | 0.63 | 0.68 |
| 25-0H Vitamin D (20-75 ug/L) | 67 | | | 94 | | | 43 | 42 |
| Total calcium (8.5-10.1 mg/dl) | 8.5 | | 8.4 | 9.0 | | | 8.8 | 8.7 |
| Parathyroid hormone (12-72 pg/ml) | 37 | | | 73 | | | 65 | 66 |
| Alkaline phosphatase (40-150 U/L) | 58 | | 86 | | | | >2330 | >2330 |
| Bone specific alkaline phosphatase (postmenopausal woman: 7-22.4 ug/L) | 12.3 | | | 19.1 | | | 1949.5 | 1751.1 |
| Osteocalcin (11-50 ng/ml) | 26 | | 20 | 31 | | | 10 | 17 |
| Procollagen type 1 intact N terminal Pro (P1NP) (postmenopausal woman: 16-96 ug/L) | 83 | | 87 | 120 | | | 43 | 54 |
| C-Telopeptide (CTx) (postmenopausal woman: 104-1008 pg/ml) | 721 | | 844 | 1256 | | | | 559 |
| N-Telopeptide (NTx) (postmenopausal woman: 6.2-19 nM BCE) | 15.6 | | 17.9 | 25.5 | | | 10.6 | 14.4 |
| Serum inorganic pyrophosphate (PPi) (1.00-5.82 μM) | 1.11 | | | | | | 2.3 | |
| Serum pyridoxal 5'-phosphate (PLP; vitamin B6) (2.81-26.7 ng/ml) | 4.32 | | | | | | 4.7 | |
| Vitamin B6 (20.0- 125.0 nmol/L) using quantitative HPLC http://ltd.aruplab.com/Tests/Pub/0080111 | 17.9 | | | | | | 2.7 | <2 |
| DXA scan | 3 mo prior | | | | | | | x |
| Spine x-ray | 7 mo prior | | x | x | x | | | x |
| Spine CT | 7 mo prior | | x | | | | | x |
| Orthopedic visit with neurological exam | 2 mo prior | | | x | x | | | x |
| Endocrine visit | 2 mo prior | | | x | x | | x | x |
| Zoledronic acid | | | | x | | | | |
| Eye examination | | | | | x | | | x |
| Renal ultrasound | | | | | x | | | x |

Pre-Asfotase Alfa Treatment Investigations
Report of a Renal Ultrasound Four Months after Surgery Right kidney 9.7 cm, normal echotexture and cortex. No mass, stones or hydronephrosis Left kidney 10.4 cm, normal echotexture and cortex. No mass, stones or hydronephrosis Comprehensive eye exam on 5 months after surgery reported as keratoconjunctivitis sicca especially left eye as seen by eyelid anomaly temporally. Normal oculomotor nerve. Normal macula.

Baseline DXA scan revealed the left femoral neck BMD 0.643 which corresponded to T-score of −2.8. The right femoral neck BMD was 0.627 which corresponded to T-score of −3.0. Mean total hip BMD 0.635 which corresponded to T-score of −2.9. Compared to BMD in 8 years earlier, bone density decreased 8.1% which was significant. Left 33% forearm BMD 0.621 which corresponded to T-score of −3.0.

Radiographic Data, CT Lumbar Spine

Figure 3A:
FIGS. 3A-3B are CT scans performed 6 months before the fourth spinal surgery of the 47 year old patient.
Figure 3B:
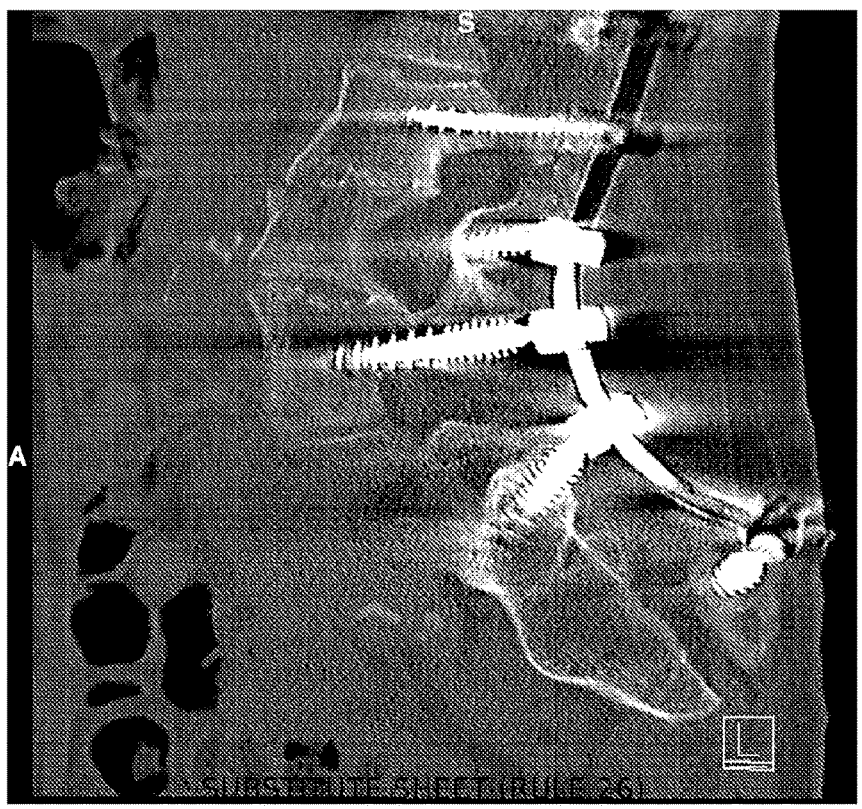

Preoperative CT and spinal radiograph obtained 7 months prior to surgery showed fracture of the left vertical connecting rod below left L4 pedicle screw and peripheral lucency of the left posterior iliac spine screw (FIGS. 3A-3B). Advanced dural ectasia of lumbar spine, particularly the right L2-L4, and postsurgical change of the spine pelvis fusion instrumentation from T 11 to pelvis with bilateral sacroiliac joints screws were noted.

The date of the surgery, a revision of lumbar fusion including reinsertion of spinal instrumentation of thoracic spine T11 to sacrum, reinsertion of pelvic fixation and posterior spinal fusion from T11 to pelvis were performed (FIG. 4).

Figure 5A:
FIGS. 5A-5B are postoperative CT scans performed 2 days after spinal surgery.
Figure 5B:
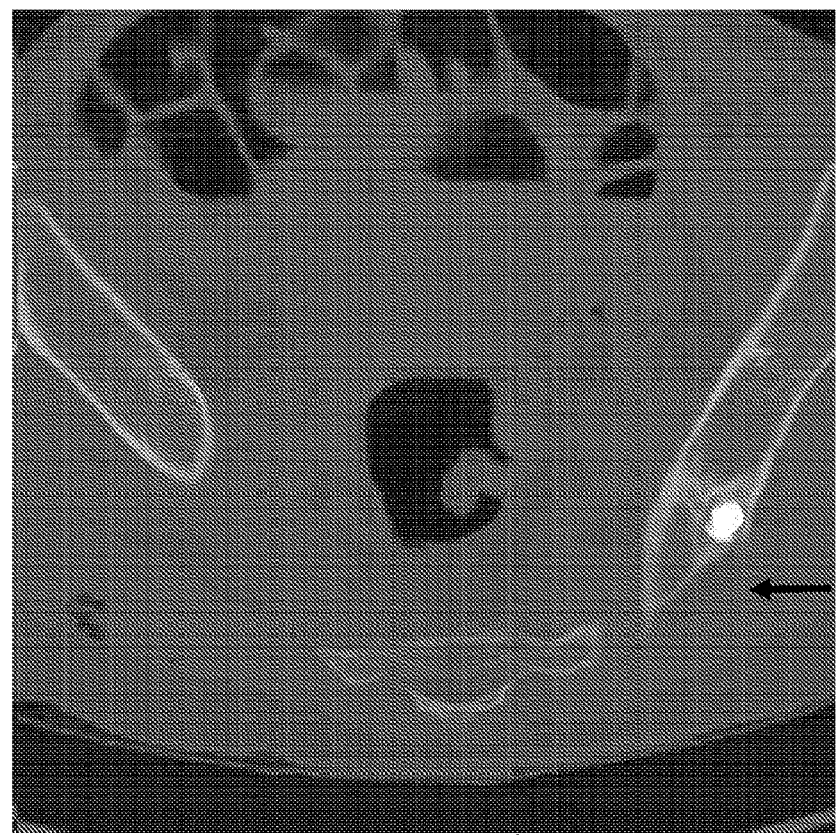

Immediate postoperative CT and spinal radiograph obtained 2 days after surgery due to sudden onset of stocking-like paresthesia of bilateral ankles without weakness showed post-surgical changes of revision instrumented spinal fusion T11-pelvis with additional screws extending into the medial iliac bones bilaterally. Bilateral pedicle screws at T11, T12, L1, S1, left pedicle screw at L2 and L4, right pedicle screw at L5, and bilateral iliac screws were noted. Stable lucency around the left posterior iliac screw was seen with a new bony defect in the outer cortex at the tip of the screw (FIGS. 5A-5B). Paresthesia of bilateral ankles improved gradually 2 days later, and the patient ambulated safely prior to discharge home. Given patient's severe dystrophic scoliosis and previous high probability of failing given past surgical history of mechanical failing, the patient also received zoledronic acid to inhibit bone resorption (5 mg IV at 3 months after surgery one time) to inhibit bone resorption and asfotase alfa to improve bone mineralization (2 mg/kg 3×/week subcutaneous injection) from 7 to 13 months after surgery) to improve bone mineralization.

Spinal radiograph obtained 3 month and 7 months after surgery showed stable postsurgical changes of spinal fusion, with intact instrumentation noted posteriorly from T11 through the sacrum, with screws extending across both sacroiliac joints, i.e., stable instrumented spinal fusion T11-pelvis with solid bilateral dorsolateral ankyloses were observed. Healing and sclerosis of the previously seen bony defect associated with the tip of the left posterior iliac screw was observed since the two days after surgery observation.

Post Asfotase Alfa Treatment Investigations
Radiograph

CT and spinal radiograph obtained approximately 7 months after asfotase alfa initiation showed stable instrumented spinal fusion T11-pelvis with solid bilateral dorsolateral ankylosis. Interval healing of left peri-screw iliac fracture was observed since 5 days after surgery. Minimal marginal lucency about the bilateral sacroiliac joint screws was observed without convincing evidence of loosening. Stable convex right scoliosis and asymmetric right dural ectasia were observed.

A repeat renal ultrasound, repeat eye exam, and repeat DXA scan were planned for 1.2 years after surgery. Renal ultrasound and comprehensive eye examination before and after asfotase alfa treatment revealed no ectopic calcification. On the follow-up visit at 13 months after surgery, patient reported an improvement in back pain with a VAS pain score of 7 and an Oswestry low back disability score of 42%. The patient was able to stop morphine treatment.

Additional Observations

Figure 6:
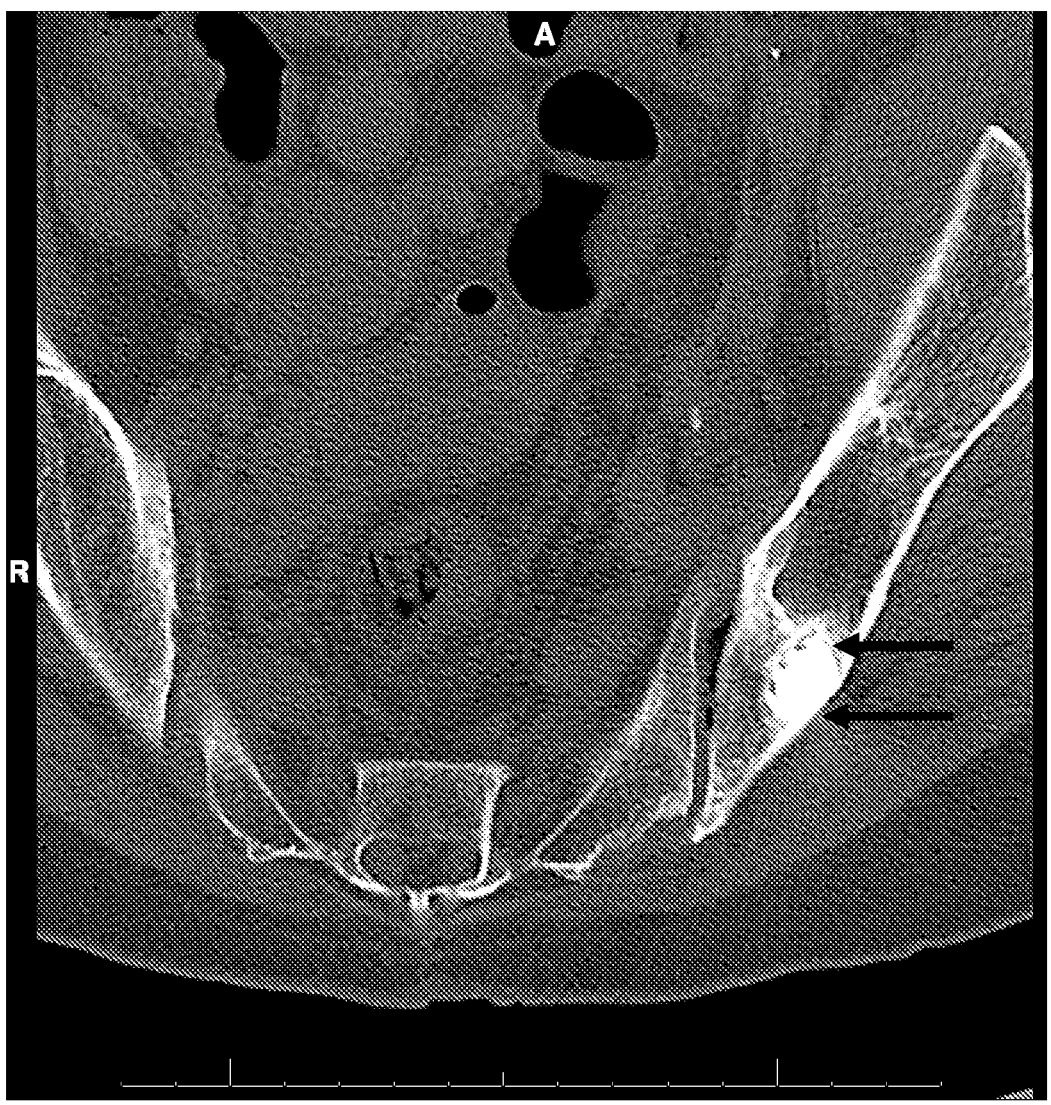
FIG. 6 is a CT scan performed 13 months after spinal surgery and following 6 months of treatment with asfotase alfa. The CT scan shows marginal lucency around the screw without evidence of loosening (upper arrow) and healed fracture at the tip of the left posterior iliac screw (lower arrow).

In conclusion, stable instrumented spinal fusion was observed after surgery determined by spinal radiograph. In comparison to immediate postoperative CT lumbar spine (obtained 2 days after surgery) that showed lucency around the left posterior iliac screw (suggestive of screw loosening) with a new bony defect at the tip of the screw (indicative of peri-screw fracture), a CT lumbar spine approximately 6 months after asfotase alfa initiation showed healed fracture at the tip of the left posterior iliac screw without evidence of loosening (FIG. 6). However, when compared between these 2 CT scans, there was no significant change in bone mineral density using CT Hounsfield measurement noted in T10 vertebral body as reference point where there was no surgical change. Degree of gross bony bridging (indicating bone formation) that was presented before the revisional surgery as well as objective measurement (HU measurement) at posterior element bony bridging sites showed no substantial interval change.

Example 2. Treatment of a Femoral Fracture

According to the methods disclosed herein, an orthopedic surgeon of skill in the art may treat a patient with a fractured femur. For example, the patient may have fractured her femur after falling off a bicycle or may have spontaneous fracture. The non-displaced fracture may cause intense pain and the doctor may perform an orthopedic surgery in which a plate and four screws are to be placed over the fracture, to be followed by immobilization of the patient's leg in a cast for three months. Following the three months, if the bone does not display adequate healing as viewed by X-ray and CT scan, or if the screws loosen, the orthopedic surgeon may treat the patient with a regimen of asfotase alfa administered subcutaneously at 6 mg/kg/week for two months. Following the asfotase alfa treatment, the doctor or surgeon may perform an additional X-ray and CT scan to visualize the healing process. The doctor or surgeon may determine that the asfotase alfa treatment has aided the healing process and the two screws are no longer loose. After sufficient healing, the surgeon may determine that the hardware, including the plate and four screws, may be removed from the femur.

Example 3. Treatment of Traumatic Facial Fracture

A patient with a multiply fractured facial cheek bone could be treated by an oral maxillofacial surgeon or plastic surgeon with reconstruction of the facial bones to restore the original shape and features of the face. Due to the complexity of the fractures, the surgeon may decide to utilize multiple screws and plates to aid in reformulation of the facial bones. The screws and plates may be designed to remain in the face permanently. The doctor may first initiate a regimen of asfotase alfa administered locally at 2 mg/kg/week for two weeks before surgery. The doctor may perform the surgery and place the plates and screws onto the fractured areas of the cheek bone. Following three months of recovery time, the doctor may visualize the healing process by X-ray and CT scan. The doctor may determine that one of the screws is loose, and the dosage of asfotase alfa could be increased to 6 mg/kg/week. Following another month of recovery time, the doctor may again visualize the healing process by X-ray and CT scan and may determine that the screw is no longer loose, at which time the asfotase alfa treatment may be terminated.

REFERENCES

1) Durrani, A. A., et al., 2000. Modulation of spinal deformities in patients with neurofibromatosis type 1. *Spine* 25, 69-75.
2) Wu, X., et al., 2006. Neurofibromin plays a critical role in modulating osteoblast differentiation of mesenchymal stem/progenitor cells. *Human Molecular Genetics* 15, 2837-2845.
3) Yang, F. C., et al., 2006. Hyperactivation of p21ras and PI3K cooperate to alter murine and human neurofibromatosis type 1-haploinsufficient osteoclast functions. *J. Clinical Investigation* 116, 2880-2891.
4) Petryk, A., Bechtold, J., Carlson, C., Dahl, M., Polly, D., 2016. Rationale for the use of bisphosphonates after surgery for dystrophic scoliosis in NF1 patients. *Annual Meeting of the Orthopaedic Research Society, Poster No.* 2245
5) Whyte, M. P., et al., 2012. Enzyme-replacement therapy in life-threatening hypophosphatasia. *NEJM* 366, 904-913.
6) de la Croix Ndong, J., et al., 2014. Asfotase alfa improves bone growth, mineralization and strength in mouse models of neurofibromatosis type-1. *Nature Medicine* 20, 904-910.
7) US 2013/0323244 A1, Compositions Comprising Alkaline Phosphatase and/or Natriuretic Peptide and Methods of Use Thereof
8) WO 2017/173395, Methods for Treating Hypophosphatasia in Adolescents and Adults
9) European Patent No.: 2368999, Bone Targeted Alkaline Phosphatase, Kits, and Methods of Use Thereof
10) Delucia, T. A., Yohay, K., Widmann, R. F., 2011. Orthopaedic aspects of neurofibromatosis: update. *Current opinion in pediatrics* 23, 46-52
11) Yu et al., 2005, Neurofibromin and its inactivation of Ras are prerequisites for osteoblast functioning. *Bone* 36, 793-802
12) Heerva et al., 2012, Osteoclasts derived from patients with neurofibromatosis 1 (NF1) display insensitivity to bisphosphonates in vitro. *Bone* 50, 798-803
13) Schindeler et al., 2008, Modeling bone morphogenetic protein and bisphosphonate combination therapy in wild-type and Nf1 haploinsufficient mice. *Journal of orthopaedic research*: official publication of the Orthopaedic Research Society 26, 65-74
14) Birke et al., 2010, Preliminary experience with the combined use of recombinant bone morphogenetic protein and bisphosphonates in the treatment of congenital pseudarthrosis of the tibia. *Journal of children's orthopaedics* 4, 507-517
15) Bobyn et al., 2014, Maximizing bone formation in posterior spine fusion using rhBMP-2 and zoledronic acid in wild type and NF deficient mice. *Journal of orthopaedic research*: official publication of the Orthopaedic Research Society 32, 1090-1094
16) Seitz et al., 2010, High bone turnover and accumulation of osteoid in patients with neurofibromatosis 1. *Osteoporosis international*: a journal established as result of cooperation between the European Foundation for Osteoporosis and the National Osteoporosis Foundation of the USA 21, 119-127

The foregoing detailed description and examples have been given for clarity of understanding only. No unnecessary limitations are to be understood therefrom. The disclosure is not limited to the exact details shown and described, for variations apparent to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The complete disclosures of all patents, patent applications including provisional patent applications, publications including patent publications and nonpatent publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference.

The invention claimed is:

1. A method of improving bone formation at a site of orthopedic hardware implantation in a subject with neurofibromatosis type 1 (NF1) or dystrophic scoliosis comprising:

administering a soluble alkaline phosphatase (sALP) to the subject before, during, and/or after at least one orthopedic surgery comprising implantation of the hardware, wherein the sALP is administered to the subject at a dosage providing from about 0.2 mg/kg/week to about 12 mg/kg/week, wherein administration of the sALP results in an increase in bone healing at the site of implantation of the hardware that results in new bone formation in the subject relative to an untreated subject.

2. The method of claim 1, wherein the increase in bone healing is between two bones joined by arthrodesis.

3. The method of claim 1, wherein the increase in bone healing is between two portions of a bone that have been separated by a fracture.

4. The method of claim 1, wherein the increase in bone healing is in bone in contact with the hardware or is an increase in opacity in bone.

5. The method of claim 1, wherein the hardware is a screw, rod, plate, metal cage, nail, pin, or nut.

6. The method of claim 1, wherein the orthopedic surgery comprises:

(a) one or more of arthrodesis, removal of bone, insertion of bone graft material, and insertion of the hardware; or (b) one or more of an open surgery or a minimally invasive surgery.

7. The method of claim 1, further comprising administering to the subject bone morphogenetic proteins (BMP) and/or bisphosphonates.

8. The method of claim 7, wherein the BMP is administered during the orthopedic surgery or the bisphosphonate is administered after the orthopedic surgery.

9. The method of claim 8, wherein the bisphosphonate is administered about three months after the orthopedic surgery.

10. The method of claim 1, wherein:
(a) the sALP is administered about seven months after the orthopedic surgery;
(b) the sALP is formulated for daily or weekly administration;
(c) the sALP is formulated for administration twice a week, three times a week, four times a week, five times a week, six times a week, or seven times a week;
(d) the sALP is formulated at a dosage of 2 mg/kg for administration three times a week, at a dosage of 3 mg/kg for administration three times a week, or at a dosage of 1 mg/kg for administration six times a week;
(e) the sALP is formulated for administration once daily;
(f) the sALP is formulated for administration on consecutive or alternating days;
(g) the sALP is administered for a treatment period of at least one month, at least two months, at least three months, at least four months, at least five months, at least six months, at least seven months, at least eight months, at least nine months, at least ten months, or longer; or
(h) the sALP is formulated in a pharmaceutical composition with at least one pharmaceutically acceptable carrier.

11. The method of claim 10, wherein the at least one pharmaceutically acceptable carrier is saline or comprises sodium chloride and sodium phosphate.

12. The method of claim 11, wherein the at least one pharmaceutically acceptable carrier comprises about 150 mM sodium chloride and about 25 mM sodium phosphate.

13. The method of claim 10, wherein the pharmaceutical composition is formulated for at least one of subcutaneous, intramuscular, intravenous, oral, nasal, sublingual, intrathecal, and intradermal administration.

14. The method of claim 1, wherein:
(a) the sALP is the soluble extracellular domain of an alkaline phosphatase;
(b) the sALP is administered at a dosage from about 6 mg/kg/week to about 9 mg/kg/week; or
(c) the sALP comprises an amino acid sequence having at least 80%, 85%, 90%, 95%, 97%, 99%, or 100% sequence identity to the sequence of SEQ ID NO: 1.

15. The method of claim 14, wherein the sALP comprises an amino acid sequence having 100% sequence identity to the sequence of SEQ ID NO: 1.

16. The method of claim 1, wherein the at least one orthopedic surgery is selected from the group consisting of arthroscopy of the knee, shoulder, hip, ankle, elbow, or wrist, fracture and meniscectomy, shoulder arthroscopy and decompression, carpal tunnel release, knee arthroscopy and chondroplasty, removal of support implant, knee arthroscopy and anterior cruciate ligament reconstruction, knee replacement, repair of femoral neck fracture, repair of trochanteric fracture, debridement of skin/muscle/bone/fracture, knee arthroscopy repair of one or both menisci, hip replacement, shoulder arthroscopy/distal clavicle excision, repair of rotator cuff tendon, repair fracture of radius or ulna, laminectomy, repair of ankle fracture, shoulder arthroscopy and debridement, lumbar spinal fusion, repair fracture of the distal part of radius, low back intervertebral disc surgery, incise finger tendon sheath, repair of femoral shaft fracture, and repair of trochanteric fracture.

17. The method of claim 1, wherein administration of the sALP results in:
(i) the increase in bone healing resulting in the new bone formation at a reference point in the subject compared to the reference point in the subject before the treatment; and/or
(ii) an average change in bone mineral density of the reference point that is undetectable or no greater than 0.01% eight months after the administration of the sALP compared to the bone mineral density of the reference point in the subject before the treatment.

18. The method of claim 1, wherein the subject has NF1 and exhibits at least one symptom of NF1 selected from the group consisting of spine curvature, kyphosis, osteoporosis, a weakened vertebra, thinning of a rib, rotation of a vertebra, vertebral wedging, erosion of a vertebra, rotational or angular spinal deformity, dural ectasia, incomplete bone mineralization, elevated blood and/or urine levels of phosphoethanolamine (PEA), hypomineralization, hypercalciuria, short stature, skeletal deformity, waddling gait, bone pain, bone fracture, weakness, and calcium pyrophosphate dihydrate crystal deposition; or wherein the at least one symptom of dystrophic scoliosis comprises one or more of shorter and/or more sharply angulated curves compared to non-dystrophic scoliosis, bone abnormalities, thinning of a rib, a weakened vertebra bone, rotation of a vertebra, vertebral wedging, and erosion of a vertebra.

19. The method of claim 1, wherein the dystrophic scoliosis is NF1-related dystrophic scoliosis.

* * * * *